US008809566B2

(12) United States Patent
Stoessel et al.

(10) Patent No.: US 8,809,566 B2
(45) **Date of Patent: *Aug. 19, 2014**

(54) MATERIALS FOR ORGANIC ELECTROLUMINESCENCE DEVICES

(75) Inventors: Philipp Stoessel, Frankfurt (DE); Holger Heil, Frankfurt (DE); Dominik Joosten, Frankfurt (DE); Christof Pflumm, Frankfurt (DE); Anja Gerhard, Egelsbach (DE)

(73) Assignee: Merck Patent GmbH, Darmstadt (DE)

( * ) Notice: Subject to any disclaimer, the term of this patent is extended or adjusted under 35 U.S.C. 154(b) by 509 days.

This patent is subject to a terminal disclaimer.

(21) Appl. No.: 13/001,657

(22) PCT Filed: Oct. 14, 2009

(86) PCT No.: PCT/EP2009/007361

§ 371 (c)(1), (2), (4) Date: Dec. 28, 2010

(87) PCT Pub. No.: WO2010/054729

PCT Pub. Date: May 20, 2010

(65) Prior Publication Data

US 2011/0105778 A1 May 5, 2011

(30) Foreign Application Priority Data

Nov. 11, 2008 (DE) ........................ 10 2008 056 688

(51) Int. Cl.
*C07F 7/02* (2006.01)

(52) U.S. Cl.
USPC .......................................................... 556/400

(58) Field of Classification Search
USPC .......................................................... 556/400
See application file for complete search history.

(56) References Cited

U.S. PATENT DOCUMENTS

| | | | |
|---|---|---|---|
| 3,532,728 | A | 10/1970 | Fink |
| 5,866,471 | A | 2/1999 | Beppu et al. |
| 2002/0045065 | A1 | 4/2002 | Kim et al. |
| 2003/0022019 | A1 | 1/2003 | Seo et al. |
| 2003/0165711 | A1 | 9/2003 | Kim et al. |
| 2004/0247936 | A1 | 12/2004 | Nakashima et al. |

FOREIGN PATENT DOCUMENTS

| | | | |
|---|---|---|---|
| DE | 1595978 | A1 | 3/1970 |
| DE | 19711154 | A1 | 10/1997 |
| FR | 2314263 | | 1/1977 |
| GB | 1135248 | | 1/1966 |
| JP | 9-31455 | | 2/1997 |
| JP | 9-237927 | A | 9/1997 |
| JP | 9-241255 | | 9/1997 |
| JP | 10-17575 | | 1/1998 |
| JP | 2001-302646 | | 10/2001 |
| JP | 2001-338768 | A | 12/2001 |
| JP | 2003-7471 | | 1/2003 |
| JP | 2003-105206 | | 4/2003 |
| JP | 2007-96086 | | 4/2007 |
| JP | 2007-096102 | A | 4/2007 |
| WO | WO-97/11943 | | 4/1997 |
| WO | WO-03/004021 | | 1/2003 |
| WO | WO-03/102002 | | 12/2003 |
| WO | WO-2004/046275 | | 6/2004 |
| WO | WO-2008/054550 | | 5/2008 |

OTHER PUBLICATIONS

Hill et al., J. Organomet. Chem. 689 (2004) 4165-4183.*

Alvarez et al., "Nematic Tribenzosilatranes," *Liquid Crystals*, vol. 32, No. 4, pp. 469-476 (2005).

Hill et al., "Recent Developments in the Chemistry of Stable Silylenes", *Journal of Organometalllic Chemistry*, vol. 689, pp. 4165-4183 (2004).

Heinicke et al., "Synthesis of Silicon Heterocycles Via Gas Phase Cycloaddition of Aminomethylsilylenes", *Journal of Organometallic Chemistry*, vol. 561, pp. 121-129 (1998).

Wenzel et al., "A Novel Synthesis of Tetraaminoethenes by Reduction of Oxalic Amidines and Subsequent Electrophilic Substitution," *Eur. J. Org. Chem.*, pp. 183-187 (1998).

Su, "Theoretical Study of Halophilic Reactions of Stable Silylenes with Chloro- and Bromocarbons," *J. Am. Chem. Soc.*, vol. 125, pp. 1714-1715 (2003).

Kubota et al., "Strained Silacycle-Catalyzed Asymmetric Diels-Alder Cycloadditions: The First Highly Enantioselective Silicon Lewis Acid Catalyst," *Tetrahedron*, vol. 62, pp. 11397-11401 (2006).

Arduengo, et al., "Photoelectron Spectroscopy of a Carbene/Silylene/Germylene Series," *J. Am. Chem. Soc.*, vol. 116, pp. 6641-6649 (1994).

Cai, et al., "Reactions of the stable Bis(Amino)Silylene Si[{N(CH$_2$tBu)}$_2$C$_6$H$_4$—1,2] with Group 3 or Lanthanide Metal Organic Compounds. Crystal Structures of [Ln($\eta^5$—C$_5$H$_6$)$_3$Si{N(CH$_2$tBu)]$_2$C$_6$H$_4$—1,2)]·C$_7$H$_8$ (Ln=Y or Yb)," *Can. J. Chem.*, vol. 78, pp. 1484-1490 (2000).

Blakeman, et al., "Electronic Structure of Stable Benzodiazasilylenes: Photoelectron Spectra and Quantum-Chemical Investigations," *J. Chem. Soc., Dalton Trans.*, pp. 1475-1480 (1996).

Ohmori, et al., "Chromotographic resolution mechanism of a TRIS(1,10-Phenanthroline)Silicon(IV) complex," *J. Coord. Chem.*, vol. 39, pp. 219-230 (1996).

Gehrhus, et al., "Cycloaddition of Thermolytically Generated Methoxymethylsilylene to α,β-Unsaturated Ketones and Imines," *Main Group Metal Chem.*, vol. 21, No. 2, pp. 99-104 (1998).

Hill, et al., "Reactions of Stable Silylenes with Organic Azides," *Organometallics*, vol. 24, pp. 3346-3349 (2005).

Moser, et al., "Formation of Disilanes in the Reaction of Stable Silylenes with Halocarbons," *J. Am. Chem. Soc.*, vol. 127, pp. 14730-14738 (2005).

(Continued)

*Primary Examiner* — Fereydoun G Sajjadi
*Assistant Examiner* — Kofi Adzamli
(74) *Attorney, Agent, or Firm* — Drinker Biddle & Reath LLP

(57) ABSTRACT

The present invention relates to compounds containing a moiety of the formula (1) and to the use thereof in organic electroluminescent devices and to organic electroluminescent devices which comprise compounds of this type.

10 Claims, No Drawings

(56) References Cited

OTHER PUBLICATIONS

Dieck, et al., "Sythese Offenkettiger und Cyclischer, Silylierter 1,2-+Ethen-diamine," *Chem. Ber.*, vol. 116, pp. 136-145 (1983).
Dieck, et al., "[2+2]-Cycloadditionen: Synthese von 1,4-Diamino-1,3-Butadien-2,3-Dicarbonsaure-Derivaten," *Chem. Ber.*, vol. 120, pp. 795-801 (1997).
Heinicke, et al., "Zur Chemie der Silylene: Cycloadditionen von Methoxymethylsilylen Mit Heterodienen," *Journal of Organometallic Chemistry*, vol. 423, pp. 13-21 (1992).
Karsch, "A New Route to Silaheterocycles: Heterobutadiene Cycloaddition," *Organosilicon Chemistry III: from Molecules to Materials, Weinheim, Wiley-VCH*, pp. 53-57 (1998).
Abakumov, G., et al., Doklady Chemistry, vol. 399, No. 1, (2004), pp. 223-225.
Abakumov, G., et al., Doklady Chemistry, vol. 404, No. 2, (2005), pp. 189-192.
Fedushkin, I., et al., Organometallics, vol. 23, No. 15, (2004), pp. 3714-3718.
Karsanov, I., et al., Journal of Organometallic Chemistry, (1989), vol. 379, No. 1-2, pp. 1-25.
Piskunov, A., et al., Russian Chemical Bulletin, (2007), vol. 56, No. 2, pp. 261-266.
Piskunov, A., et al., Eur. J. Inorg. Chem., (2008), vol. 14, No. 32, pp. 10085-10093.
Piskunov, A., et al., Eur. J. Inorg. Chem., (2008), No. 9, pp. 1435-1444.
Bassoul, P., et al., Journal of Physical Chemistry, (1996), vol. 100, No. 8, pp. 3131-3136.
Mancilla, T., et al., Heteroatom Chemistry, (1999), vol. 10, No. 2, pp. 133-139.
Bruni, S., et al., Journal of the American Chemical Society, (1994), vol. 116, No. 4, pp. 1388-1394.
Ravenscroft, M., et al., Journal of Organometallic Chemistry, vol. 312, No. 1, (1986), pp. 33-43.
Gans-Eichler, T., et al., Chemistry—A European Journal, vol. 12, No. 4, (2006), pp. 1162-1173.

* cited by examiner

MATERIALS FOR ORGANIC ELECTROLUMINESCENCE DEVICES

RELATED APPLICATIONS

This application is a national stage application (under 35 U.S.C. §371) of PCT/EP2009/007361, filed Oct. 14, 2009, which claims benefit of German Application No. 10 2008 056 688.8, filed Nov. 11, 2008.

The present invention relates to novel materials for organic electroluminescent devices and to organic electroluminescent devices comprising materials of this type.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. In general, a distinction is made here between fluorescent and phosphorescent OLEDs. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement in OLEDs, in particular also in OLEDs which exhibit triplet emission. Thus, improvements are still desirable in the physical properties of phosphorescent OLEDs with respect to efficiency, operating voltage and lifetime for use of triplet emitters in high-quality and long-lived electroluminescent devices. This applies, in particular, to OLEDs which emit in the relatively short-wavelength range, i.e. green and in particular blue. Thus, no devices comprising blue-emitting triplet emitters which meet the technical requirements for industrial application have hitherto been disclosed.

In accordance with the prior art, the triplet emitters employed in phosphorescent OLEDs are, in particular, iridium complexes. The properties of phosphorescent OLEDs are not determined only by the triplet emitters employed. In particular, the other materials used, such as matrix materials, hole-blocking materials, hole-transport materials and electron- or exciton-blocking materials, are also of particular importance here. Improvements in these materials can thus also result in significant improvements in the OLED properties. There is still also a need for improvement in these materials for fluorescent OLEDs.

US 2004/0048101 discloses electron-blocking layers and OLEDs comprising same which comprise a metal complex which may contain between one and three bidentate ligands. These ligands consist of a pyrazole ring which is linked in the 1-position to a phenyl ring. The ligands are each bonded to the metal atom via the 2-position of the two rings. The metal complex optionally contains further mono- or bidentate ligands. The metal atom is preferably iridium.

US 2008/0093988 discloses a particular OLED structure comprising a plurality of emitting layers. This device structure is characterised by the presence of an electron- or exciton-blocking layer between the emitting layers. A hole-transport material in combination with $Ir(ppy)_3$ is employed for this layer.

WO 04/084260 discloses OLEDs comprising a layer which comprises a hole-transport material and an electron-blocking material, where this layer preferably comprises compounds having a triaryl structure, which may also occur as recurring unit in a polymer.

WO 07/120,788 discloses OLEDs having an organic layer comprising a phthalimide compound which is located between the electrodes. The phthalimide compound here is employed, inter alia, in an exciton-blocking layer.

WO 08/034,758 discloses OLEDs which comprise at least one compound containing at least one structural element of carbazole in at least one of the layers, where the nitrogen atom of the carbazole may be substituted by various organic radicals or even replaced entirely by other heteroatoms or functional groups which contain heteroatoms. The above-mentioned compound can take on the function of a hole-blocking and/or exciton-blocking material here.

The object of the present invention is to provide compounds which are suitable for use in a fluorescent or phosphorescent OLED, in particular a phosphorescent OLED, for example as matrix material or as hole-transport/electron-blocking material or exciton-blocking material. In particular, the object is to provide exciton-blocking materials or electron-blocking materials and matrix materials which are suitable for blue- and green-phosphorescent OLEDs.

Surprisingly, it has been found that certain compounds described in greater detail below achieve this object and result in significant improvements in the organic electroluminescent device, in particular with respect to the lifetime, the efficiency and the operating voltage. This applies, in particular, to blue- and green-phosphorescent electroluminescent devices. The present invention therefore relates to these compounds and to organic electroluminescent devices which comprise compounds of this type.

The present invention thus relates to compounds containing at least one moiety of the formula (1)

formula (1)

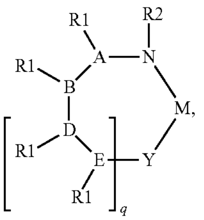

in which

M is selected from the group consisting of Si, Ge and Sn;

q is 0 or 1;

A, B, D and E are each a C atom; a double bond or aromatic bond is present between A and B if A does not form an aromatic system with N, and a single bond is present between A and B if A forms an aromatic system with N; furthermore, a double bond or aromatic bond is present between D and E if E does not form an aromatic system with Y, and a single bond is present between D and E if E forms an aromatic system with Y;

Y is selected from the group consisting of NR2, O and S;

R1 is selected from the group consisting of H, D, F, Cl, Br, I, CN, $NO_2$, $N(R3)_2$, a straight-chain alkyl, alkoxy or thioalkyl group having 1 to 40 C atoms or a branched or cyclic alkyl, alkoxy or thioalkyl group having 3 to 40 C atoms or an alkenyl group having 2 to 40 C atoms, each of which may be substituted by one or more radicals R3, where one or more non-adjacent $CH_2$ groups may be replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms may be replaced by D, F, Cl, Br, I, CN or $NO_2$, an aromatic or heteroaromatic ring system having 5 to 60 aromatic ring atoms, which may in each case be substituted by one or more radicals R3, an aryloxy or heteroaryloxy group having 5 to 60 aromatic ring atoms, which may be substituted by one or more radicals R3, or a combination of these systems, where two or more adjacent substituents R1 may optionally form a monocyclic or polycyclic aliphatic, aromatic or heteroaromatic ring system which is condensed in a linear or angular manner and which may be substituted by one or more radicals R3;

R2 is selected from the group consisting of a straight-chain alkyl group having 1 to 40 C atoms or a branched or cyclic alkyl group having 3 to 40 C atoms, each of which may be substituted by one or more radicals R3, where one or more non-adjacent $CH_2$ groups may be replaced by R3C═CR3, C≡C or C═O and where one or more H atoms may be replaced by F, Cl, Br, I, CN or $NO_2$, an aromatic or heteroaromatic ring system having 5 to 60 aromatic ring atoms, which may in each case be substituted by one or more radicals R3, or a combination of these systems; with the proviso that at least one group R2 which represents an aromatic or heteroaromatic ring system, which may in each case be substituted by one or more radicals R3, is present in the structure of the formula (1); R1 and R2 which are adjacent to one another in the 1,2-position in the moiety of the formula (1) may optionally form a monocyclic or polycyclic aliphatic, aromatic or heteroaromatic ring system which is condensed in a linear or angular manner and which may be substituted by one or more radicals R3;

R3 is selected from the group consisting of H, D, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I, CN or $NO_2$, where two or more adjacent substituents R3 may form a mono- or polycyclic aliphatic, aromatic or heteroaromatic ring system which is condensed in a linear or angular manner with one another;

the following compounds are excluded from the invention:

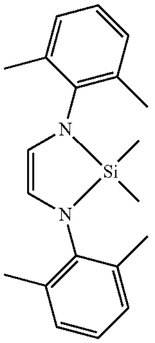

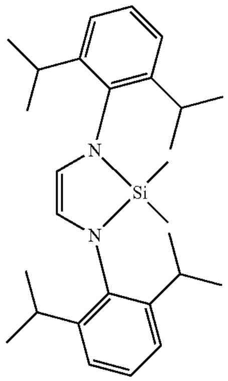

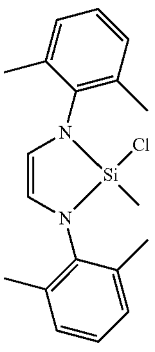

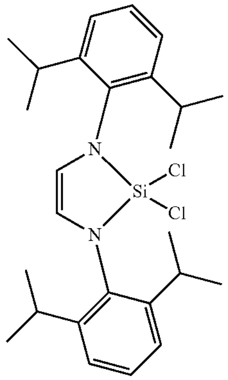

-continued

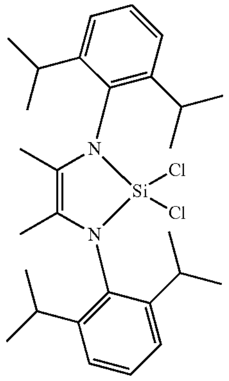

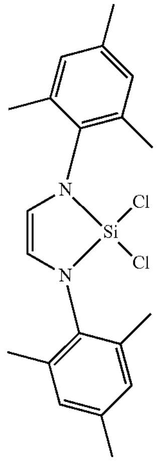

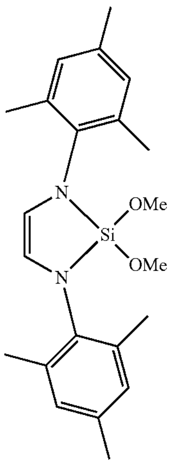

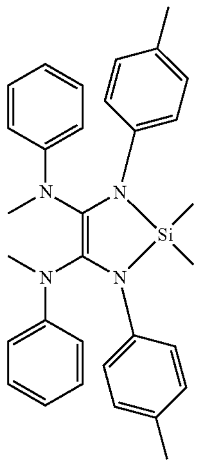

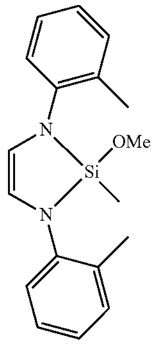

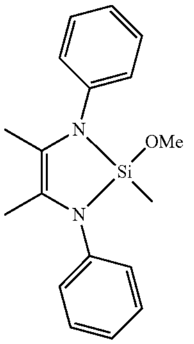

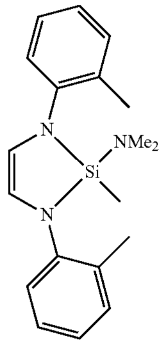

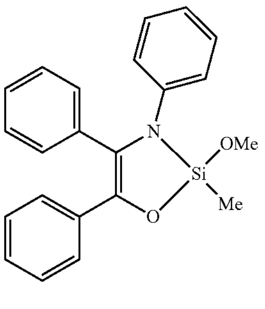

-continued
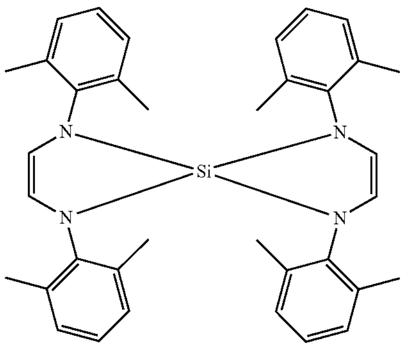
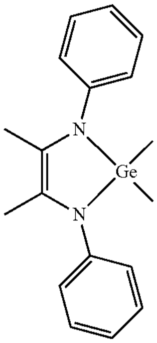
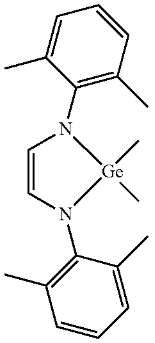
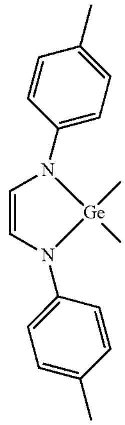
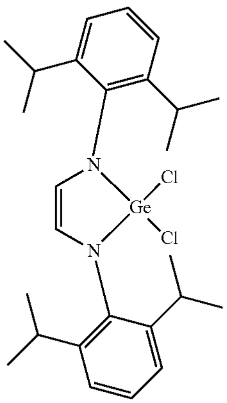
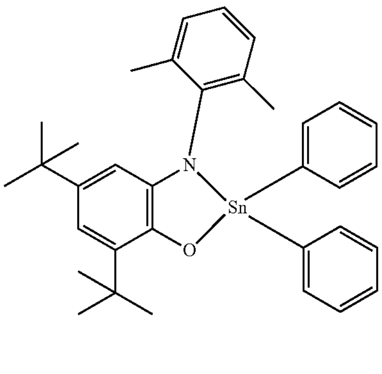
-continued
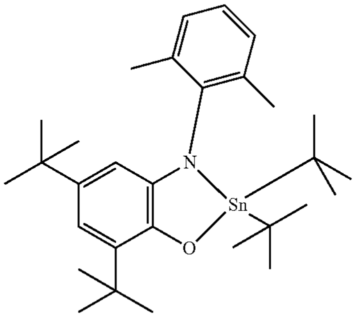
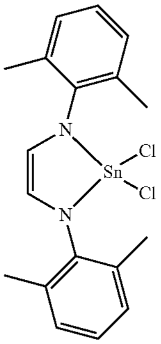
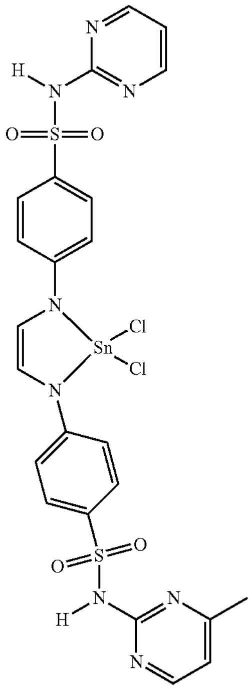
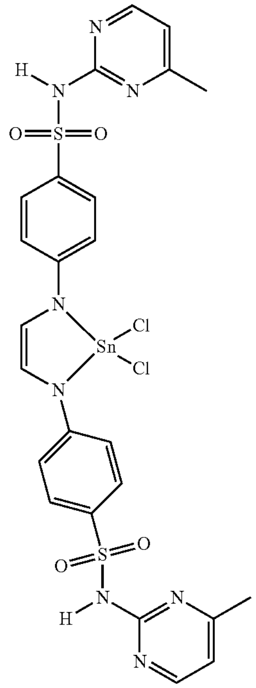
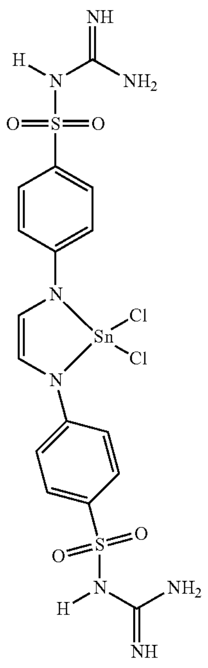

-continued

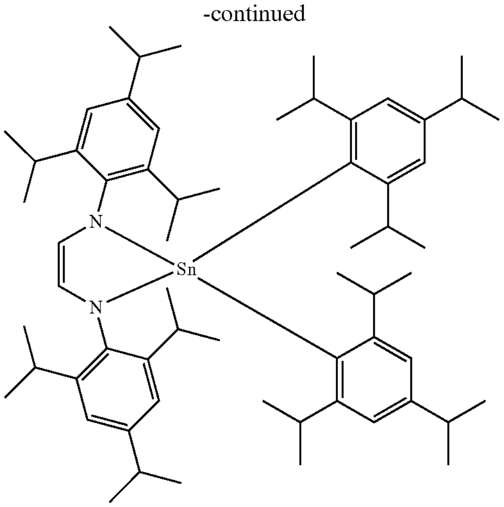

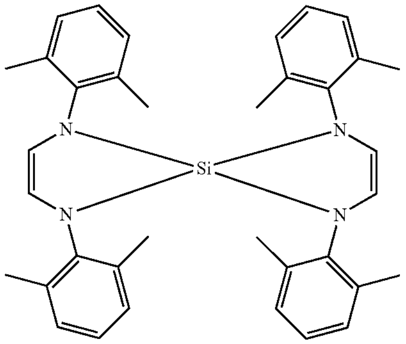

The bond between M and N or Y here can either be coordinative, i.e. as in a ligand field, or covalent, where the bond type is determined by the metal or semimetal M.

The ligand or group which is bonded or coordinated to M is preferably not part of a porphyrin structure or porphyrin derivative. This structure thus preferably does contain four pyrrole groups or pyrrole derivatives which are bonded to form a cyclic structure.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, an $sp^3$-hybridised C, N or O atom. Thus, for example, systems such as 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a linear or cyclic alkyl group or by a silyl group.

For the purposes of the present invention, an aliphatic hydrocarbon radical or an alkyl group, which may typically contain 1 to 40 or also 1 to 20 C atoms, and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3; furthermore, one or more H atoms may also be replaced by F, Cl, Br, I, CN or $NO_2$, preferably F, Cl or CN, furthermore preferably F or Cl, particularly preferably F.

An aromatic or heteroaromatic ring system having 5-60 aromatic ring atoms, which may also in each case be substituted by the above-mentioned radicals R2 or a hydrocarbon radical and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoroanthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds according to the invention which are uncharged, i.e. are electrically neutral. This is achieved in a simple manner by selecting the charge of the radicals or ligands coordinated or covalently bonded to M so that they compensate for the charge of M.

In the compounds of the present invention, R1, R2, R3 and Y may in each case, independently of one another on each occurrence, be either identical or different in a structure or moiety. In particular, R1 and R2 which are adjacent to one another in the 1,2-position in the moiety of the formula (1) may form a monocyclic or polycyclic aliphatic, aromatic or heteroaromatic ring system which is condensed in a linear or angular manner. In these cases, R1 which are adjacent to one another in the 1,2-position preferably then do not form a ring system with one another.

The present invention provides, in particular, compounds containing the above-mentioned moiety of the formula (1), where q=0, a single bond is present between A and B, R1 and R2 which are adjacent to one another in the 1,2-position in the moiety of the formula (1) form a monocyclic or polycyclic aromatic or heteroaromatic ring system.

The present invention furthermore provides, in particular, compounds containing the above-mentioned moiety of the formula (1), where q=0, a double bond is present between A and B, and the two substituents R1 which are adjacent to one another in the moiety of the formula (1) form a monocyclic or polycyclic aliphatic, aromatic or heteroaromatic ring system which is condensed in a linear or angular manner, in particular an aromatic or heteroaromatic ring system.

The present invention furthermore provides, in particular, compounds containing the above-mentioned moiety of the formula (1), where q=1, a double bond is present between A and B, a double bond is present between D and E, two or in each case two substituents R1 which are adjacent to one another in the 1,2-position in the moiety of the formula (1) form a monocyclic or polycyclic aliphatic, aromatic or heteroaromatic ring system which is condensed in a linear or angular manner, in particular an aromatic or heteroaromatic ring system.

In particular, preference is given to compounds in accordance with the above-mentioned embodiments containing a moiety of the formula (2) to (8):

formula (2)

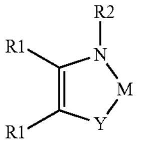

formula (3)

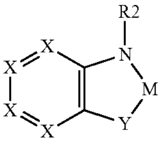

-continued formula (4)

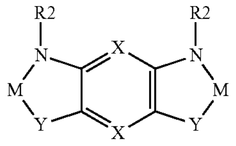

formula (5)

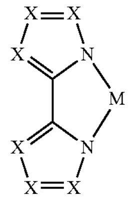

formula (6)

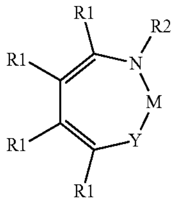

formula (7)

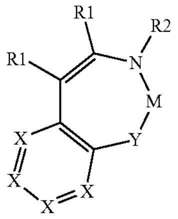

formula (8)

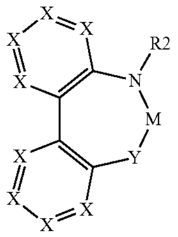

in which M, R1, R2, R3 and Y are as defined above and X is selected, identically or differently on each occurrence, from the group consisting of CR1 and N.

Preference is furthermore given to compounds in accordance with one or more of the above-mentioned embodiments having a structure of the formula (9)

formula (9)

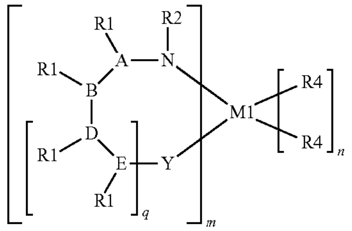

in which A, B, D, E, R1, R2, R3, Y and q are as defined above and furthermore:

M1 is Si, Ge or Sn;

R4 is identical or different on each occurrence and is selected from the group consisting of F, Cl, Br, I, $N(R3)_2$, a straight-chain alkyl, alkoxy or thioalkyl group having 1 to 40 C atoms and a branched or cyclic alkyl, alkoxy or thioalkyl group having 3 to 40 C atoms and an alkenyl group having 2 to 40 C atoms, each of which may be substituted by one or more radicals R3, where one or more non-adjacent $CH_2$ groups may be replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms may be replaced by D, F, Cl, Br, I, CN or $NO_2$, an aromatic or heteroaromatic ring system having 5 to 60 aromatic ring atoms, which may in each case be substituted by one or more radicals R3, an aryloxy or heteroaryloxy group having 5 to 60 aromatic ring atoms, which may be substituted by one or more radicals R3, or a combination of these systems, where two or more substituents R4 may optionally form a monocyclic or polycyclic aliphatic, aromatic or heteroaromatic ring system which is condensed in a linear or angular manner and which may be substituted by one or more radicals R3;

m is 1 or 2;

n is (2−m).

In a preferred embodiment of the formula (9), q=0.

Preferred compounds of the formula (9) are furthermore the compounds of one of the formulae (10) to (17):

formula (10)

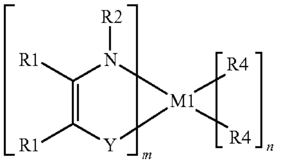

formula (11)

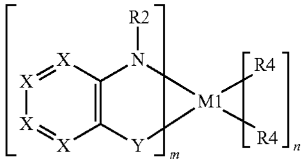

formula (12)

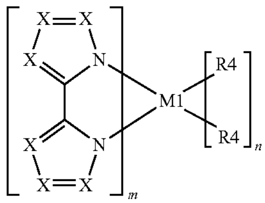

formula (13)

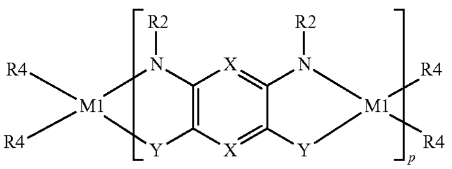

formula (14)

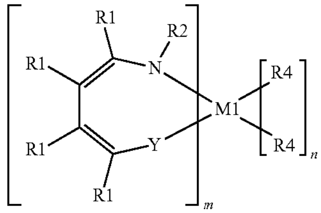

-continued formula (15)

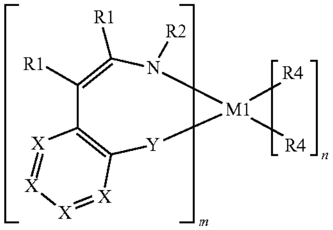

formula (16)

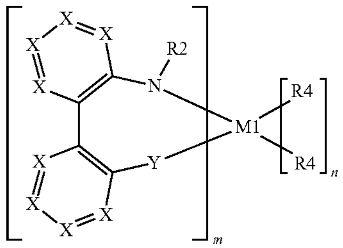

formula (17)

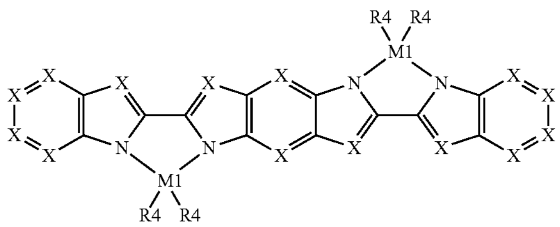

in which M1, R1, R2, R3, R4, X, Y, m and n are as defined above and p is an integer from 1 to 100,000, preferably 1 to 10,000, particularly preferably 1 to 100, very particularly preferably 1.

In a preferred embodiment of the compounds of the formulae (9) to (17), m=2 and n=0.

Preference is given to compounds of the formulae (9) to (17) in which M1 stands for Si or Ge, in particular Si.

Preference is furthermore given to compounds of the formulae (9) to (17) in which Y stands for NR2 or O, in particular NR2.

Preference is furthermore given to compounds of the formulae (9) to (17) in which X stands for CR1.

Preference is furthermore given to compounds of the formulae (9) to (17) in which R4 is selected on each occurrence, identically or differently, from the group consisting of a straight-chain alkyl group having 1 to 20 C atoms and a branched or cyclic alkyl group having 3 to 20 C atoms, each of which may be substituted by one or more radicals R3, where one or more non-adjacent $CH_2$ groups may be replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms may be replaced by F, Cl, Br, I, CN or $NO_2$, an aromatic or heteroaromatic ring system having 5 to 60 aromatic ring atoms, which may in each case be substituted by one or more radicals R3, or a combination of these systems, where two or more substituents R4 may optionally form a monocyclic or polycyclic aliphatic, aromatic or heteroaromatic ring system which is condensed in a linear or angular manner and which may be substituted by one or more radicals R3.

Preference is furthermore given to compounds of the formulae (9) to (17) in which (i) q=0 and a single bond is present between A and B;

(ii) M1 is selected from the group consisting of Si, Ge, Sn, preferably selected from the group consisting of Si, Ge, is most preferably Si;

(iii) Y is equal to NR2;

(iv) R1 and R2 which are adjacent to one another in the 1,2-position in the structure of the formula (1) preferably form a monocyclic or polycyclic aliphatic, aromatic or heteroaromatic ring system which is condensed in a linear or angular manner together with the C atom located in the 1-position with respect to R1 and the N atom located in the 1-position with respect to R2, furthermore preferably form a monocyclic heteroaromatic ring system, most preferably a pyrrole ring, together with the C atom located in the 1-position with respect to R1 and the N atom located in the 1-position with respect to R2, where the ring system may be substituted by one or more hydrocarbon radicals having 1 to 20 C atoms, in which one or more H atoms may be replaced by F, Cl or CN, preferably F or Cl, most preferably F, where the ring system is preferably unsubstituted; and (v) m is 1 or 2 and n=(2−m), preferably m=2 and n=0.

Preferred embodiments are furthermore compounds of one of the above-mentioned formulae in which (i) q=1, a double bond or aromatic bond is present between A and B, and a double bond or aromatic bond is present between D and E;

(ii) M1 is selected from the group consisting of Si, Ge, Sn, preferably consisting of Si and Ge, is most preferably Si;

(iii) Y is equal to NR2;

(iv) R2 is selected from the group consisting of an aliphatic hydrocarbon radical having 1 to 20 C atoms, an aromatic or heteroaromatic ring system having 5 to 30 aromatic ring atoms, in which one or more H atoms may be replaced by F atoms, where two or more adjacent substituents R2 may form a mono- or polycyclic aliphatic, aromatic or heteroaromatic ring system which is condensed in a linear or angular manner with one another, R2 is preferably selected from the group consisting of an aromatic ring system having 5 to 30 aromatic ring atoms, in which one or more H atoms may be replaced by F atoms, R2 is most preferably a phenyl ring, where the ring system may be substituted by one or more hydrocarbon radicals having 1 to 20 C atoms, in which one or more H atoms may be replaced by F, Cl or CN, preferably F or Cl, most preferably F, where the ring system is preferably unsubstituted;

(v) the two substituents R1 adjacent to A and B, preferably together with A and B, and the two substituents R1 adjacent to D and E, preferably together with D and E, in each case form a monocyclic or polycyclic aliphatic, aromatic or heteroaromatic ring system which is condensed in a linear or angular manner, furthermore preferably the two substituents R1 adjacent to A and B, together with A and B, and the two substituents R1 adjacent to D and E, together with D and E, in each case form a monocyclic aromatic ring system, most preferably in each case form a phenylene ring, where the ring system may be substituted by one or more hydrocarbon radicals having 1 to 20 C atoms, in which one or more H atoms may be replaced by F, Cl or CN, preferably F or Cl, most preferably F, where the ring system is preferably unsubstituted; and (vi) m is 1 or 2 and n=(2−m), preferably m=2 and n=0.

Preference is furthermore given to compounds of the above-mentioned formulae in which:

M1 is selected from the group consisting of Si, Ge, preferably Si;

R1 is as defined above;

R2 is an aromatic or heteroaromatic ring system having 5 to 30 aromatic ring atoms, in which one or more H atoms are optionally replaced by F atoms and which may in each case be substituted by one or more radicals R3;

X is equal to CR1;

Y is equal to NR2.

In a particularly preferred embodiment of the invention, R2 stands for phenyl, naphthyl or biphenyl, each of which may be substituted by one or more radicals R3.

Preference is furthermore given to compounds which have a symmetrical structure and are identically substituted. This preference is due to the easier synthetic accessibility of these compounds.

For the preparation of the compounds according to the invention, the process described below has proven particularly suitable. To this end, a compound $M(Hal)_{2m}(R4)_{2n}$, in particular a compound $M(Hal)_4$, where Hal stands for Cl, Br or I, is reacted with a corresponding diamine, aminoalcohol, aminothiol or the respective deprotonated compound.

The present invention therefore furthermore relates to a process for the preparation of the above-mentioned compounds according to the invention by reaction of $M(Hal)_{2m}(R4)_{2n}$, in particular $MHal_4$, where M, m and n have the above-mentioned meaning and Hal stands for Cl, Br or I, with a corresponding diamine, aminoalcohol, aminothiol or the respective deprotonated compound.

The above-described compounds according to the invention, in particular compounds which are substituted by reactive leaving groups, such as bromine, iodine, boronic acid or boronic acid ester, or by polymerisable groups, such as olefins or oxetanes, can be used as monomers for the generation of corresponding oligomers, dendrimers or polymers. The oligomerisation or polymerisation here is preferably carried out via the halogen functionality or the boronic acid functionality.

A further possibility for polymerisation consists in the reaction of a compound $MHal_4$, where Hal stands for Cl, Br or I, for example $SiCl_4$, with a tetramine, which then forms the ligand.

A further possibility for polymerisation consists in functionalising the above-mentioned compounds according to the invention with reactive, polymerisable groups and then polymerising the latter. Examples of functional groups of this type are alkenes or alkene derivatives or oxetanes. It is furthermore possible to crosslink the polymers via groups of this type.

The compounds or polymers according to the invention can be employed as crosslinked or uncrosslinked layer.

The invention therefore furthermore relates to oligomers, polymers or dendrimers containing one or more of the above-mentioned compounds according to the invention, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. For the recurring units of the compounds according to the invention in oligomers, dendrimers and polymers, the same preferences apply as described above.

For the preparation of the oligomers or polymers, the monomers according to the invention are homopolymerised or copolymerised with further monomers. Preference is given to homopolymers or copolymers in which the units of the formulae (1) to (17) are present in an amount of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The polymers, oligomers and dendrimers may also contain further units, for example hole-transport units, in particular those based on triarylamines, and/or electron-transport units. In addition, the polymers may contain triplet emitters, either copolymerised or mixed in as a blend. Precisely the combination of units of the formulae (1) to (17) with triplet emitters gives particularly good results.

The compounds according to the invention may furthermore also be functionalised further and thus converted into extended structures. An example which may be mentioned here is functionalisation with arylboronic acids by the SUZUKI method or with primary or secondary amines by the HARTWIG-BUCHWALD method.

Compounds in which a main-group element or a transition metal is substituted or coordinated by one or more substituents or ligands as described above, in particular the above-mentioned compounds according to the invention, are particularly suitable for use in an organic electronic component. An organic electronic component here is taken to mean a device which comprises at least one layer which comprises at least one organic compound. However, the component may also comprise inorganic materials.

The present invention therefore furthermore relates to the use of a compound containing at least one moiety of the formula (1*)

formula (1*)

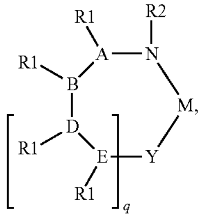

in which:

M is selected from the group consisting of Si, Ge, Sn, Ti, Zr, Hf, Cr, Mo and W;

R2 is on each occurrence, identically or differently, a straight-chain alkyl group having 1 to 40 C atoms or a branched or cyclic alkyl group having 3 to 40 C atoms, each of which may be substituted by one or more radicals R3, where one or more non-adjacent $CH_2$ groups may be replaced by R3C=CR3, CEC or C=O and where one or more H atoms may be replaced by D, F, Cl, Br, I, CN or $NO_2$, an aromatic or heteroaromatic ring system having 5 to 60 aromatic ring atoms, which may in each case be substituted by one or more radicals R3, or a combination of these systems; R1 and R2 which are adjacent to one another in the 1,2-position in the moiety of the formula (1*) may optionally form a monocyclic or polycyclic aliphatic, aromatic or heteroaromatic ring system which is condensed in a linear or angular manner and which may be substituted by one or more radicals R3;

the other symbols and indices used have the above-mentioned meanings;

or of an oligomer, polymer or dendrimer containing this moiety in organic electronic components.

The invention again furthermore relates to organic electronic components, in particular organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but in particular organic electroluminescent devices (OLEDs), particularly preferably phosphorescent OLEDs, comprising one or more compounds containing a moiety of the formula (1*) depicted above or oligomers, polymers or dendrimers containing this moiety.

Particular preference is given to organic electronic devices comprising compounds of the formula (9*)

formula (9*)

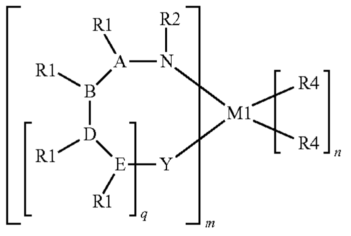

or in particular of the formulae (10*) to (17*):

formula (10*)

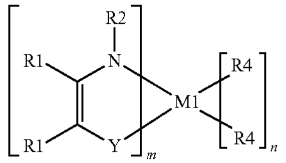

formula (11*)

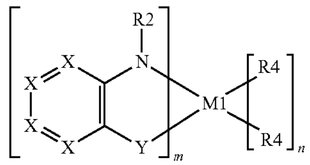

formula (12*)

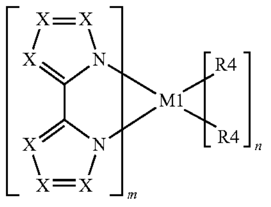

formula (13*)

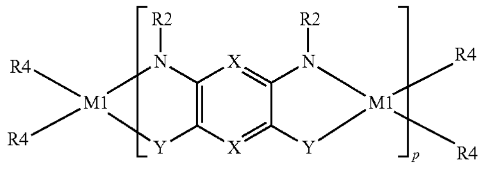

-continued formula (14*)

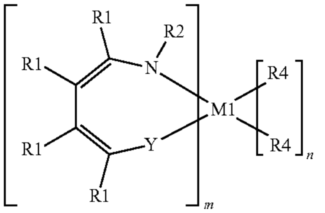

formula (15*)

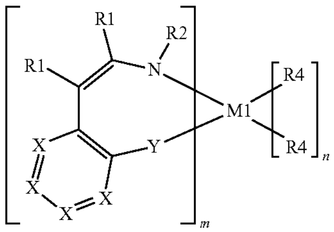

formula (16*)

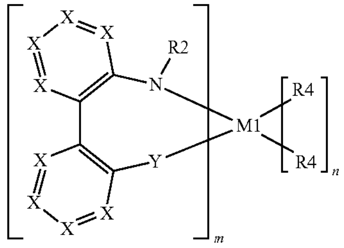

formula (17*)

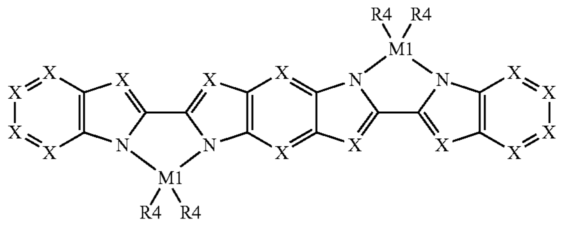

in which R2 has the meanings mentioned above for formula (1*), M1 is selected from Si, Ge, Sn, Ti, Zr, Hf, Cr, Mo and W, and the other symbols and indices used have the meanings mentioned above for formulae (1) to (17), and furthermore:

m is 1 or 2 for M1=Si, Ge, Sn, Ti, Zr or Hf, and 1, 2 or 3 for M1=Cr, Mo or W;

n is (2−m) for M1=Si, Ge, Sn, Ti, Zr or Hf, and (3−m) for M1=Cr, Mo or W.

For the symbols used, the same preference applies as mentioned above for the product protection.

Preference is therefore given to compounds of the formulae (9*) to (17*) where m=2 and n=0.

Preference is furthermore given to compounds of the formulae (9*) to (17*) in which M1 stands for Si or Ge, in particular Si.

Preference is furthermore given to compounds of the formulae (9*) to (17*) in which Y stands for NR2 or O, in particular NR2.

Preference is furthermore given to compounds of the formulae (9*) to (17*) in which X stands for CR1.

Preference is furthermore given to compounds of the formulae (9*) to (17*) in which R4 is selected on each occurrence, identically or differently, from the group consisting of a straight-chain alkyl group having 1 to 20 C atoms and a branched or cyclic alkyl group having 3 to 20 C atoms, each of which may be substituted by one or more radicals R3, where one or more non-adjacent $CH_2$ groups may be replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms may be replaced by F, Cl, Br, I, CN or $NO_2$, an aromatic or heteroaromatic ring system having 5 to 60 aromatic ring atoms, which may in each case be substituted by one or more radicals R3, or a combination of these systems, where two or more substituents R4 may optionally form a monocyclic or polycyclic aliphatic, aromatic or heteroaromatic ring system which is condensed in a linear or angular manner and which may be substituted by one or more radicals R3.

Preference is furthermore given to compounds of the formulae (9*) to (17*) in which:

M1 is selected from the group consisting of Si and Ge, preferably Si;

R1 is as defined above;

R2 is an aromatic or heteroaromatic ring system having 5 to 30 aromatic ring atoms, in which one or more H atoms are optionally replaced by F atoms and which may in each case be substituted by one or more radicals R3;

X is equal to CR1;

Y is equal to NR2.

In a particularly preferred embodiment of the compounds of the formulae (9*) to (17*), R2 stands for phenyl, naphthyl or biphenyl, each of which may be substituted by one or more radicals R3.

The organic electroluminescent device comprises a cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013).

The compound in accordance with the above-mentioned embodiments can be employed in various layers here, depending on the precise structure. Preference is given to an organic electroluminescent device comprising a compound according to the invention in an electron-blocking or exciton-blocking layer and/or in a hole-transport layer and/or as matrix material for fluorescent or phosphorescent emitters. In a preferred embodiment of the invention, the compounds of the formulae (9*) to (17*) are employed in an electron-blocking or exciton-blocking layer in a phosphorescent OLED or in an emitting layer as matrix for phosphorescent emitters. The above-mentioned preferred embodiments for the compounds also apply here to the use of the materials in organic electronic devices. Particular preference is given to the use of the compounds of the formulae (9) to (17) according to the invention.

In a preferred embodiment of the invention, the compound of the formula (1*) or of the formulae (9*) to (17*) is employed as matrix material for a fluorescent or phosphorescent compound in an emitting layer. The organic electroluminescent device here may comprise one emitting layer or a plurality of emitting layers, where at least one emitting layer comprises at least one compound of the formulae (9*) to (17*) as matrix material. If a plurality of emission layers are present, the comments made above apply to these.

If the compound of the formula (1*) or (9*) to (17*) is employed as matrix material for an emitting compound in an emitting layer, it is preferably employed in combination with one or more phosphorescent materials (triplet emitters). For the purposes of this invention, phosphorescence is taken to mean the luminescence from an excited state with relatively high spin multiplicity, i.e. a spin state >1, in particular from an excited triplet state. For the purposes of this application, all luminescent iridium and platinum complexes are to be regarded as phosphorescent compounds. The mixture of the compound of the formula (1*) or (9*) to (17*) and the emitting compound then comprises between 99 and 1% by vol., preferably between 98 and 10% by vol., particularly preferably between 97 and 60% by vol., in particular between 95 and 85% by vol., of the compound of the formula (1*) or (9*) to (17*), based on the entire mixture of emitter and matrix material. Correspondingly, the mixture comprises between 1 and 99% by vol., preferably between 2 and 90% by vol., particularly preferably between 3 and 40% by vol., in particular between 5 and 15% by vol., of the emitter, based on the entire mixture of emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides and aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with the unpublished application DE 102008036982.9, WO 07/063,754 or WO 08/056,746, or zinc complexes, for example in accordance with EP 652273 or WO 09/062,578.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step. Preferred ligands are 2-phenylpyridine derivatives, 7,8-benzoquinoline derivatives, 2-(2-thienyl)-pyridine derivatives, 2-(1-naphthyl)pyridine derivatives, 1-phenylisoquinoline derivatives or 2-phenylquinoline derivatives. All these compounds may be substituted, for example by fluorine, cyano and/or trifluoromethyl substituents for blue. Auxiliary ligands are preferably acetylacetonate or picric acid.

Also particularly suitable are complexes of Pt or Pd with tetradentate ligands (US 2007-0087219 A1), Pt porphyrin complexes having an enlarged ring system (US 2009/0061681 A1) and Ir complexes, for example 2,3,7,8,12,13,17,18-octaethyl-21H, 23H-porphyrin-Pt(II), tetraphenyl-Pt(II)-tetrabenzoporphyrin (US 2009/0061681 A1), cis-bis(2-phenylpyridinato-N,$C^{2'}$)Pt(II), cis-bis(2-(2'-thienyppyridinato-N,$C^{3'}$)Pt(II), cis-bis(2-(2'-thienyl)quinolinato-N,$C^{5'}$)Pt(II), (2-(4,6-difluorophenyl)pyridinato-N,$C^{2'}$)Pt(II) acetylacetonate, or tris(2-phenylpyridinato-N,$C^{2}$*(III) ($Ir(ppy)_3$), bis(2-phenylpyridinato-N,$C^{2}$)Ir(III) acetylacetonate ($Ir(ppy)_2$ acetylacetonate, US 2001/0053462 A1, Baldo, Thompson et al. Nature 403, (2000), 750-753), bis(1-phenylisoquinolinato-N,$C^{2'}$)(2-phenylpyridinato-N,$C^{2'}$)iridium(III), bis(2-phenylpyridinato-N,$C^{2'}$)(1-phenylisoquinolinato-N,$C^{2'}$)iridium(III), bis(2-(2'-benzothienyl)pyridinato-N,$C^{3'}$)iridium(III) acetylacetonate, bis(2-(4',6'-difluorophenyl)Pyridinato-N,$C^{2'}$)iridium(III) picolinate (Firpic), bis(2-(4',6'-difluorophenyl)pyridinato-N,$C^{2'}$)Ir(III) tetrakis(1-pyrazolyl)borate, tris(2-(biphenyl-3-yl)-4-tert-butylpyridine)iridium(III), $(ppz)_2$Ir(5phdpym) (US 2009/0061681 A1), $(45ooppz)_2$Ir(5phdpym) (US 2009/0061681 A1), derivatives of 2-phenylpyridine-Ir complexes, such as, for example, tris(2-phenylisoquinolinato-N,C)Ir(III), bis(2-(2'-benzo[4,5-a]thienyl)pyridinato-N,$C^{3}$)Ir acetylacetonate ([$Btp_2$Ir(acac)], Adachi et al. Appl. Phys. Lett. 78 (2001), 1622-1624). Further phosphjorescent emitters with tridentate ligands are described in U.S. Pat. No. 6,824,895. Red-emitting phosphorescent complexes are found in U.S. Pat. No. 6,835,469, U.S. Pat. No. 6,830,828 and US 2001/0053462.

In a further preferred embodiment of the invention, the compound of the formula (1*) or (9*) to (17*) is employed as hole-transport material in a hole-transport or hole-injection layer. A hole-injection layer here is taken to mean a layer which is directly adjacent to an electrically conductive layer. A hole-transport layer is taken to mean a layer which is between a hole-injection layer and the emitting layer or an electron-blocking layer or exciton-blocking layer. The emitting layer here may be fluorescent or phosphorescent.

In still a further preferred embodiment of the invention, the compound of the formula (1*) or (9*) to (17*) is employed in an electron-blocking layer or exciton-blocking layer. An electron-blocking layer is taken to mean a layer which is directly adjacent to an emitting layer on the anode side. This may also have exciton-blocking properties. The position of HOMO and LUMO of the material of the electron-blocking layer reduces the transfer of electrons from the emitting layer into the hole-transport layer. In particular in the case of phosphorescent OLEDs, the use of an electron-blocking layer of this type can result in advantages.

It is furthermore possible to use the compound according to the invention both in an electron-blocking layer or exciton-blocking layer and as matrix in an emitting layer.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 05/053051. It is furthermore possible to use a metal complex which is identical or similar to the metal complex in the emitting layer as hole-transport or hole-injection material directly adjacent to the emitting layer, as described, for example, in WO 09/030,981.

Preference is furthermore given to an organic electroluminescent device, characterised in that one or more layers are applied by means of a sublimation process, in which the materials are vapour-deposited in vacuum sublimation units at an initial pressure of usually less than le mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-6}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose.

These processes are generally known to the person skilled in the art and can be applied by him without problems to organic electroluminescent devices comprising the compounds according to the invention.

Examples of preferred compounds according to the invention in accordance with the above-mentioned embodiments or compounds as can preferably be employed in organic electronic devices are the compounds of the following structures (1) to (280).

(1)

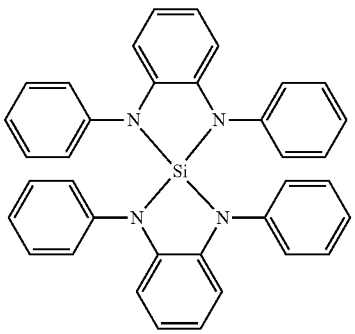

-continued (2)

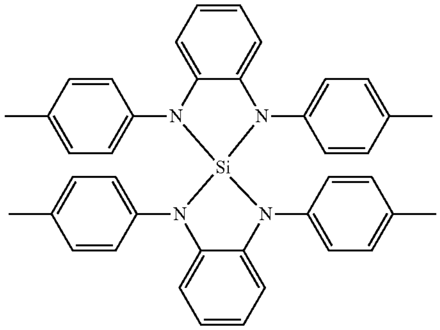

(3)

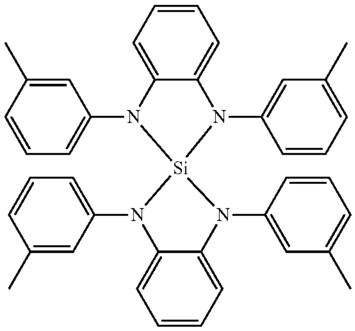

(4)

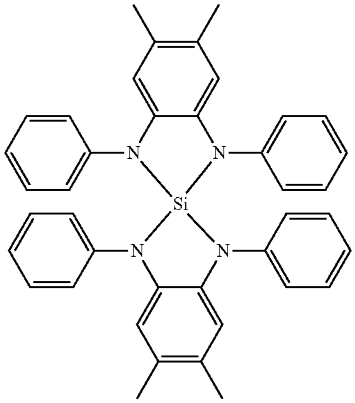

(5)

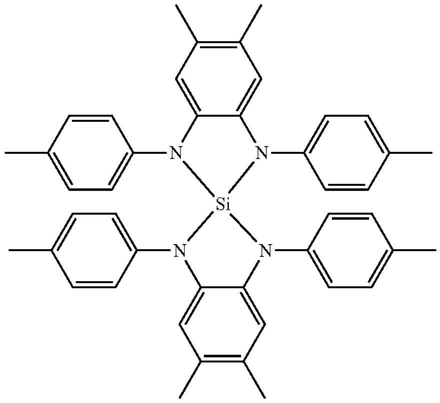

-continued
(6)
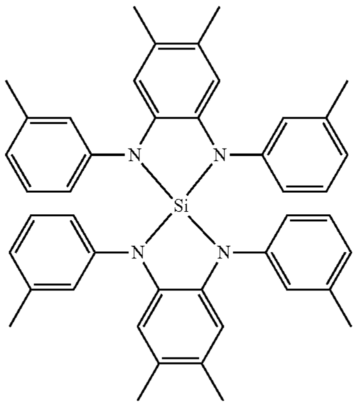
(7)
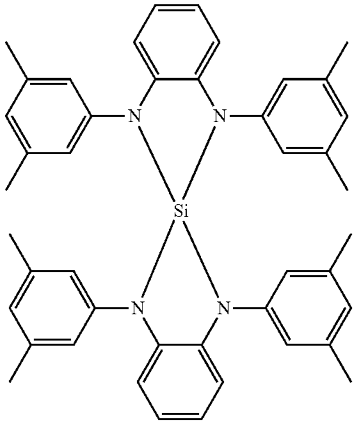
(8)
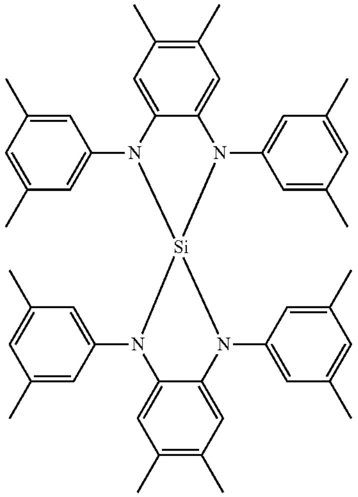
-continued
(9)
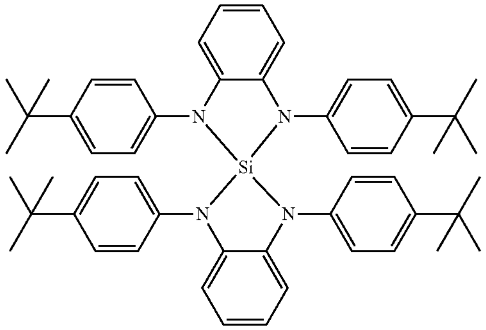
(10)
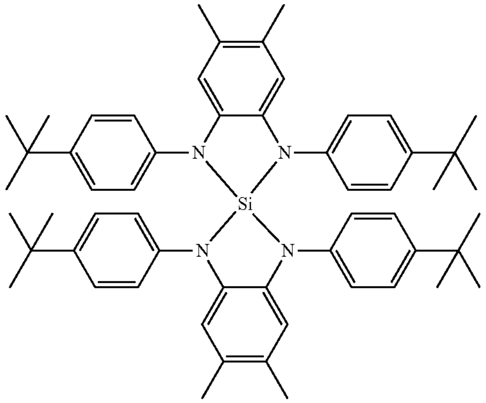
(11)
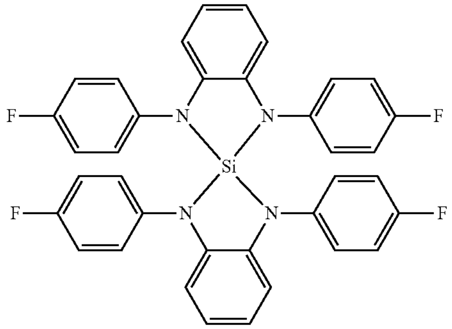
(12)
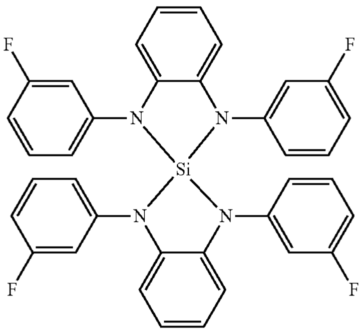

-continued
(13)
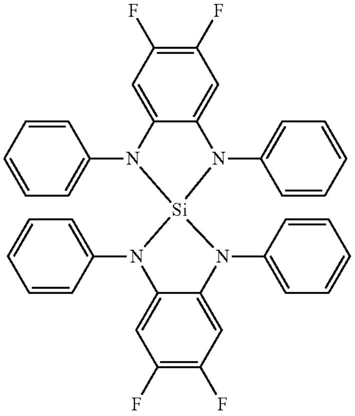
(14)
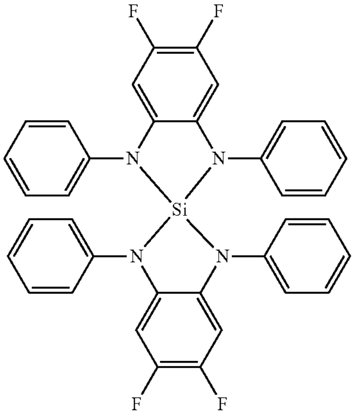
(15)
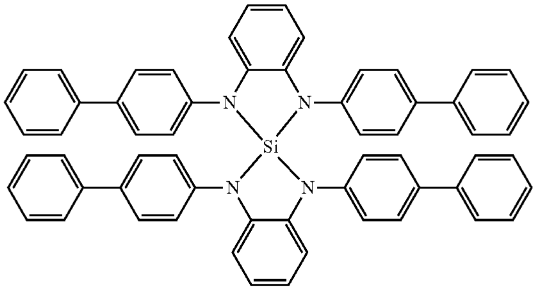
(16)
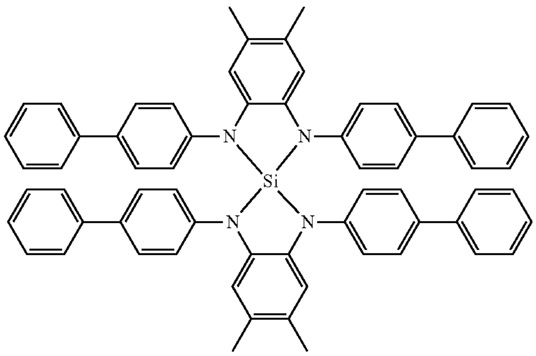
-continued
(17)
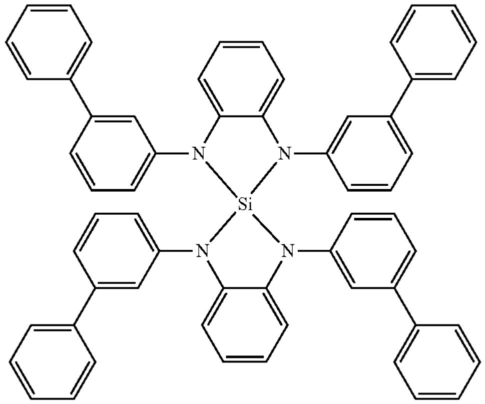
(18)
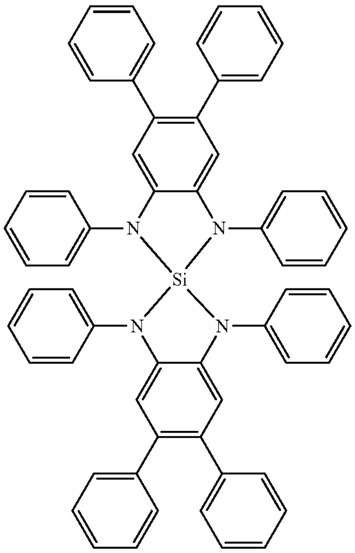
(19)
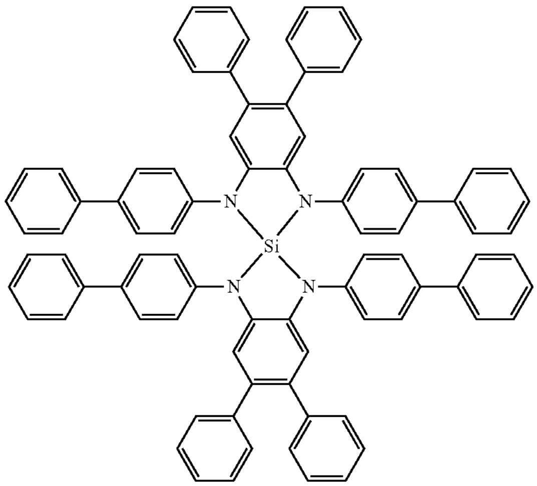

-continued
(20)
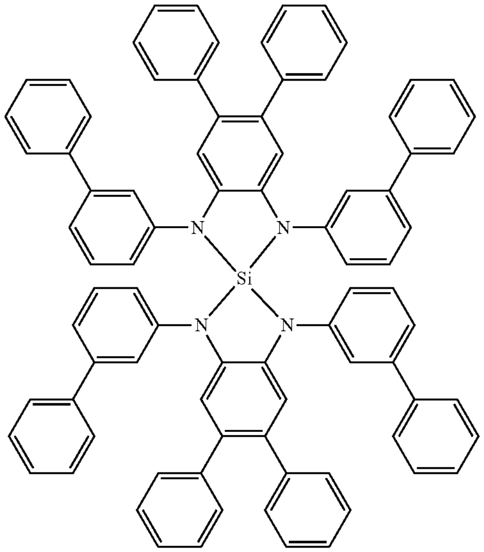
(21)
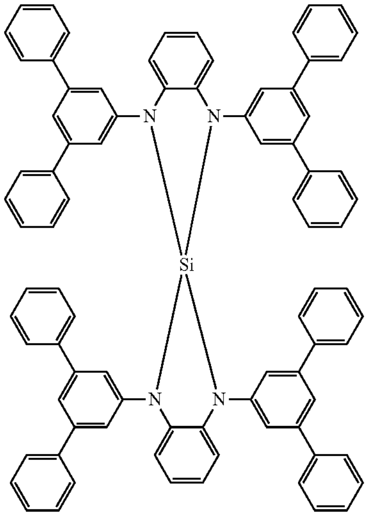
(22)
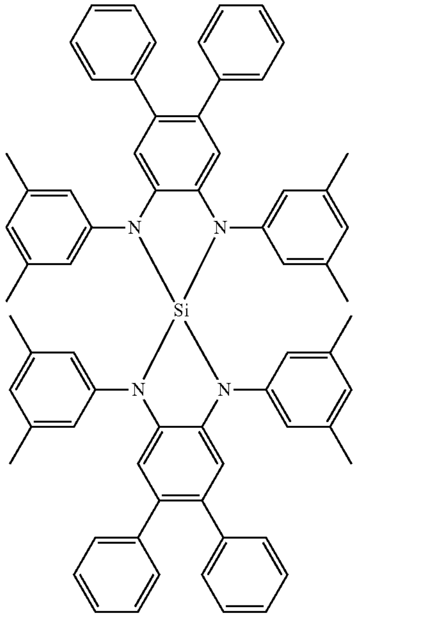
-continued
(23)
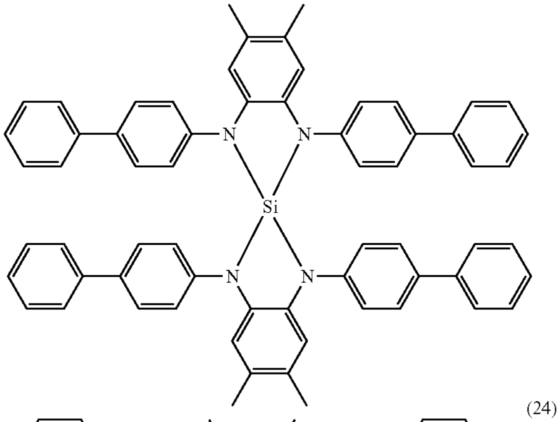
(24)
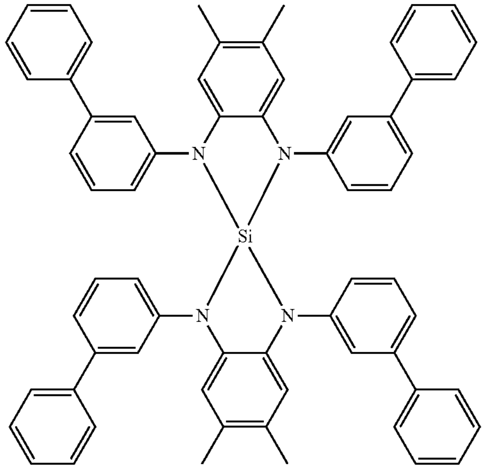
(25)
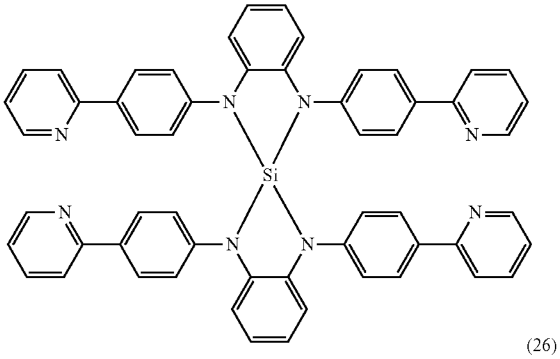
(26)
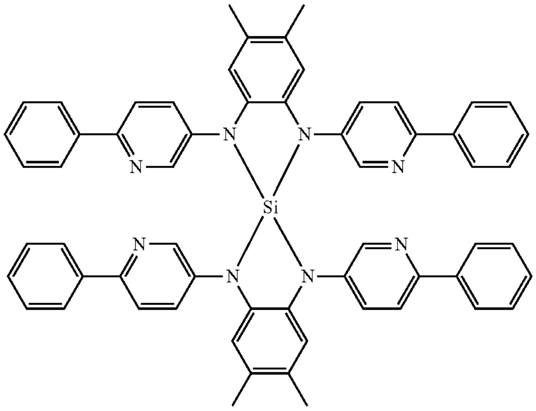

-continued
(27)
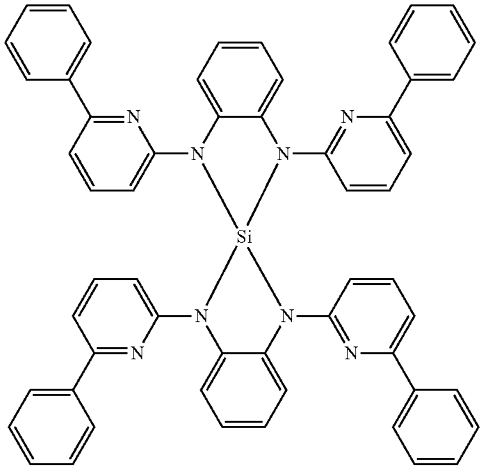
(28)
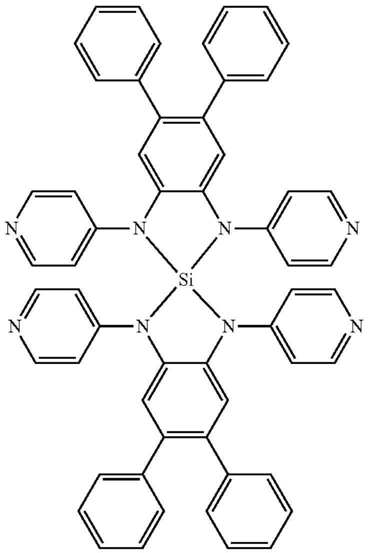
(29)
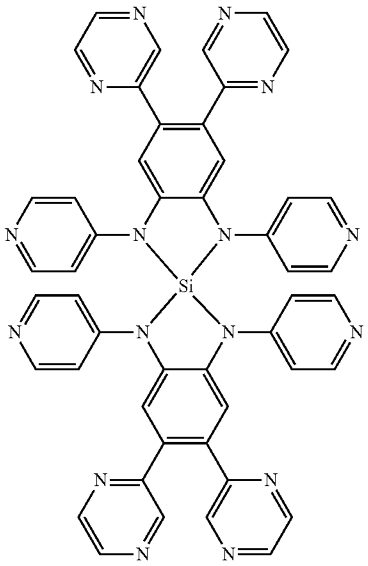
-continued
(30)
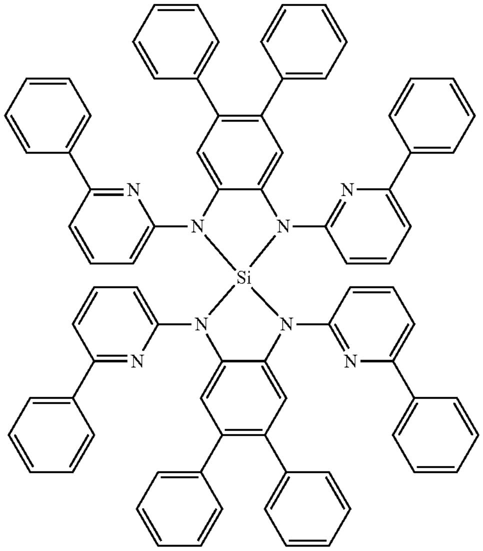
(31)
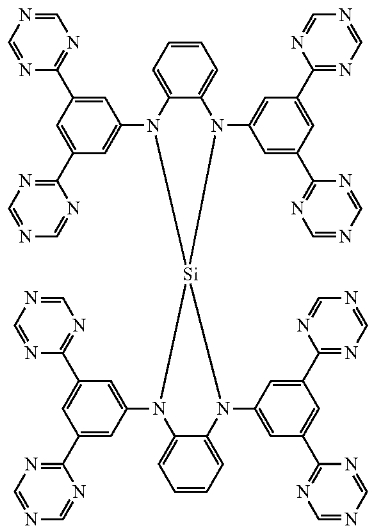
(32)
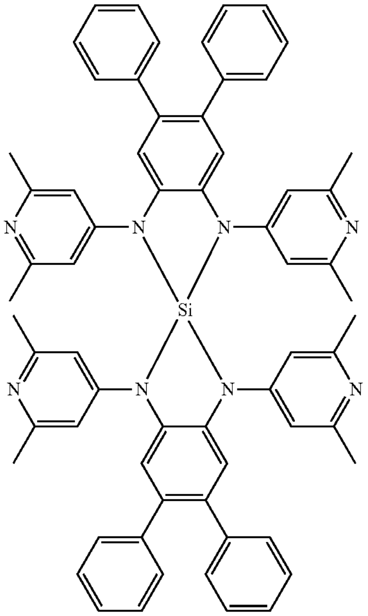

-continued
(33)
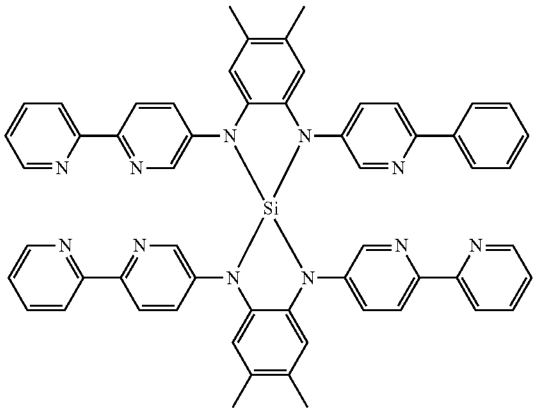
(34)
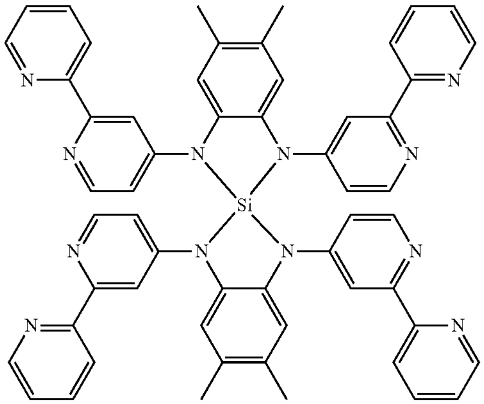
(35)
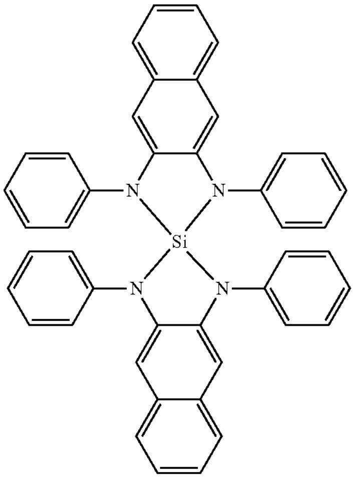
-continued
(36)
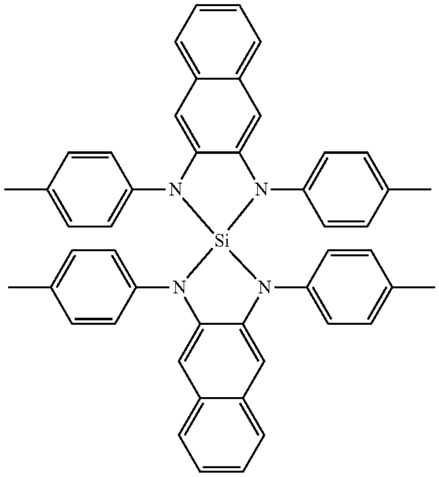
(37)
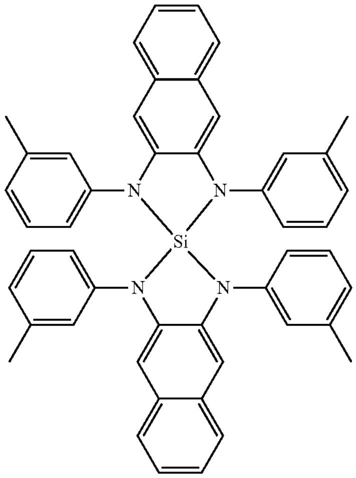
(38)
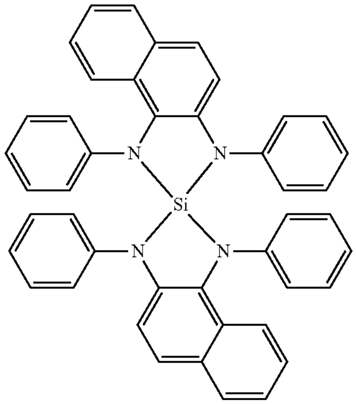

-continued
(39)
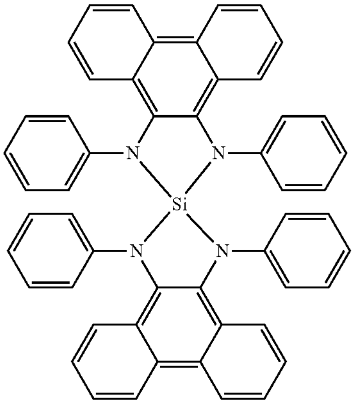
(40)
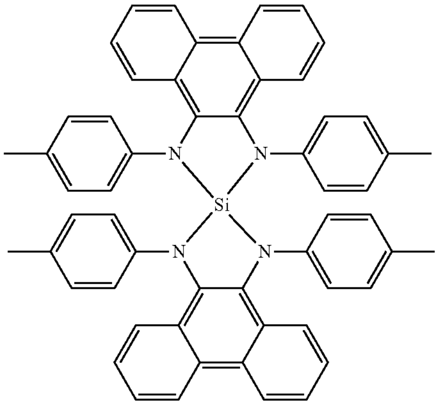
(41)
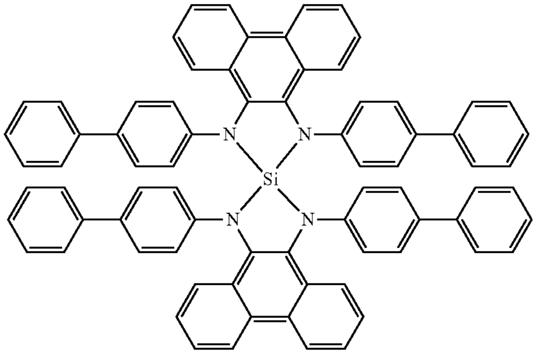
(42)
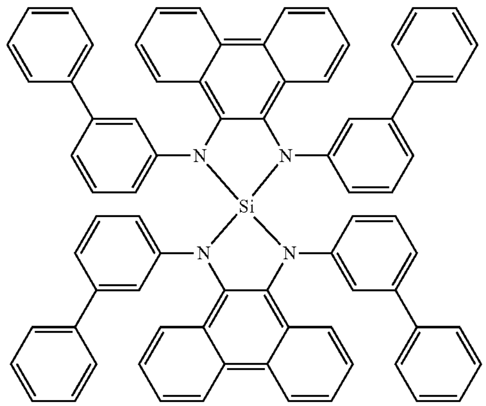
-continued
(43)
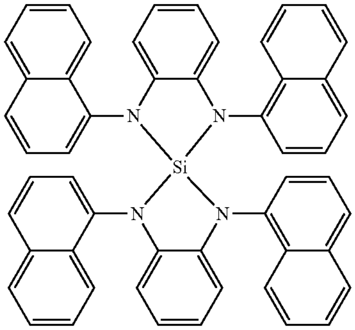
(44)
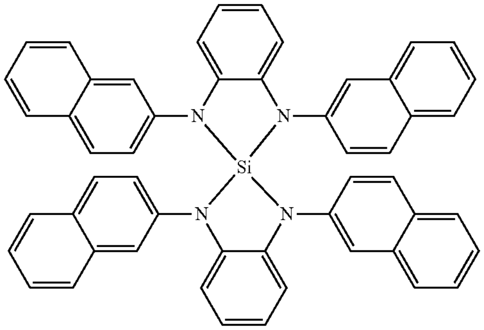
(45)
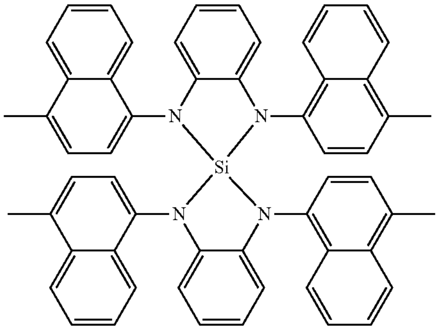
(46)
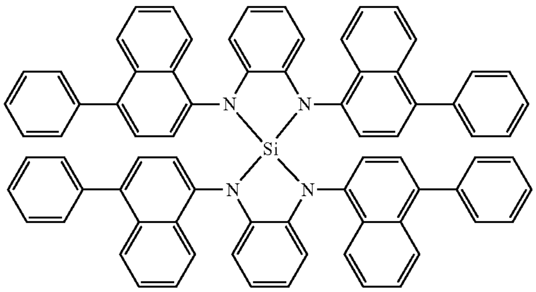
(47)
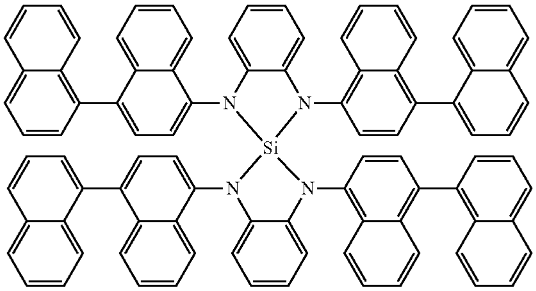

-continued
(48)
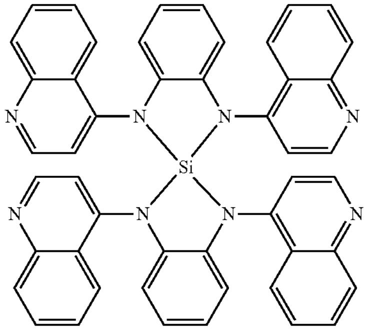
(49)
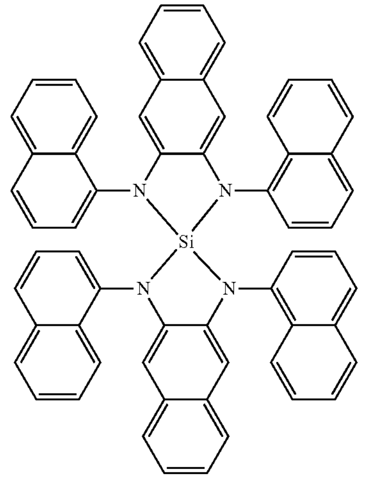
(50)
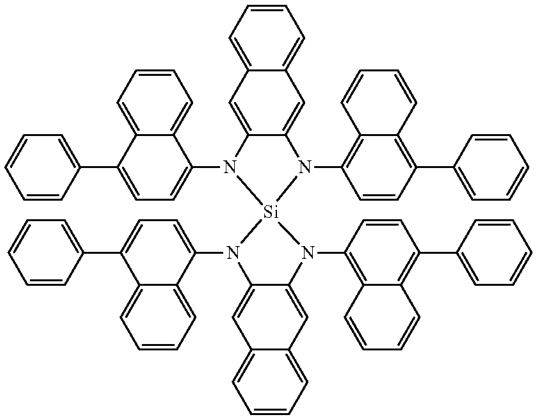
(51)
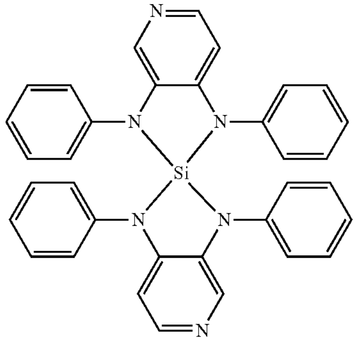
-continued
(52)
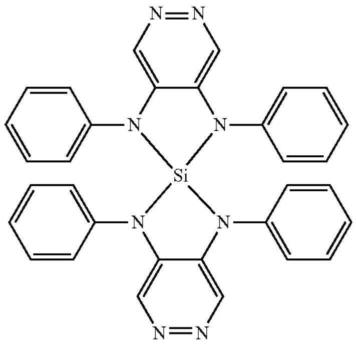
(53)
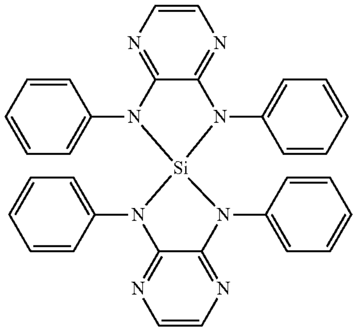
(54)
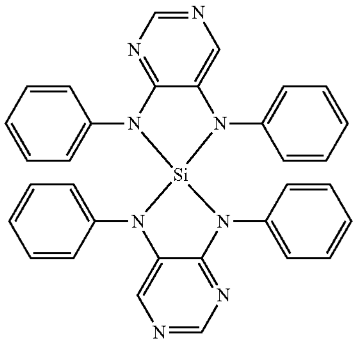
(55)
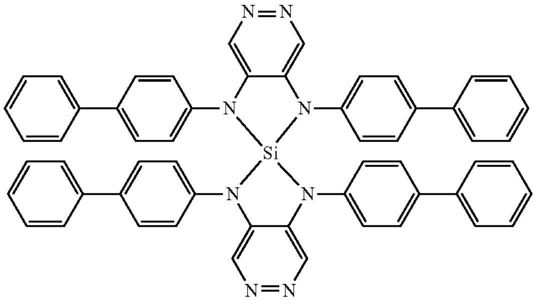

-continued
(56)
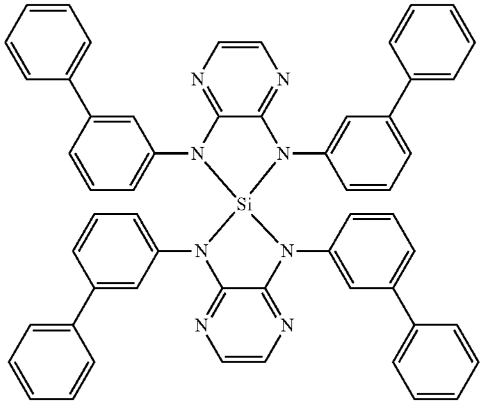
(57)
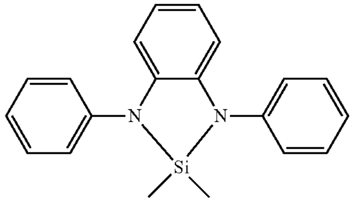
(58)
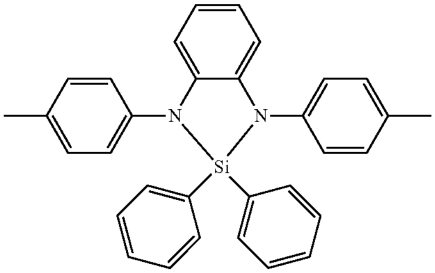
(59)
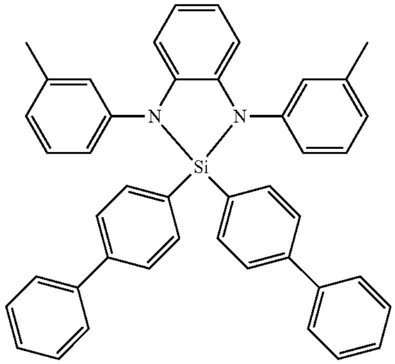
(60)
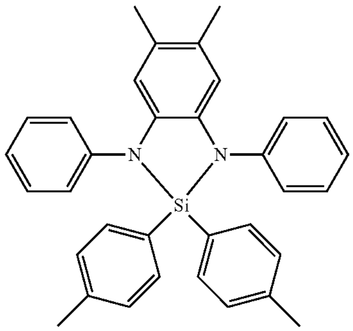
-continued
(61)
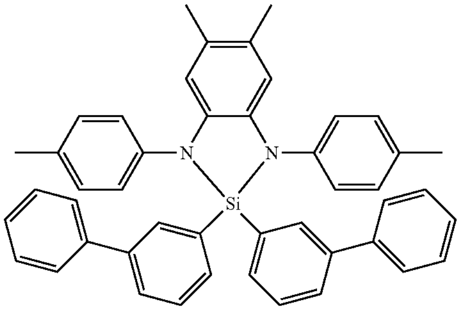
(62)
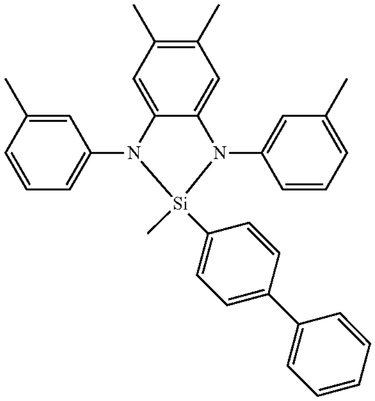
(63)
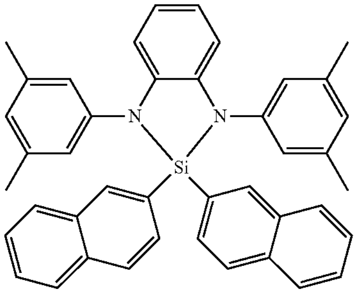
(64)
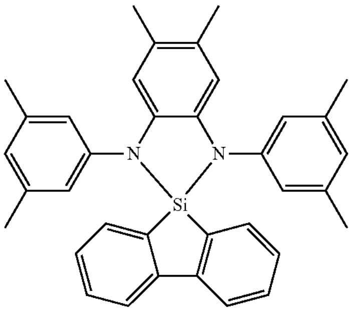

-continued
(65)
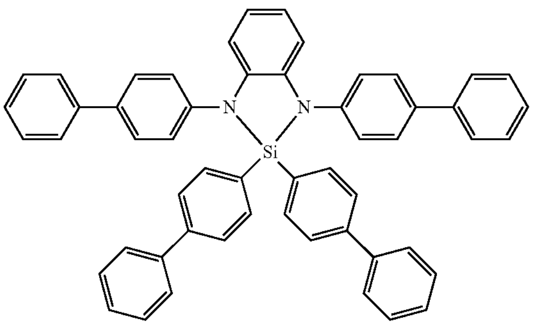
(66)
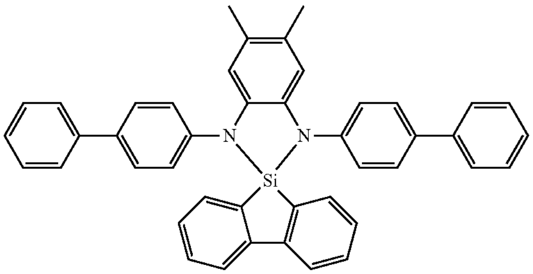
(67)
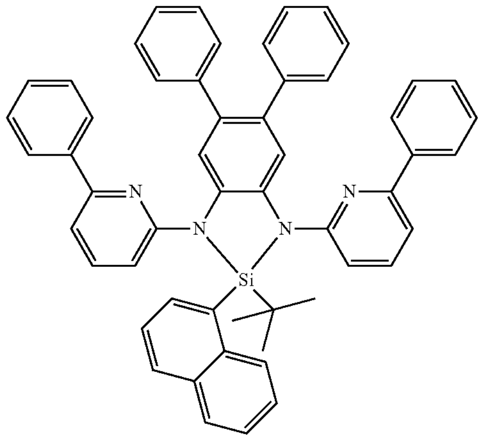
(68)
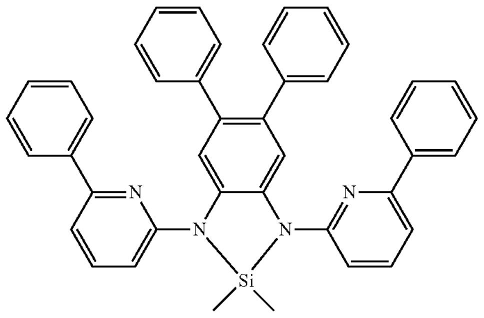
(69)
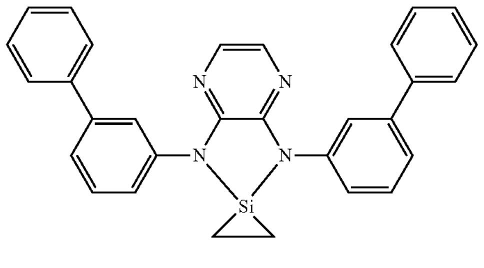
-continued
(70)
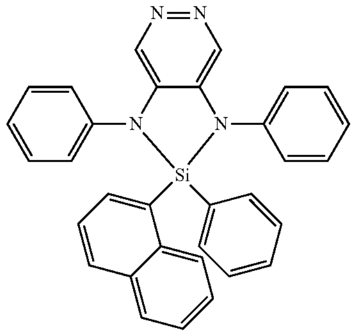
(71)
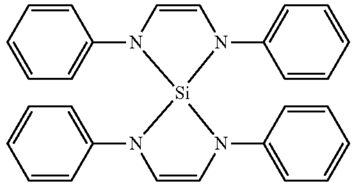
(72)
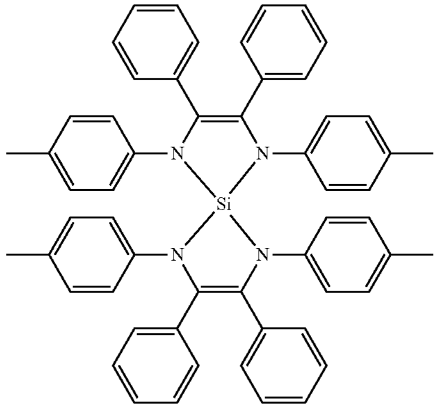
(73)
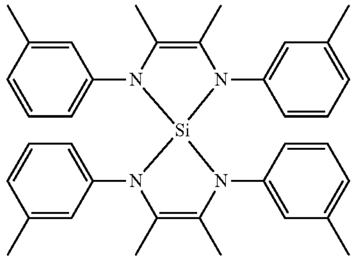
(74)
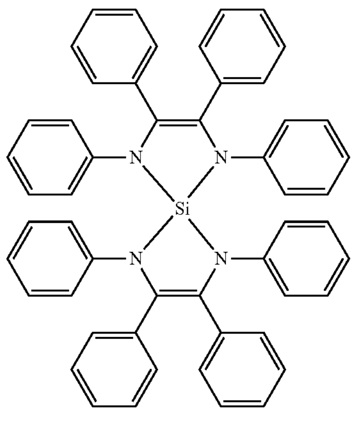

-continued
(75)
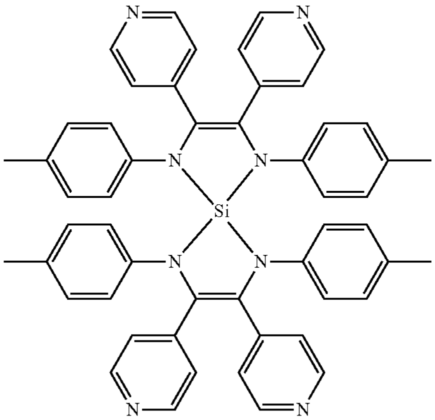
(76)
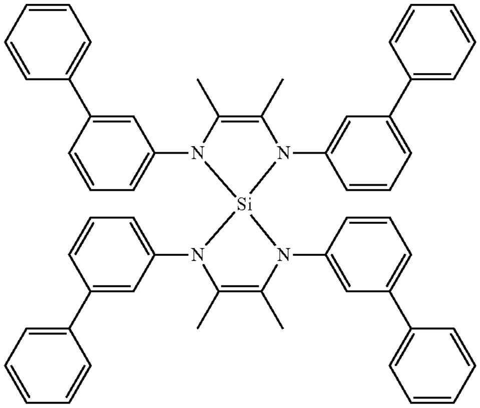
(77)
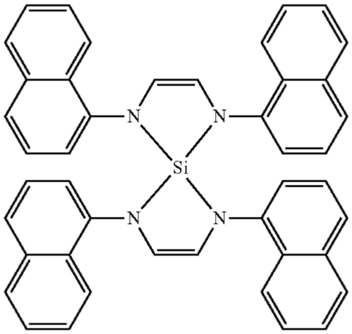
(78)
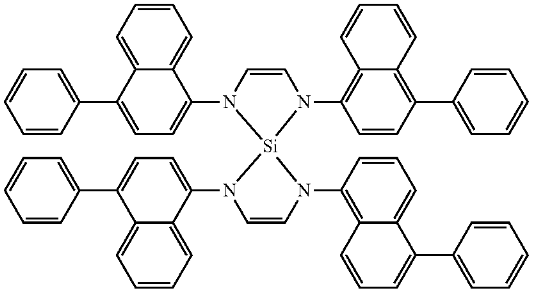
-continued
(79)
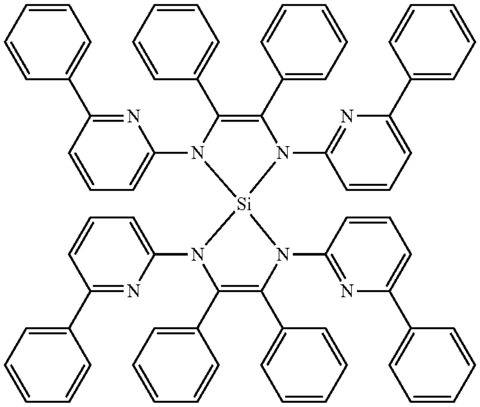
(80)
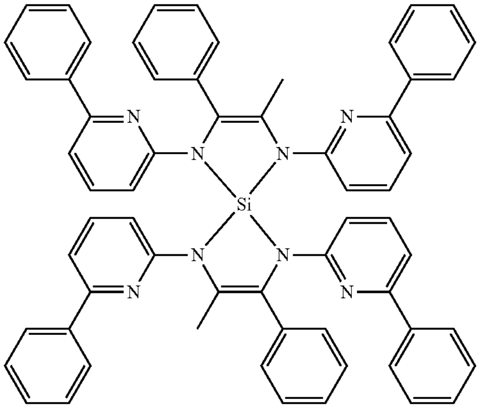
(82)
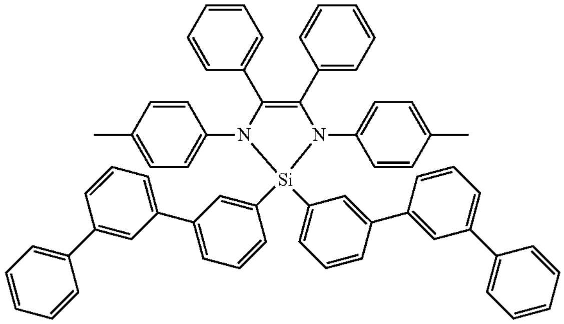
(83)
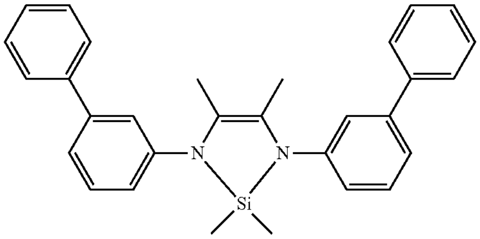

-continued
(84)
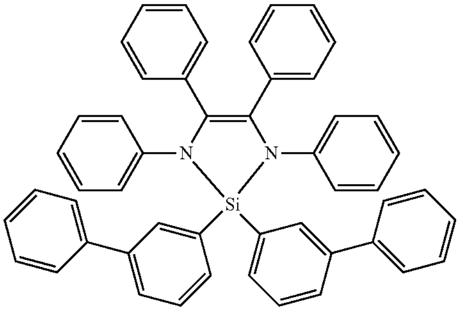
(85)
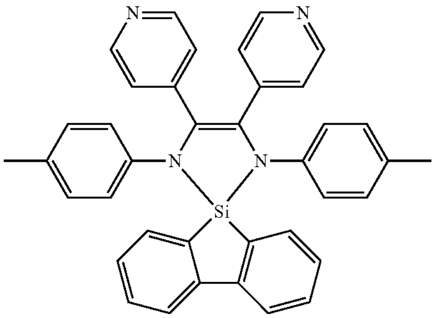
(86)
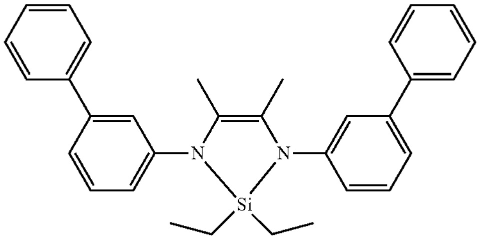
(87)
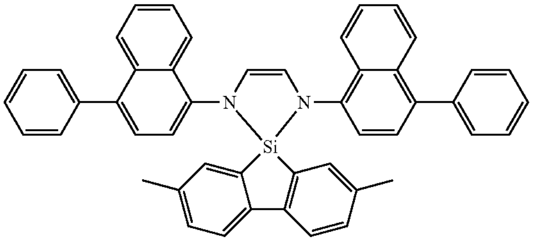
(88)
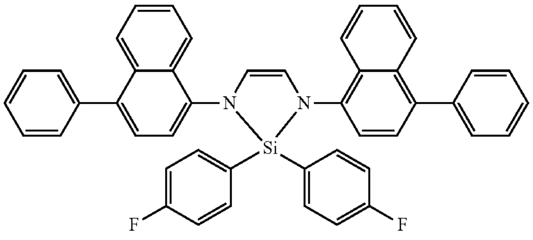
-continued
(89)
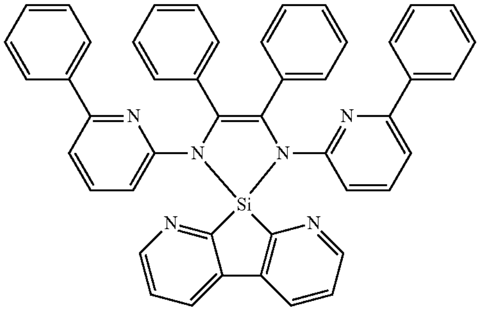
(90)
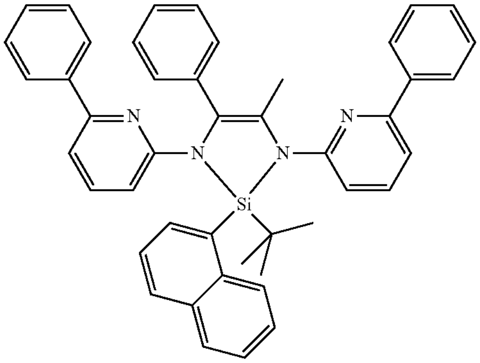
(91)
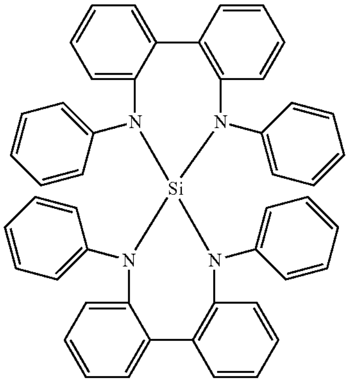
(92)
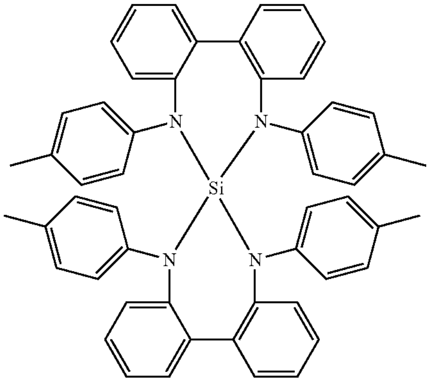

-continued
(93)
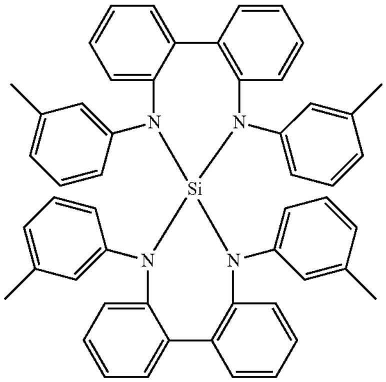
(94)
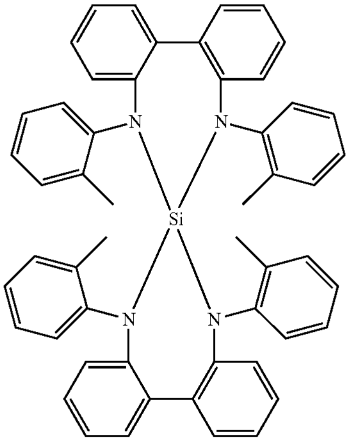
(95)
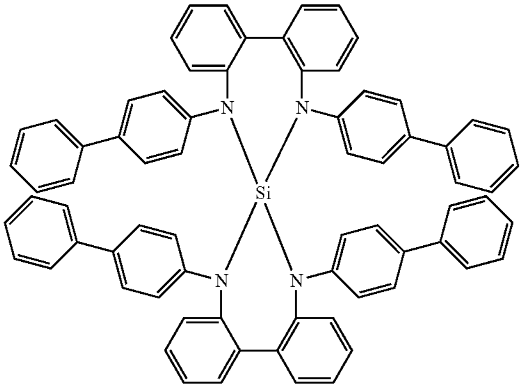
-continued
(96)
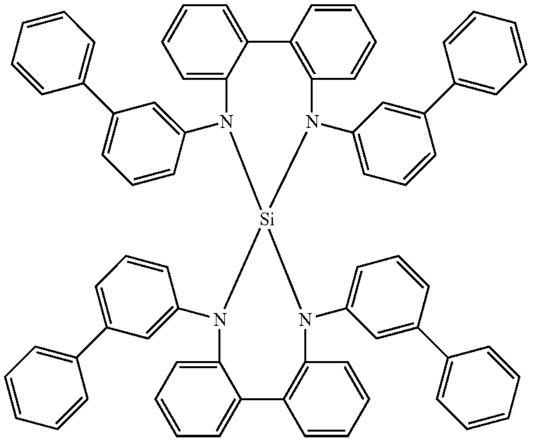
(97)
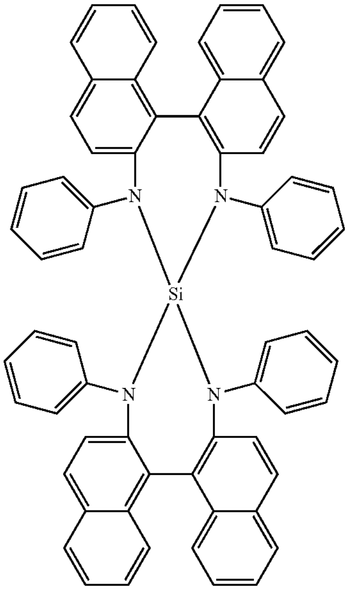
(98)
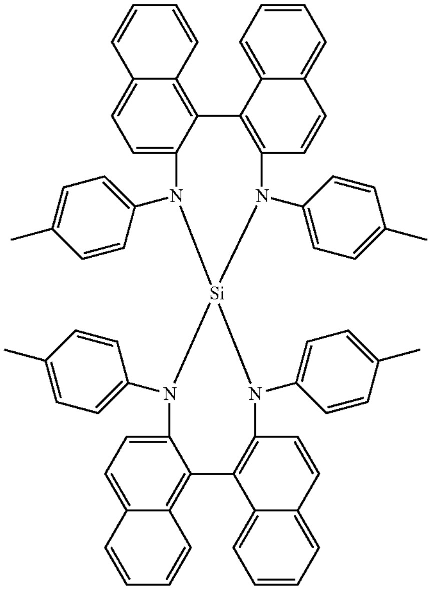

-continued
(99)
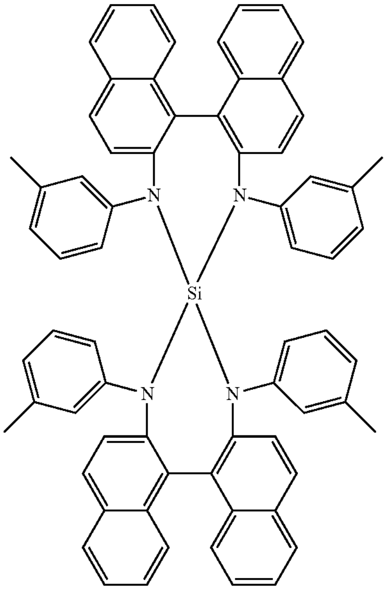
(100)
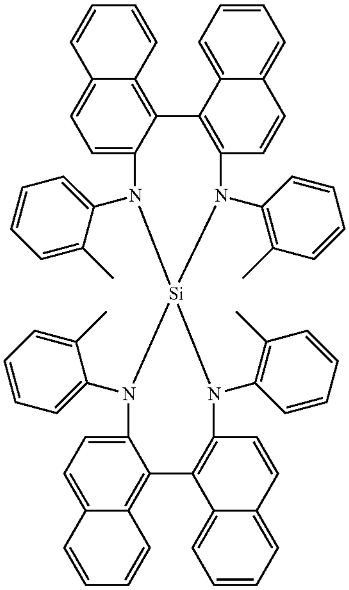
(101)
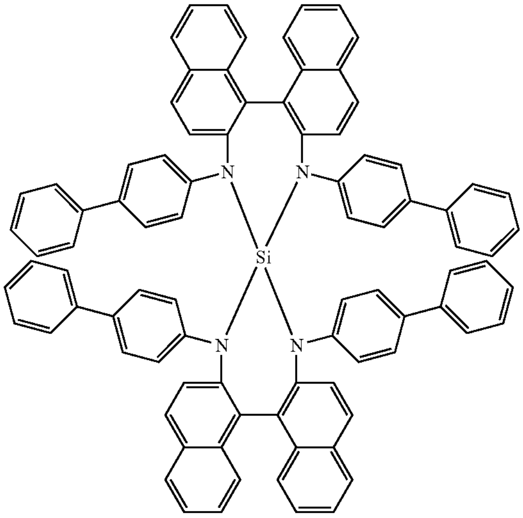
-continued
(102)
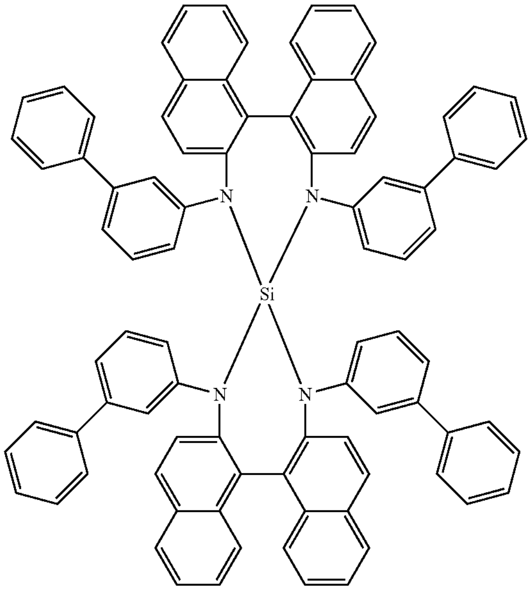
(103)
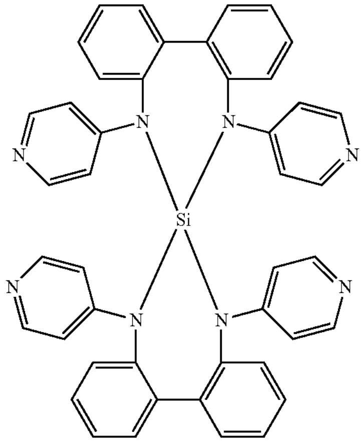
(104)
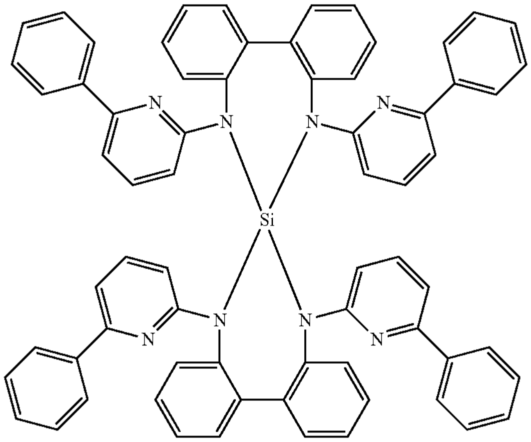

-continued
(105)
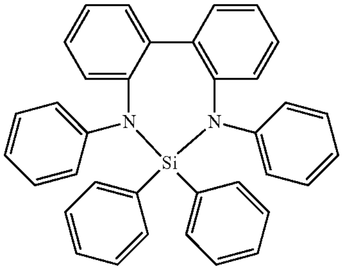
(107)
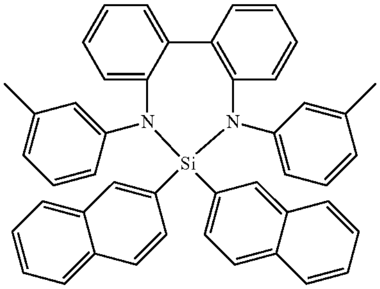
(108)
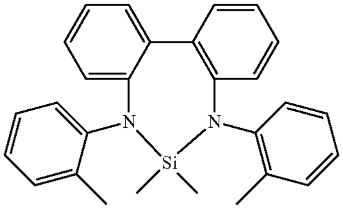
(110)
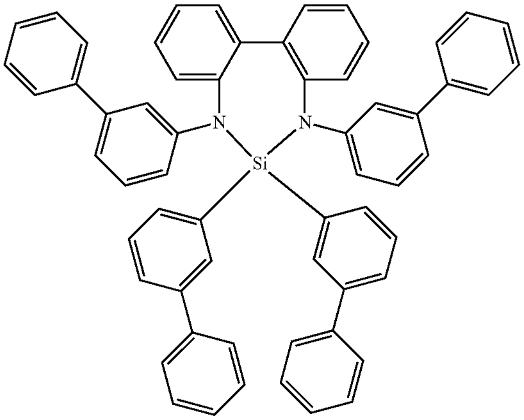
(111)
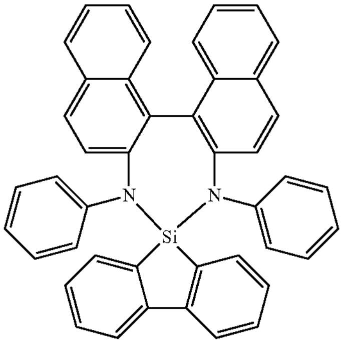
-continued
(113)
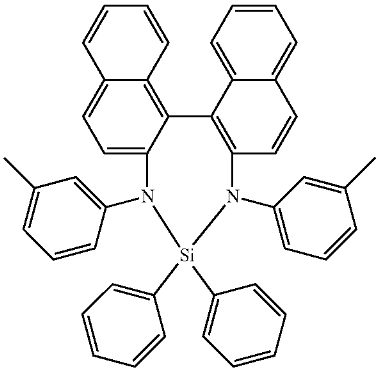
(114)
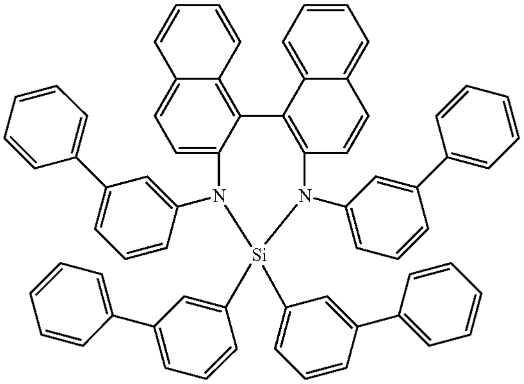
(115)
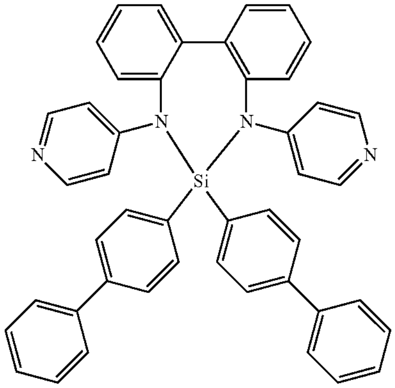
(116)
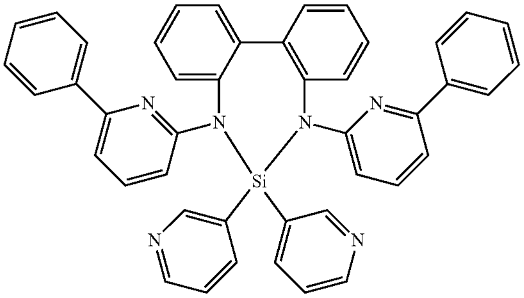

-continued
(117)
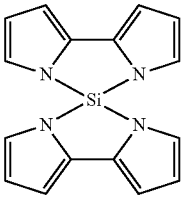
(118)
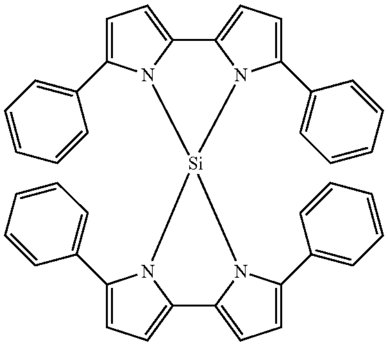
(119)
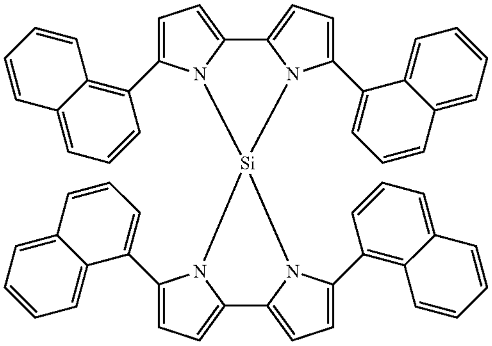
(120)
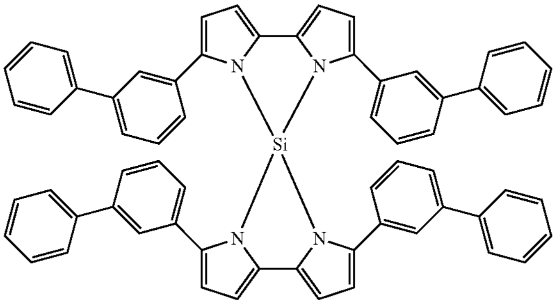
(121)
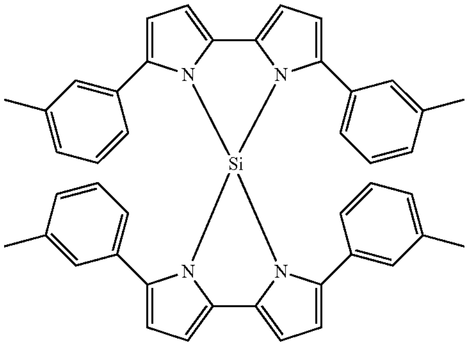
-continued
(122)
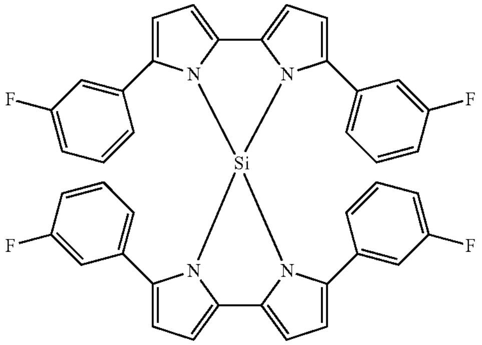
(123)
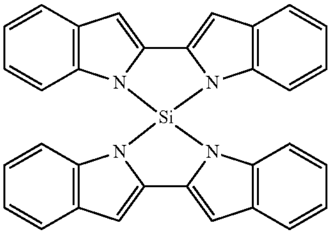
(124)
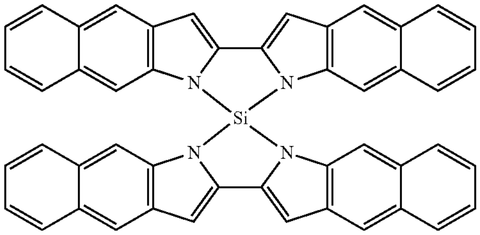
(125)
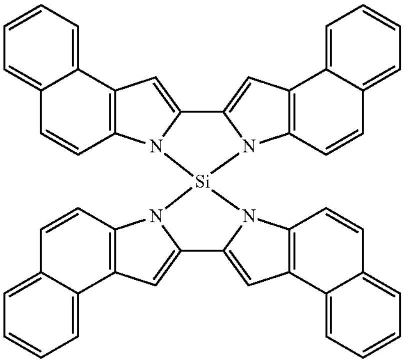
(126)
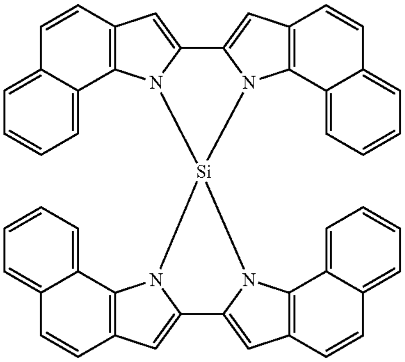

-continued
(127)
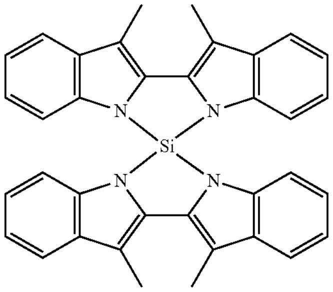
(128)
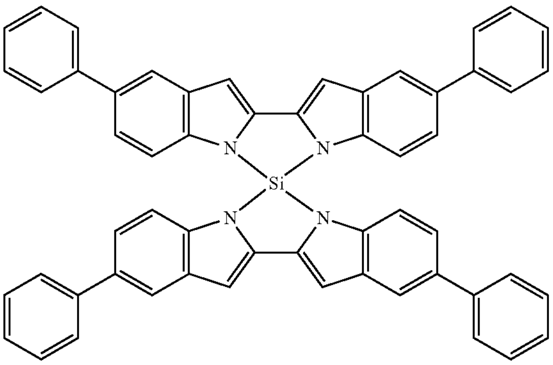
(129)
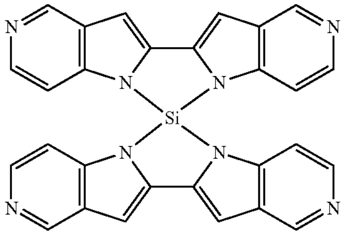
(130)
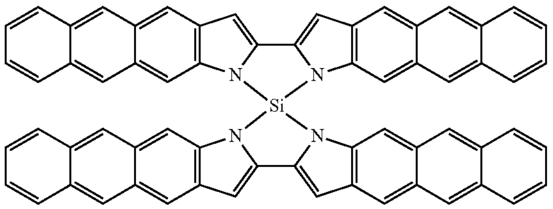
(131)
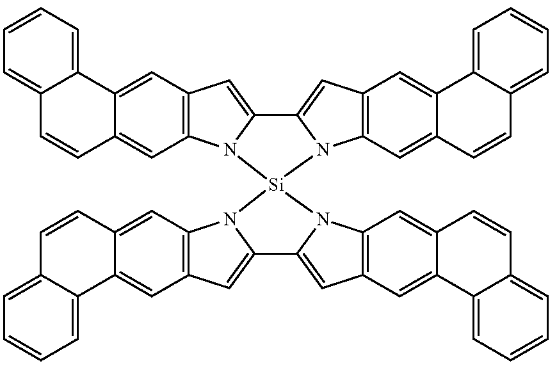
-continued
(132)
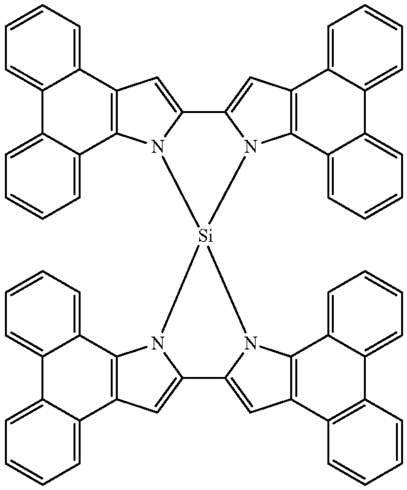
(133)
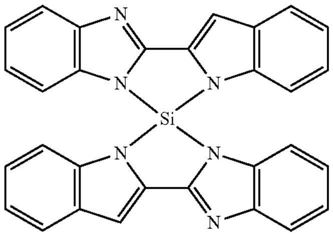
(134)
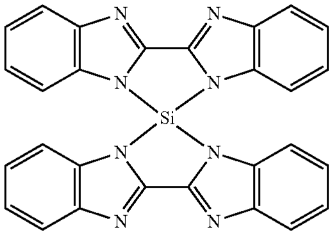
(135)
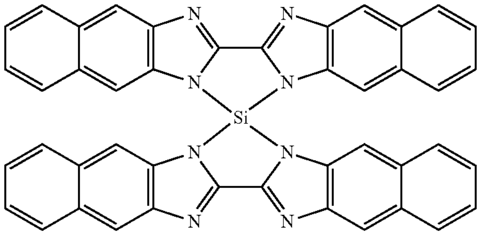
(136)
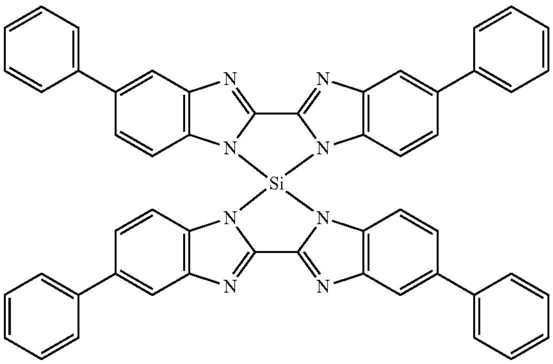

-continued
(137)
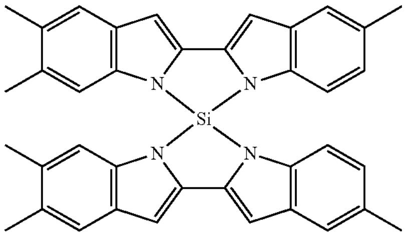
(138)
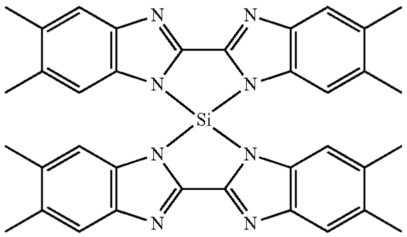
(139)
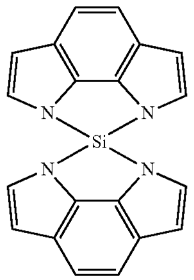
(140)
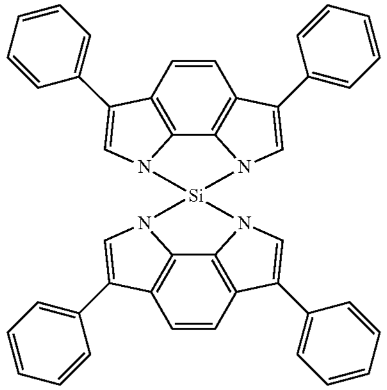
(141)
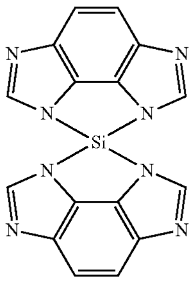
-continued
(142)
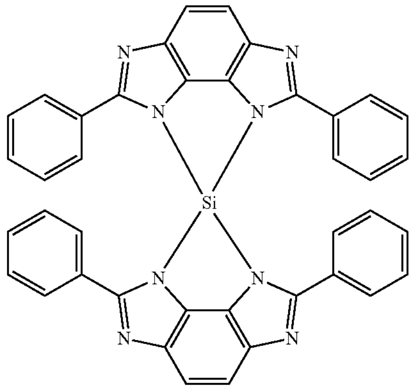
(143)
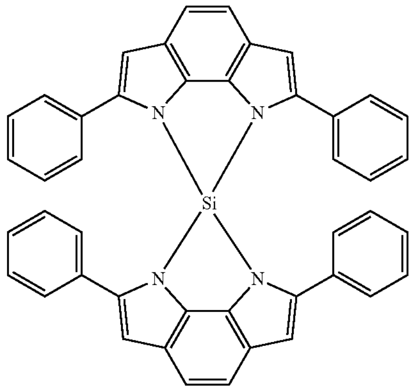
(144)
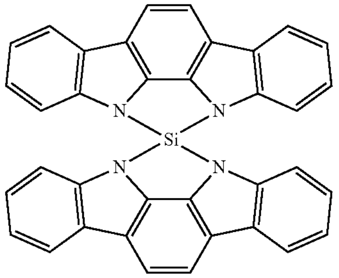
(145)
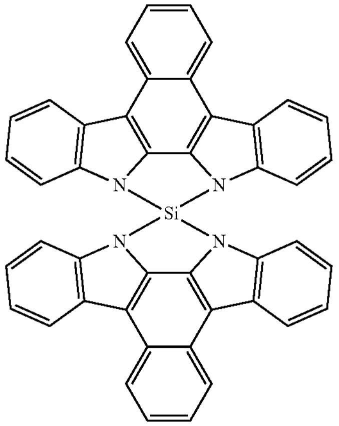

-continued
(146)
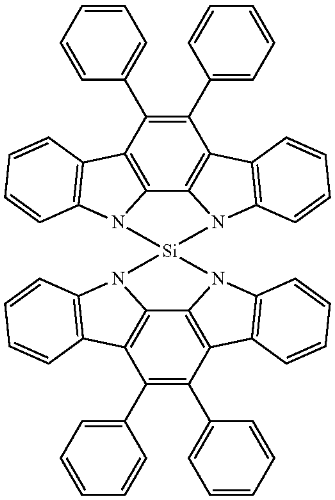
(147)
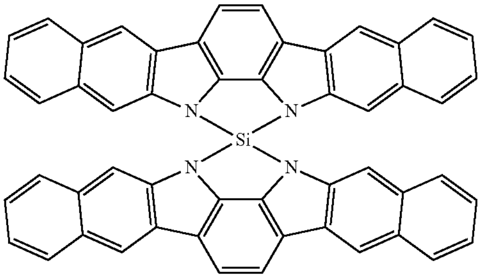
(148)
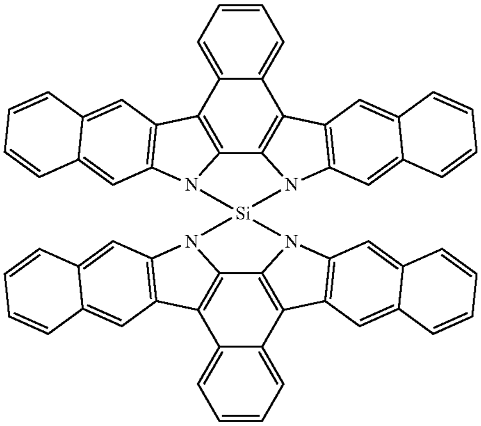
(149)
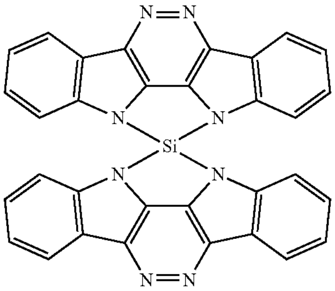
-continued
(150)
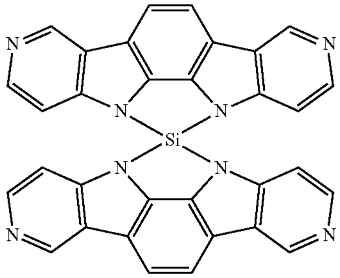
(151)
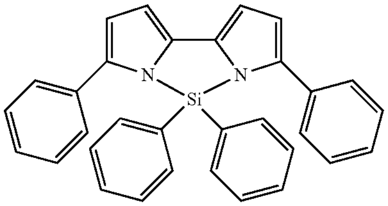
(152)
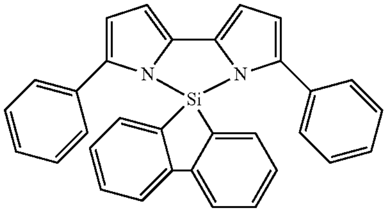
(153)
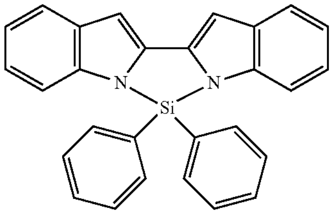
(154)
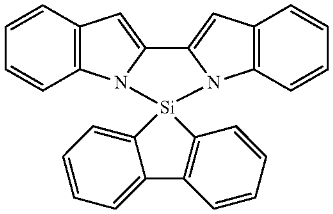
(155)
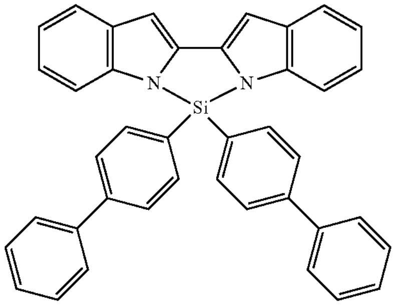

-continued
(156)
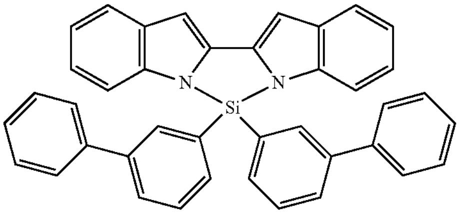
(157)
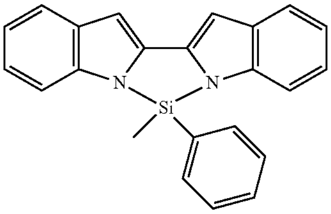
(158)
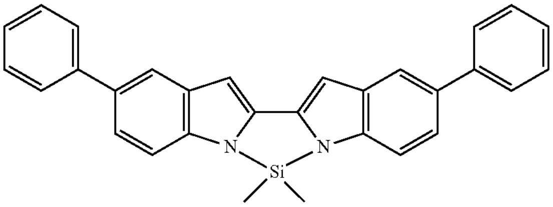
(159)
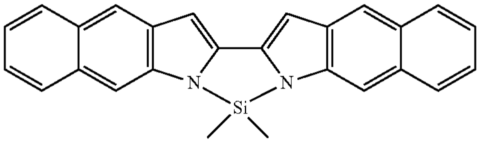
(160)
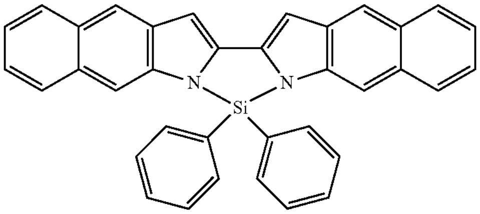
(161)
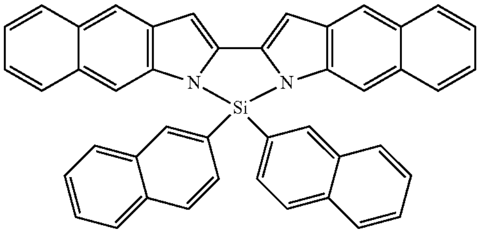
(162)
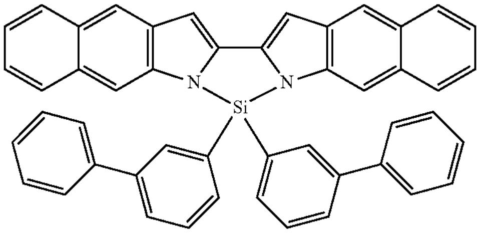
-continued
(163)
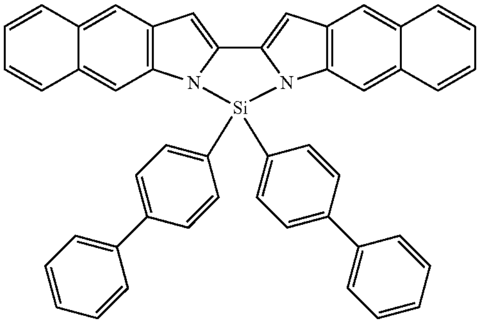
(164)
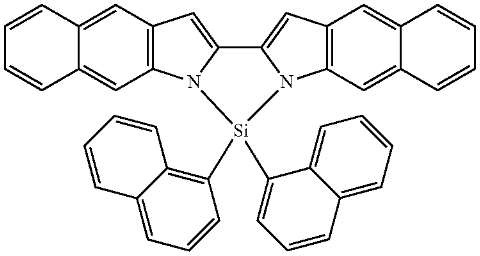
(165)
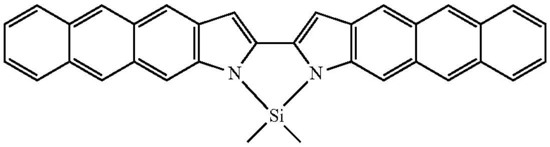
(166)
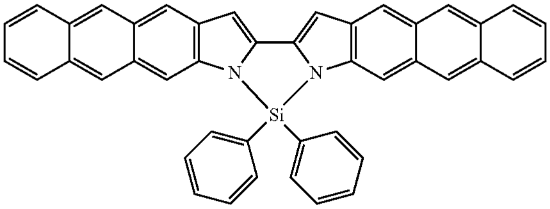
(167)
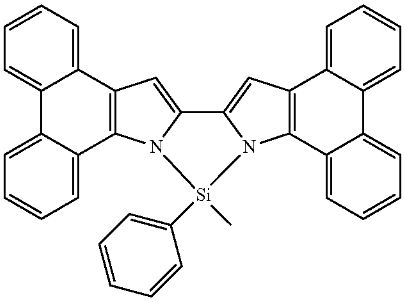
(168)
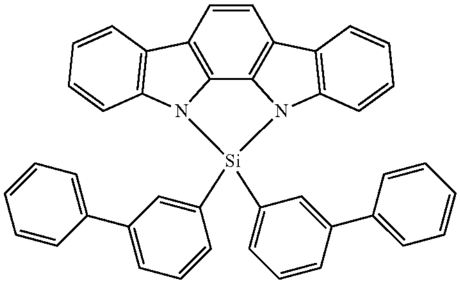

-continued
(169)
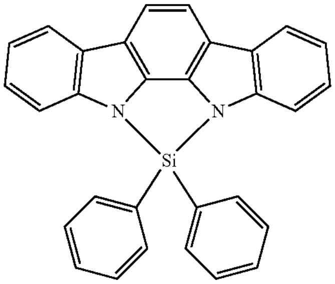
(170)
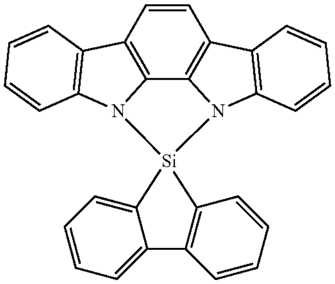
(171)
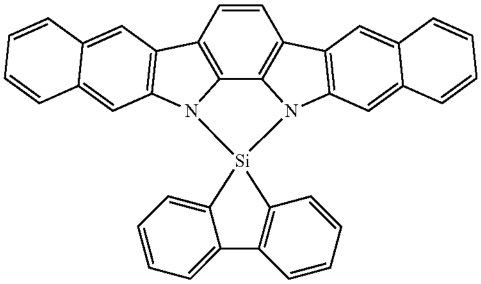
(172)
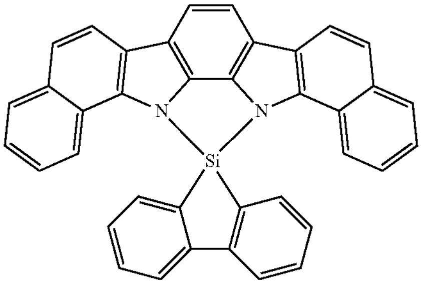
(173)
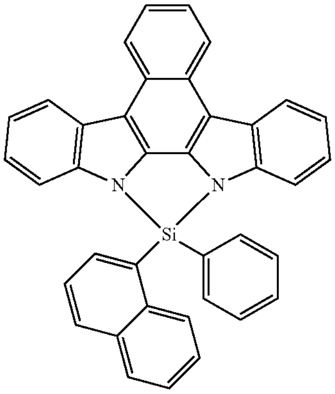
-continued
(174)
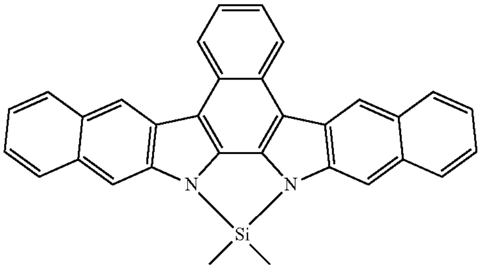
(175)
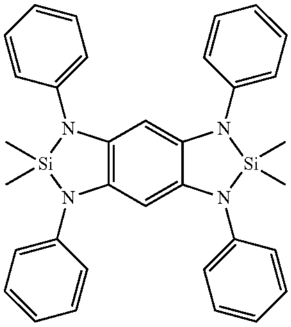
(176)
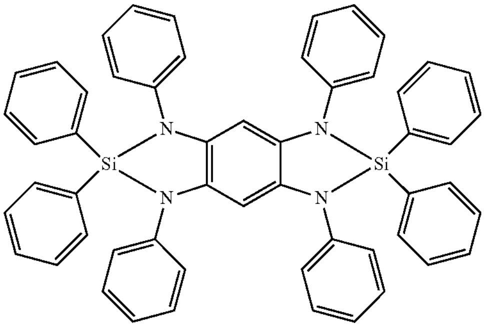
(177)
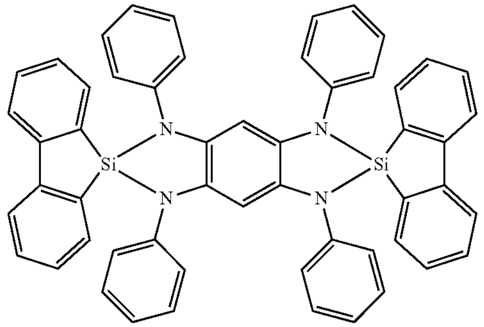
(178)
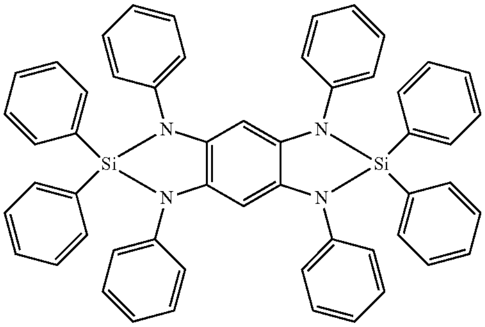

-continued
(179)
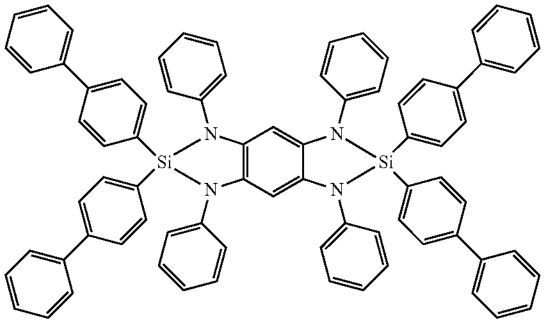
(180)
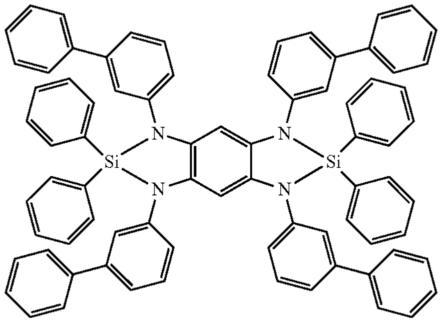
(181)
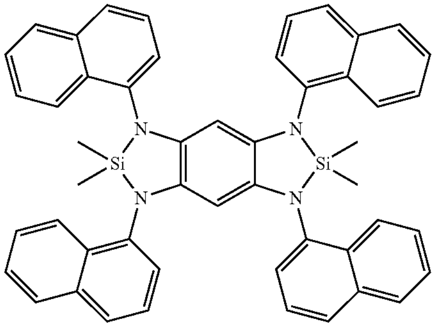
(182)
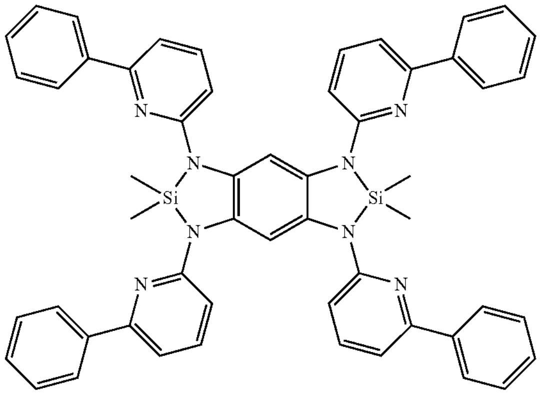
-continued
(183)
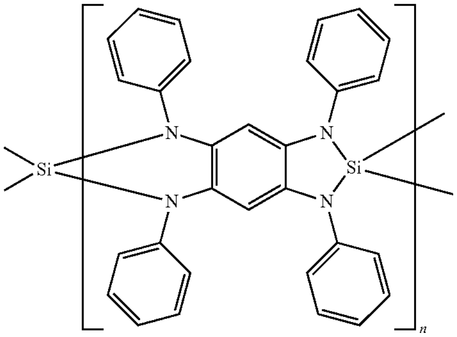
(184)
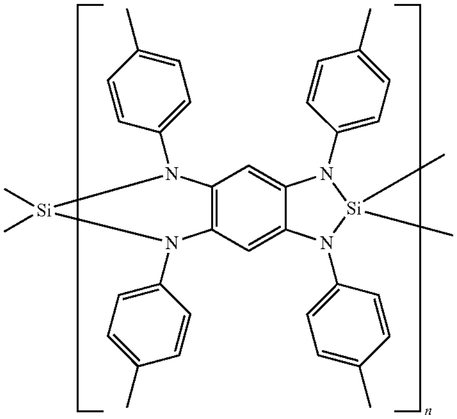
(185)
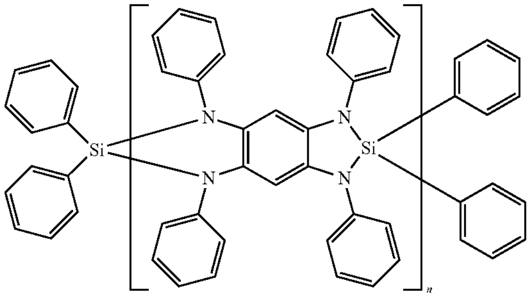
(186)
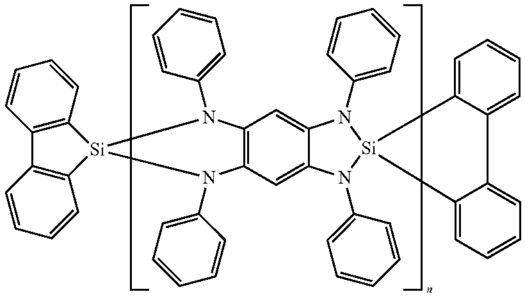

-continued
(187)
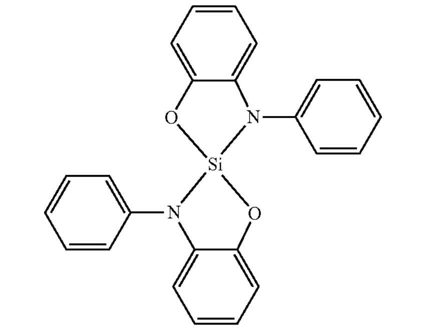
(188)
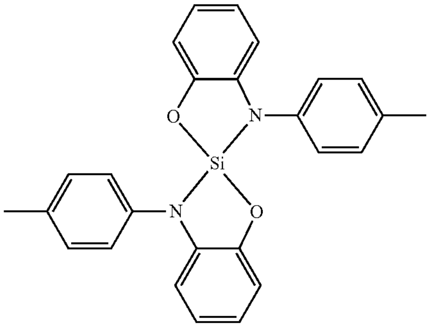
(189)
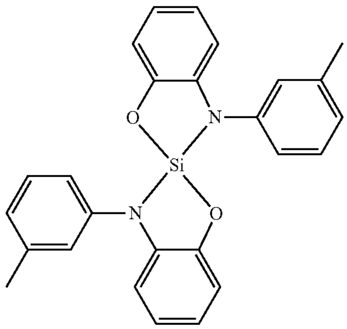
(190)
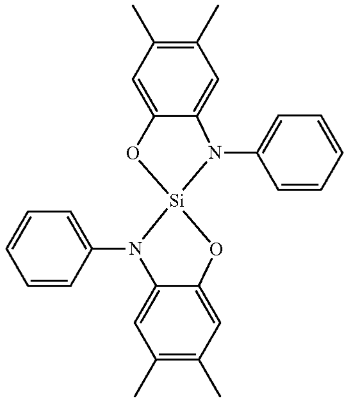
-continued
(191)
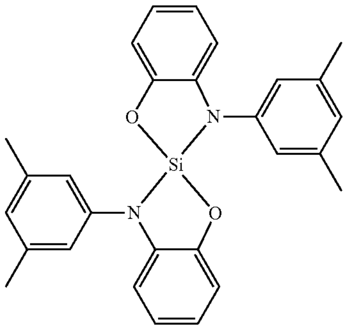
(192)
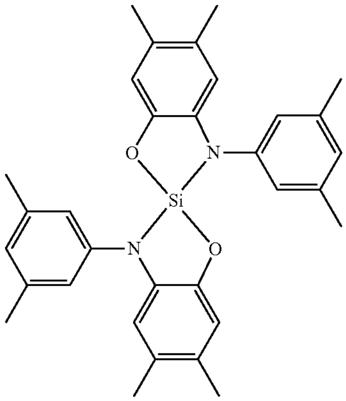
(193)
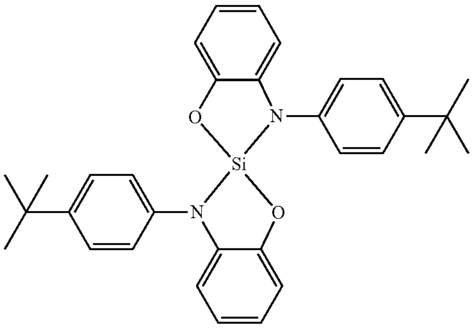
(194)
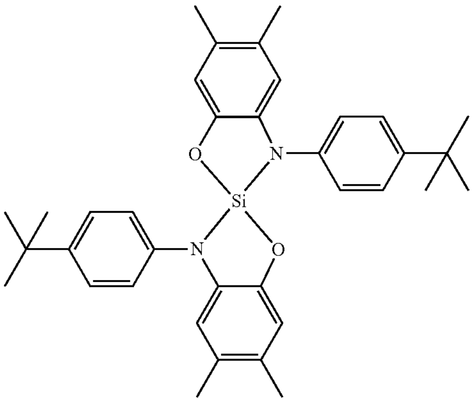

-continued
(195)
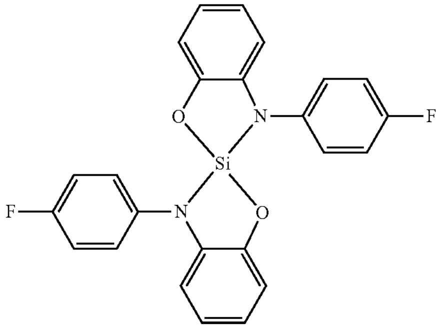
(196)
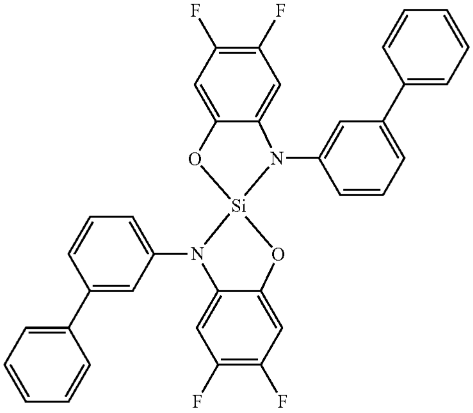
(197)
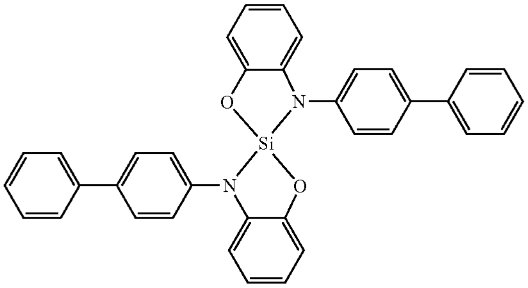
(198)
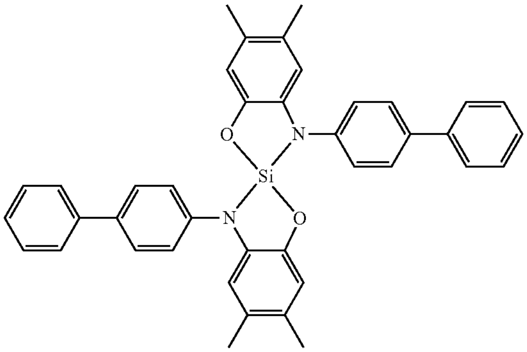
-continued
(199)
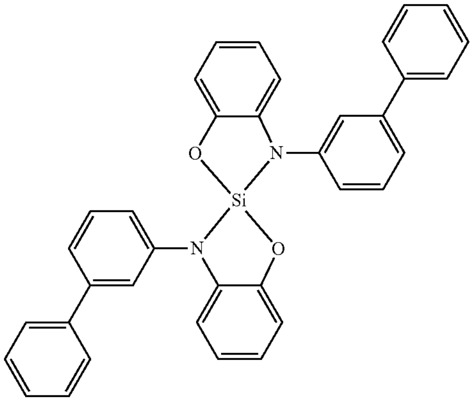
(200)
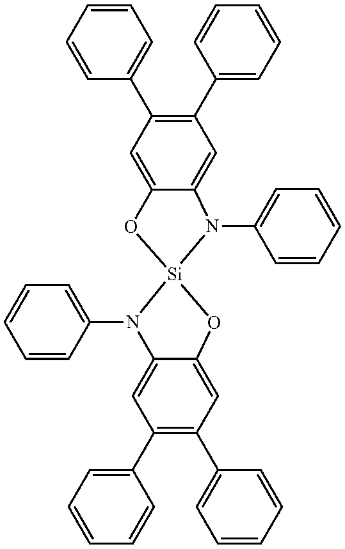
(201)
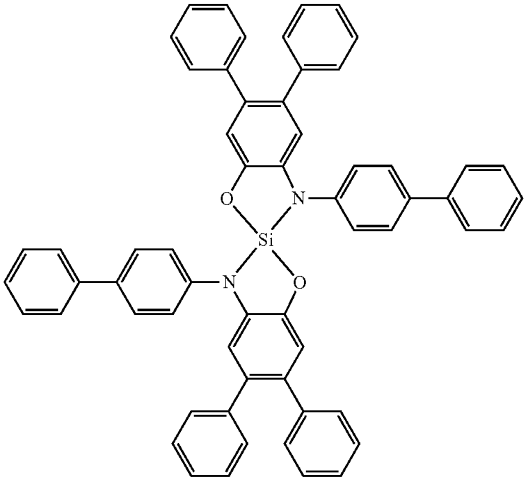

-continued
(202)
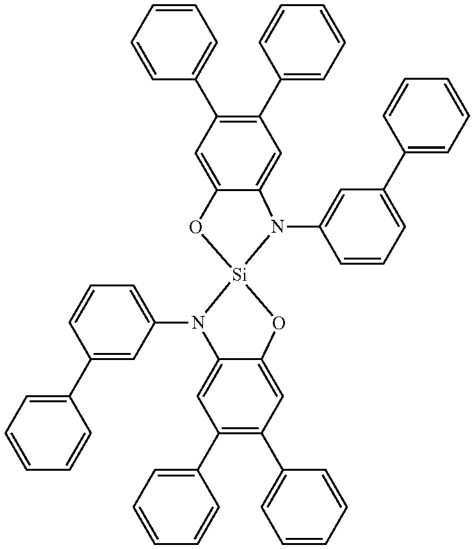
(203)
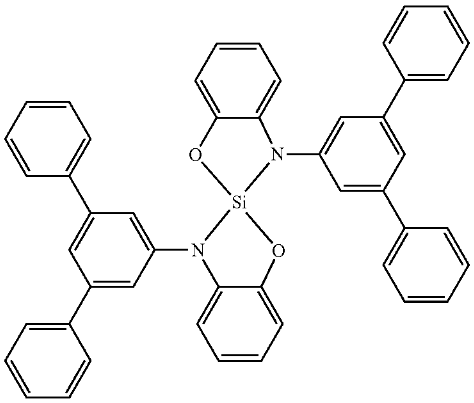
(204)
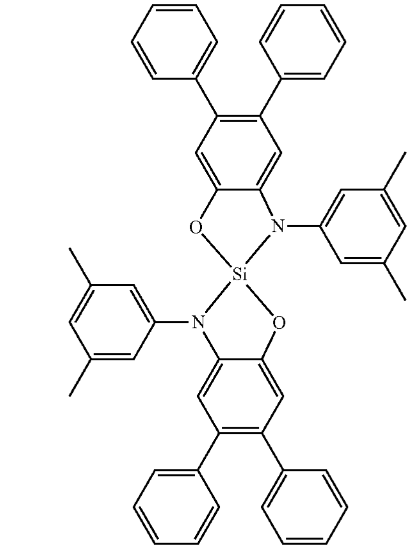
-continued
(205)
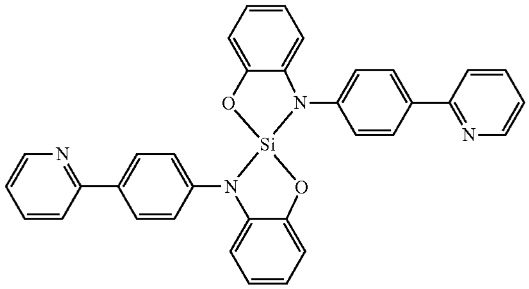
(206)
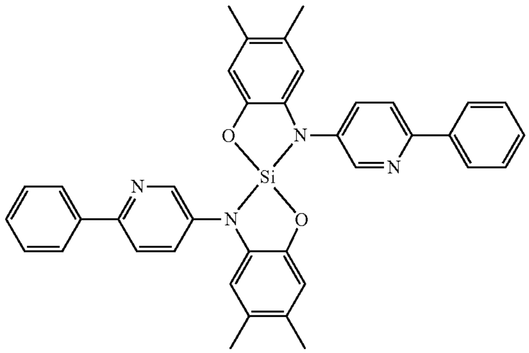
(207)
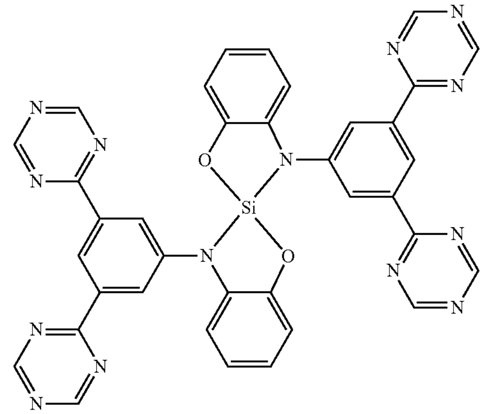
(208)
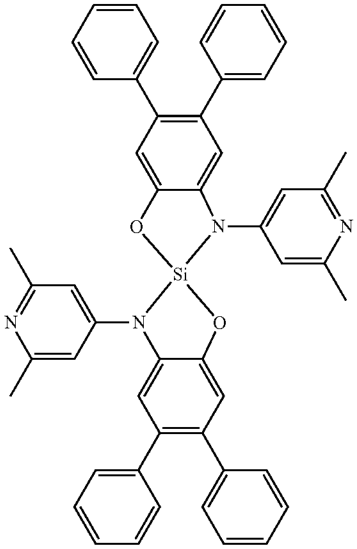

-continued
(209)
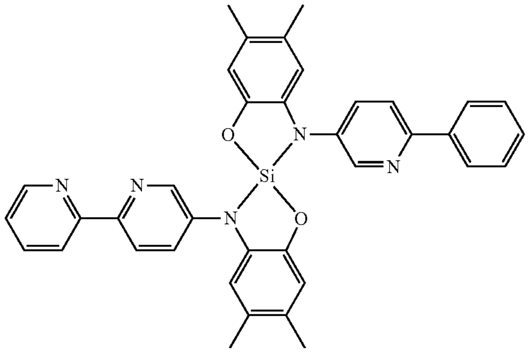
(210)
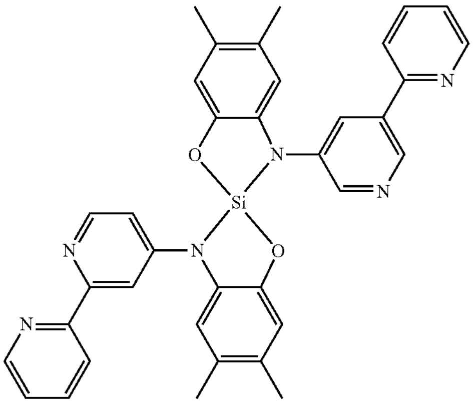
(211)
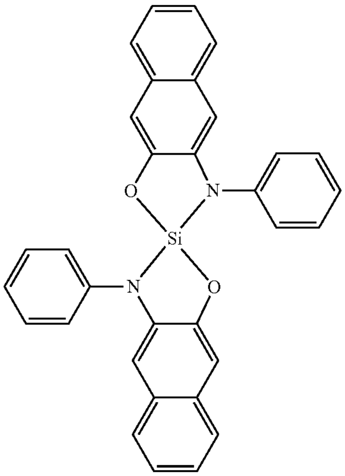
-continued
(212)
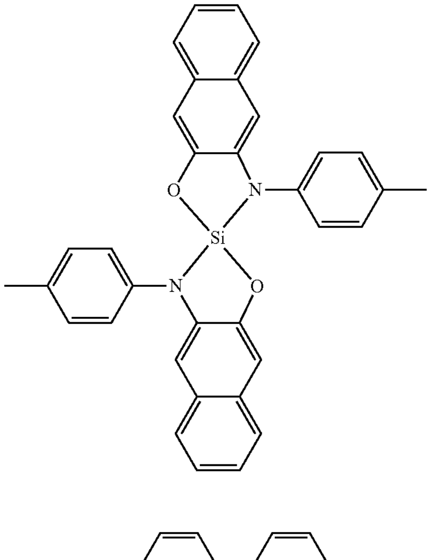
(213)
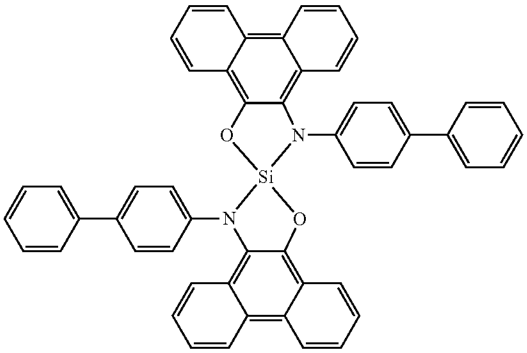
(214)
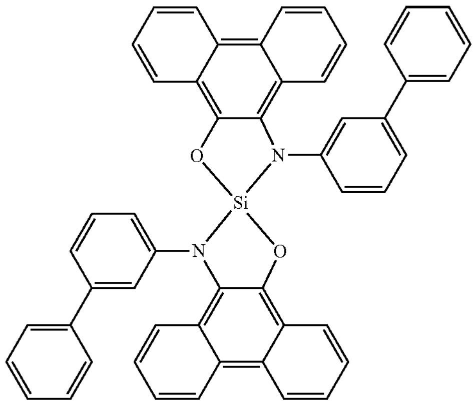
(215)
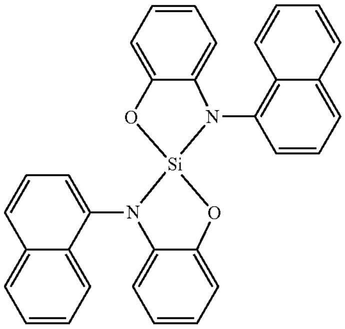

-continued
(216)
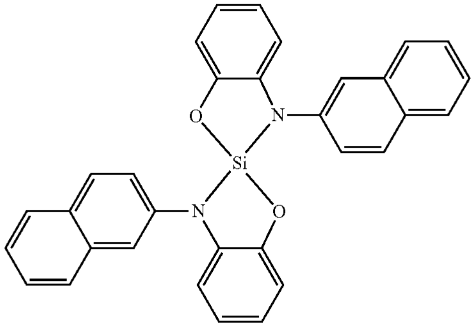
(217)
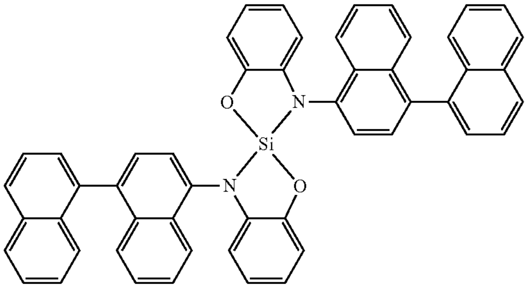
(218)
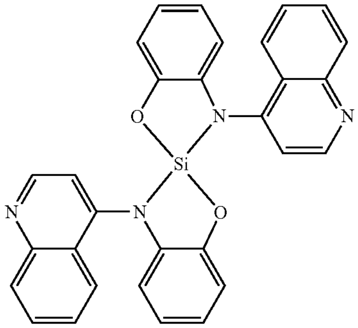
(219)
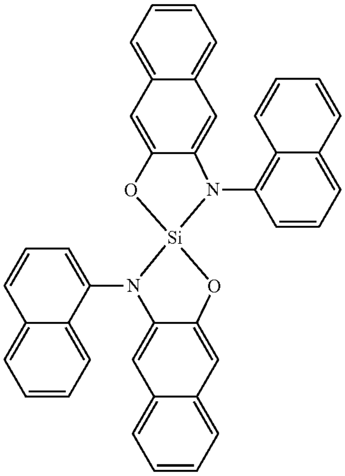
-continued
(220)
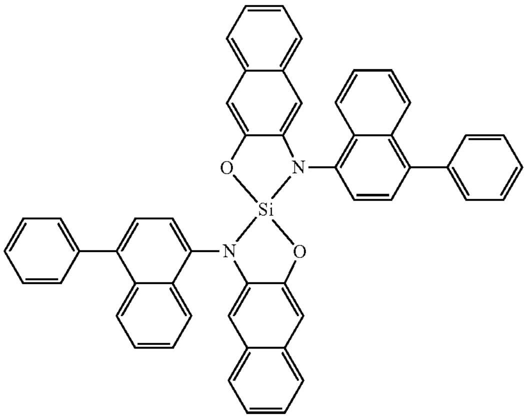
(221)
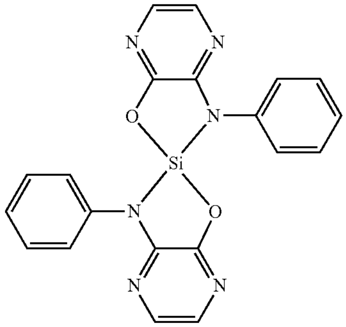
(222)
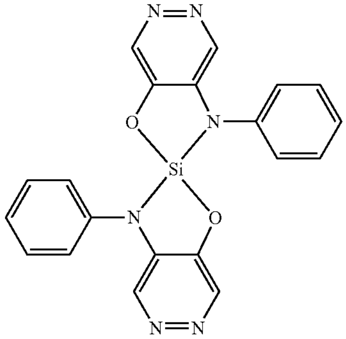
(223)
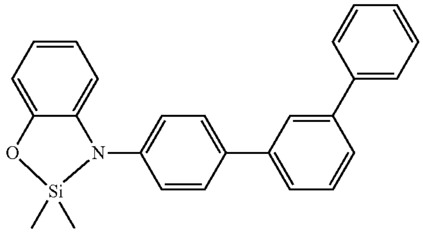
(224)
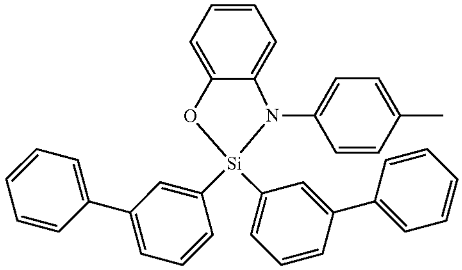

-continued
(225)
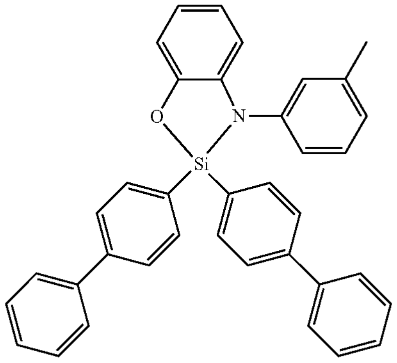
(226)
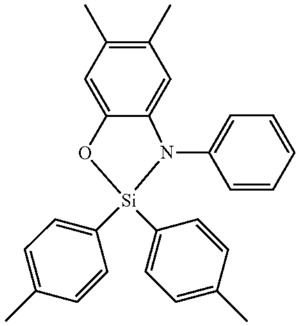
(227)
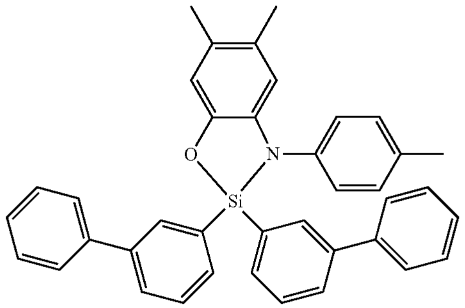
(228)
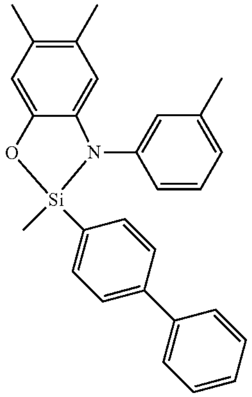
-continued
(229)
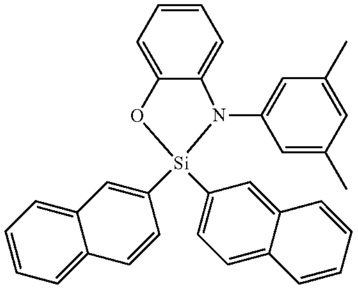
(230)
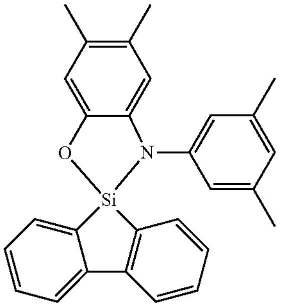
(231)
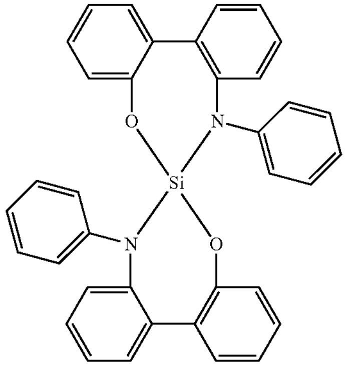
(232)
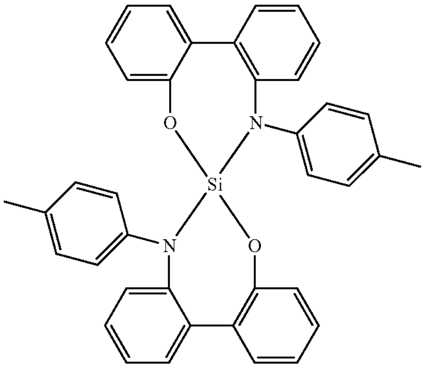

-continued
(233)
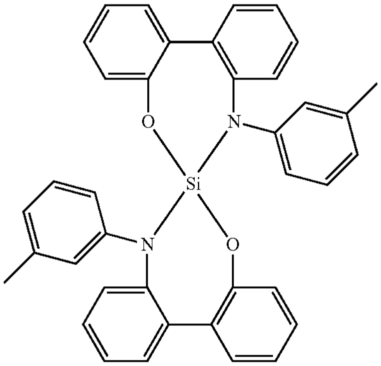
(234)
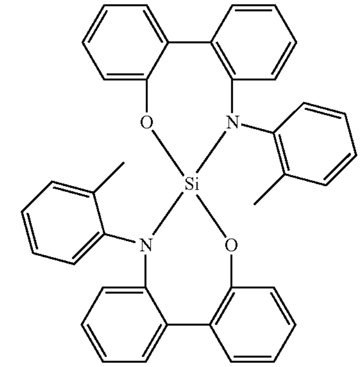
(235)
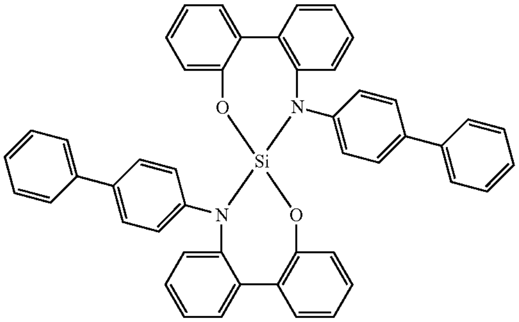
(236)
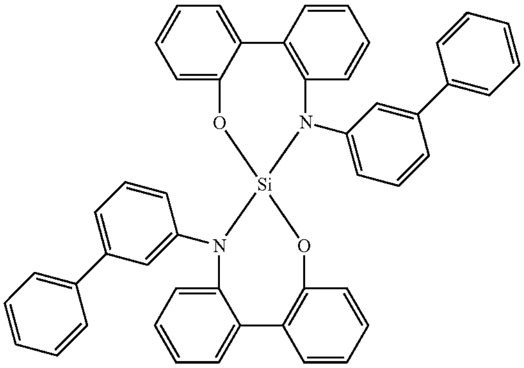
-continued
(237)
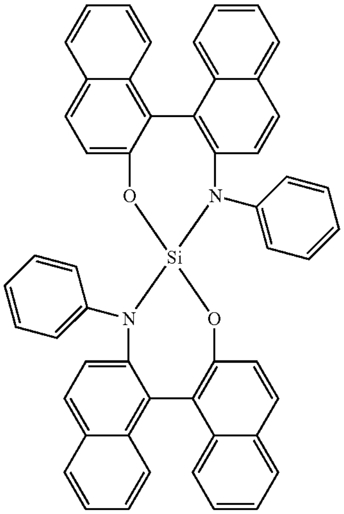
(238)
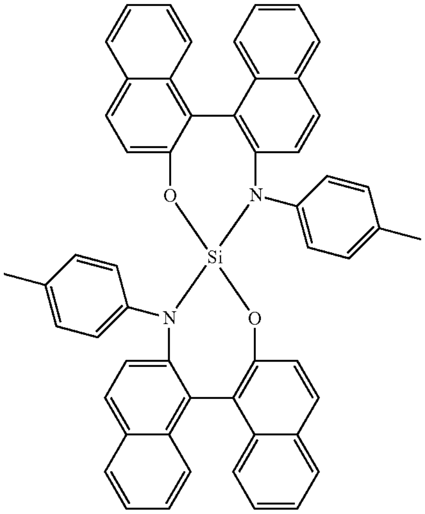
(239)
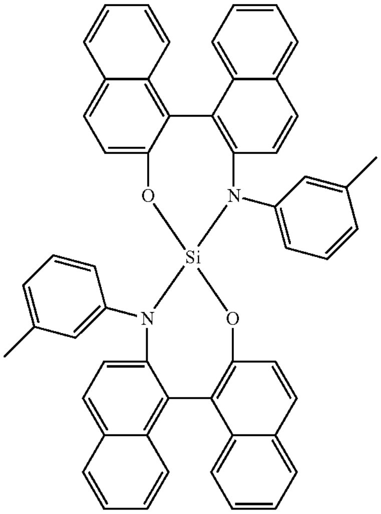

-continued
(240)
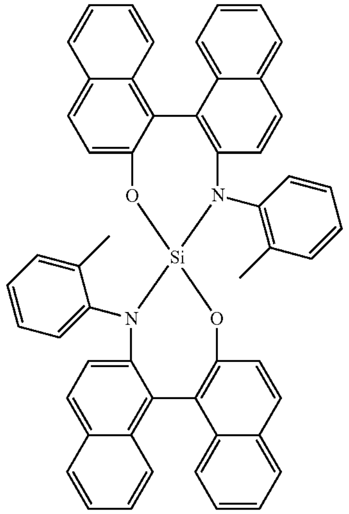
(241)
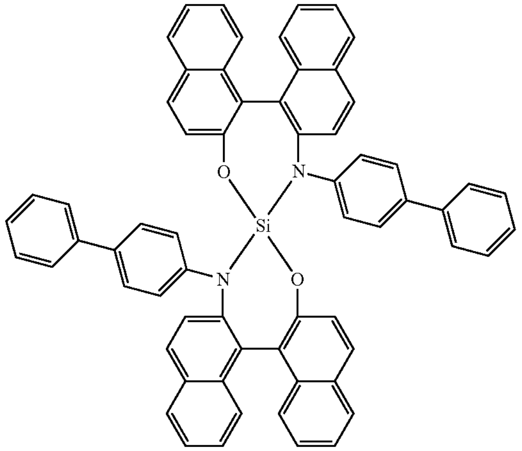
(242)
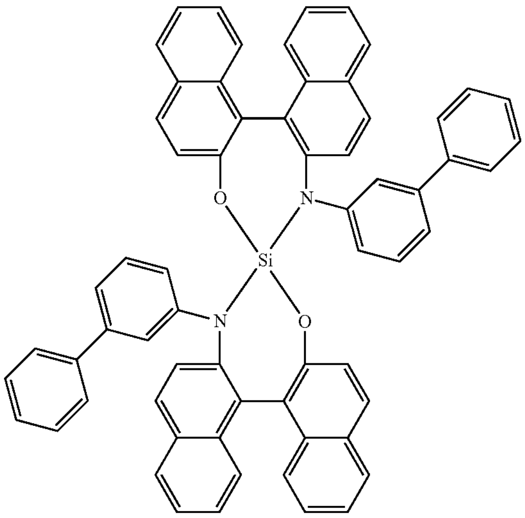
-continued
(243)
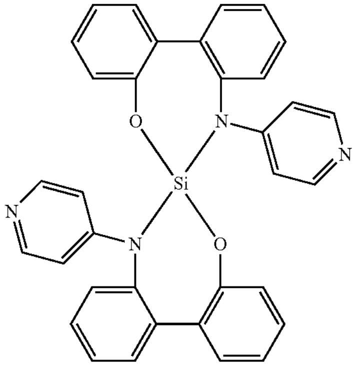
(244)
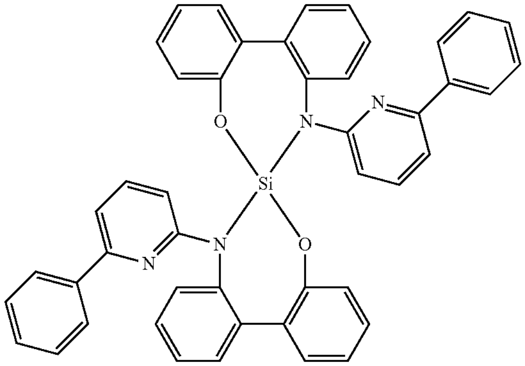
(245)
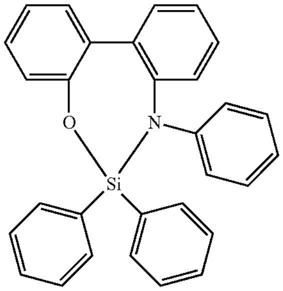
(246)
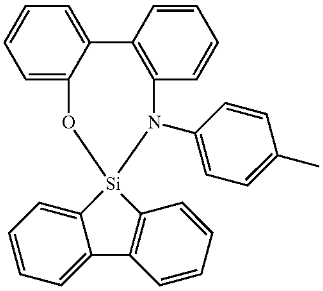

-continued
(247)
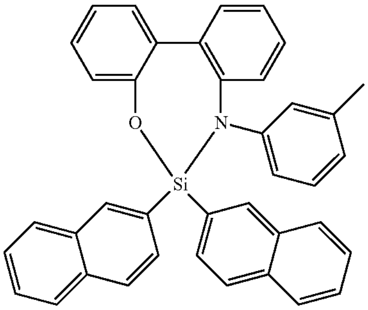
(248)
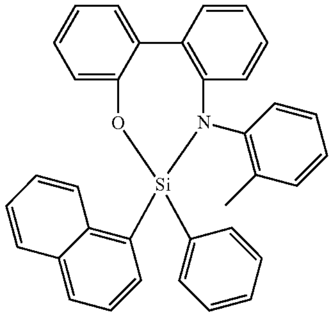
(249)
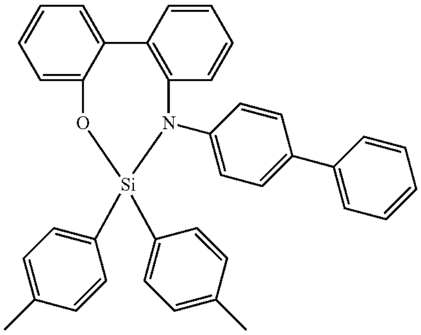
(250)
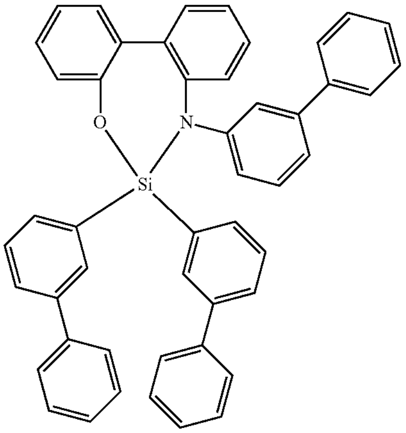
-continued
(252)
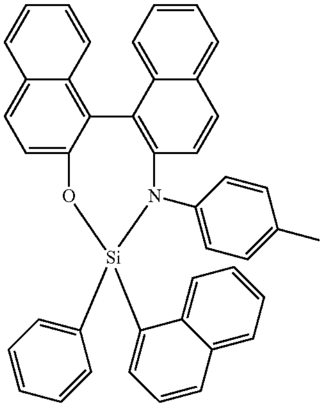
(253)
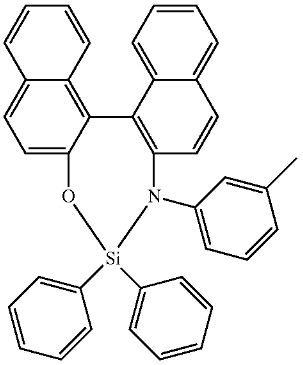
(254)
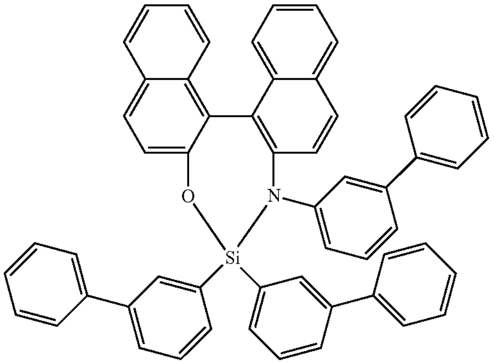
(255)
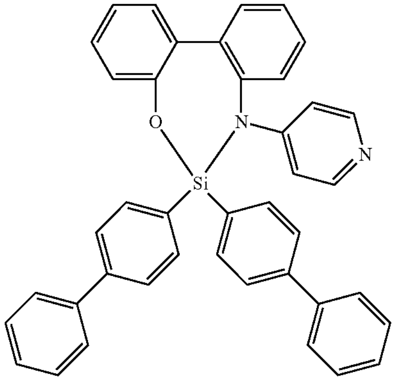

-continued
(256)
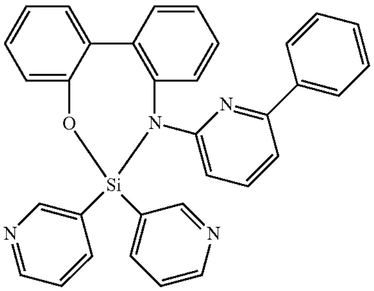
(257)
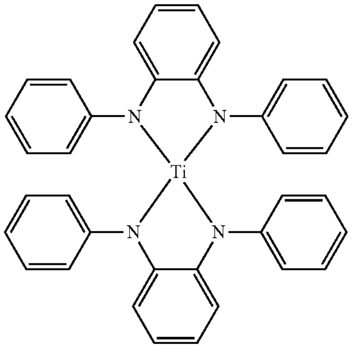
(258)
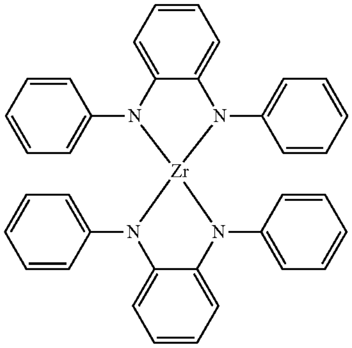
(259)
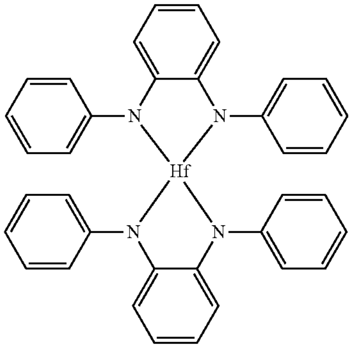
-continued
(260)
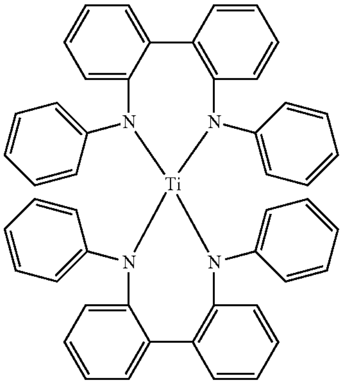
(261)
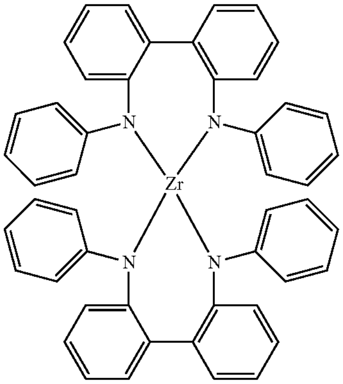
(262)
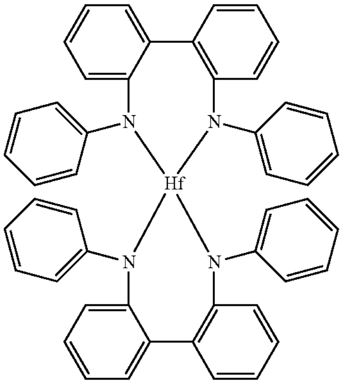
(263)
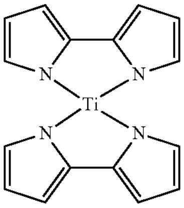
(264)
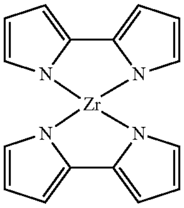

-continued
(265)
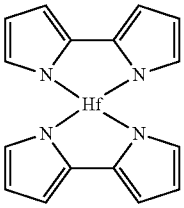
(266)
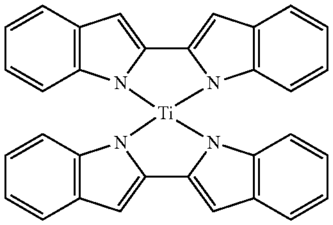
(267)
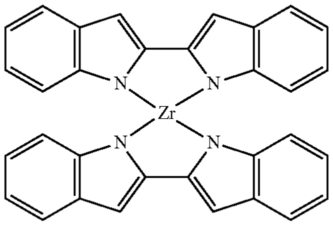
(268)
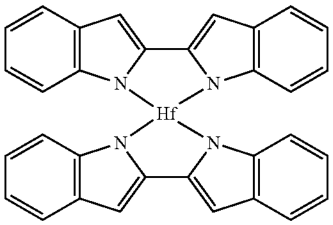
(269)
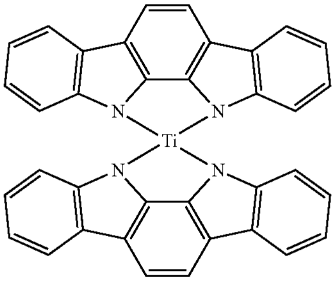
(270)
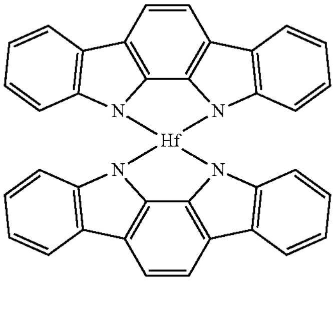
-continued
(271)
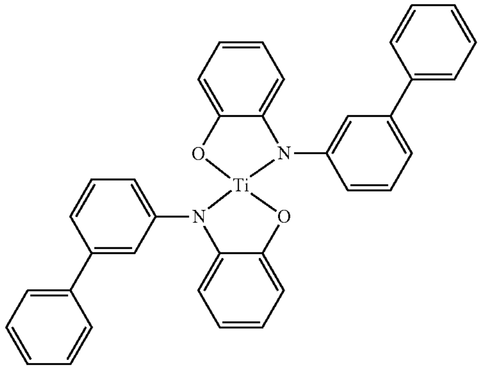
(272)
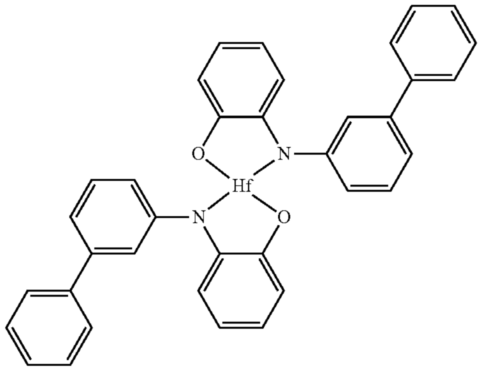
(273)
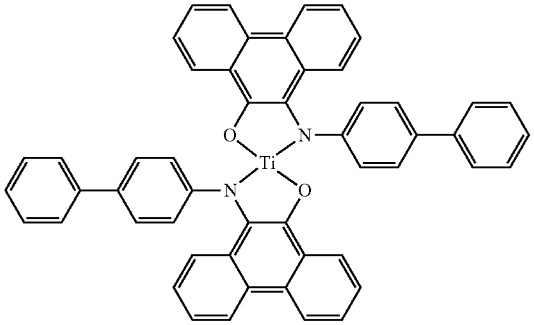
(274)
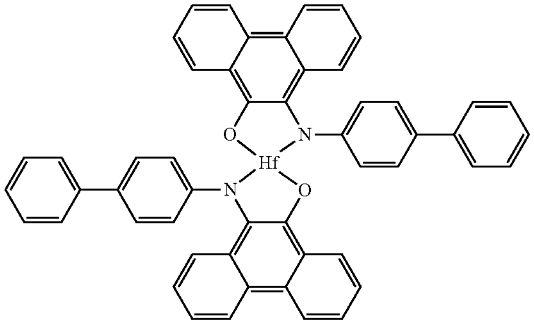

-continued (275)

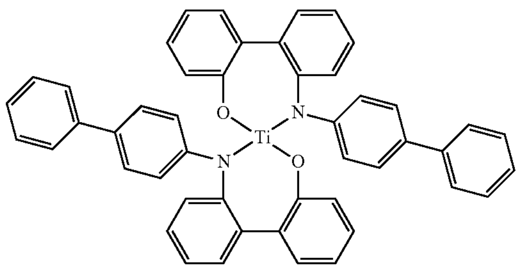

(276)

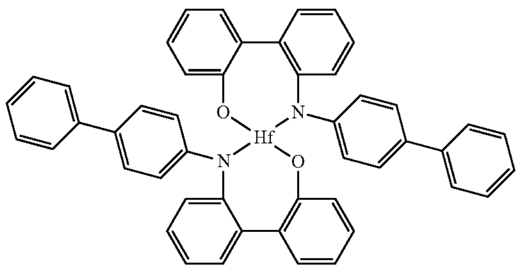

(277)

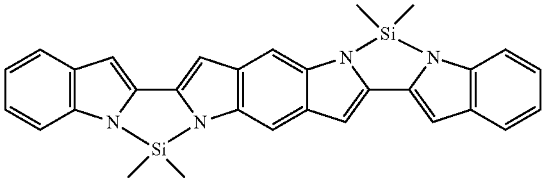

(278)

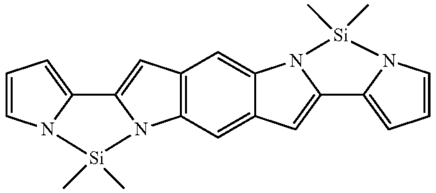

(279)

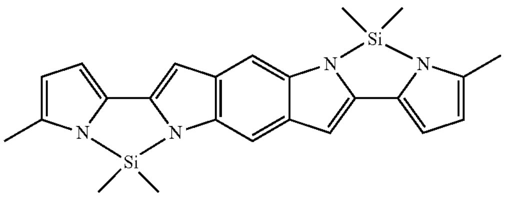

-continued (280)

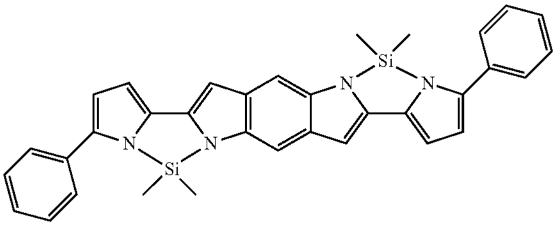

The compounds according to the invention and the organic electroluminescent devices produced therewith are distinguished by the following surprising advantages over the prior art:

1. In contrast to many compounds in accordance with the prior art, which undergo partial or complete pyrolytic decomposition during sublimation, the compounds according to the invention and the compounds of the formulae (9*) to (17*) have high thermal stability.
2. The compounds according to the invention and the compounds of the formulae (9*) to (17*), employed in organic electroluminescent devices, result in high efficiencies and in steep current-voltage curves with low use voltages.
3. The compounds according to the invention and the compounds of the formulae (9*) to (17*), employed in the electron-blocking or exciton-blocking layer of an organic electroluminescent device, result, in particular, in very high efficiencies of phosphorescent OLEDs.
4. The compounds according to the invention and the compounds of the formulae (9*) to (17*), employed as matrix material for fluorescent or phosphorescent emitters, result in high efficiencies and in long life-times. This applies, in particular, if the compounds are employed in combination with a further host material and a phosphorescent emitter.

These above-mentioned advantages are not accompanied by an impairment of the other electronic properties.

The invention is explained in greater detail by the following examples without wishing to restrict it thereby. The person skilled in the art will be able to prepare further complexes according to the invention from the descriptions without inventive step and use them in organic electronic devices or use the process according to the invention and thus carry out the invention throughout the range disclosed.

EXAMPLES

The following syntheses are carried out, unless indicated otherwise, in dried solvents under a protective-gas atmosphere. The solvents and reagents can be purchased from ALDRICH or ABCR.

Examples 1-9

Synthesis of the Diamines

The diamines shown below can be prepared from the corresponding dibromoaromatic compounds by reaction with the corresponding arylamines analogously to T. Wenderski et al., Tetrahedron Letters, 45(37), 2004, 6851.

| Ex. | Aniline | o-Phenylenediamine | Yield |
|---|---|---|---|
| 1 | 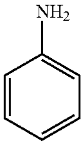 | 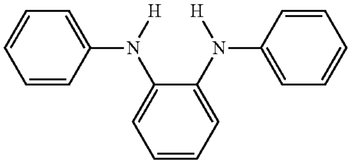 [SMILES: c1ccc(Nc2ccccc2Nc2ccccc2)cc1] | 85.0% |
| 2 | 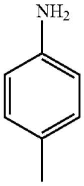 | 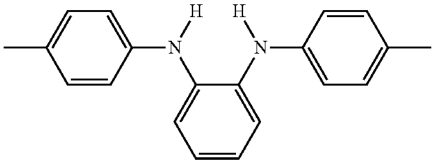 | 88.5% |
| 3 | 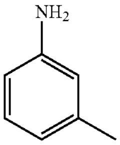 | 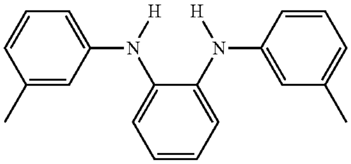 [SMILES: Cc1cccc(Nc2ccccc2Nc2cccc(C)c2)c1] | 72.3% |
| 4 | 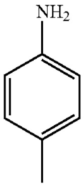 | 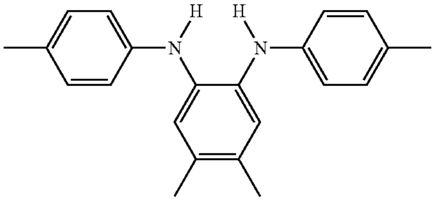 | 61.4% |
| 5 | 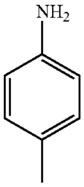 | 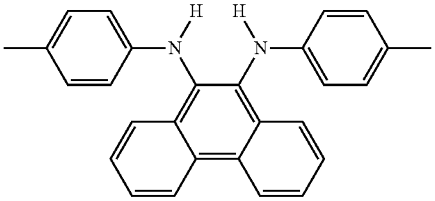 | 77.5% |
| 6 | 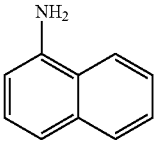 [SMILES: Nc1cccc2ccccc12] | 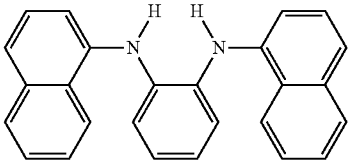 [SMILES: c1ccc(Nc2cccc3ccccc23)c(Nc2cccc3ccccc23)c1] | 41.2% |
| 7 | 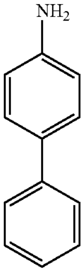 [SMILES: Nc1ccc(-c2ccccc2)cc1] | 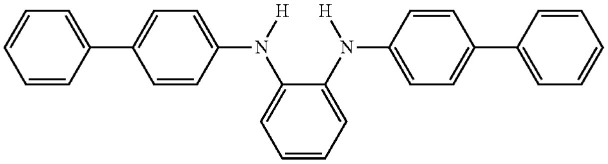 [SMILES: c1ccc(-c2ccc(Nc3ccccc3Nc3ccc(-c4ccccc4)cc3)cc2)cc1] | 76.9% |

-continued

| Ex. | Aniline | o-Phenylenediamine | Yield |
|---|---|---|---|
| 8 | 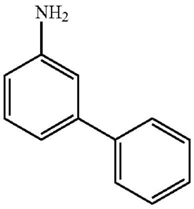 [SMILES: Nc1cccc(-c2ccccc2)c1] | 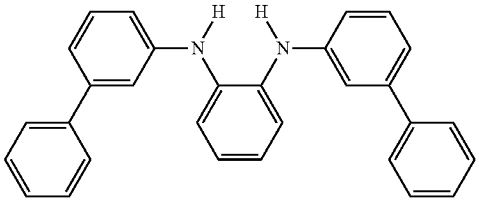 [SMILES: c1ccc(-c2cccc(Nc3ccccc3Nc3cccc(-c4ccccc4)c3)c2)cc1] | 67.1% |
| 9 | 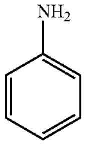 | 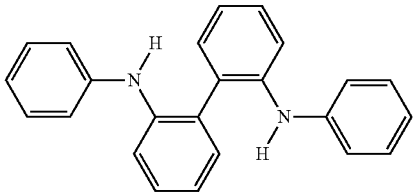 [SMILES: c1ccc(Nc2ccccc2-c2ccccc2Nc2ccccc2)cc1] | 53.3% |

Examples 10-18

Synthesis of Compounds According to the Invention 240 ml (600 mmol) of n-butyllithium, 2.5 molar in n-hexane, are added to a solution of 300 mmol of the corresponding diamine in accordance with Examples 1 to 9 in 2000 ml of diethyl ether at room temperature with stirring. When the addition is complete and the exothermic reaction has subsided, stirring is continued for 1 h, and a mixture of 25.5 g (150 mmol) of silicon tetrachloride and 100 ml of diethyl ether is then added dropwise. When the addition is complete and the exothermic reaction has subsided, stirring is continued for 1 h, the diethyl ether is then removed in vacuo, the residue is taken up in about 300 ml of toluene and chromatographed on aluminium oxide, basic, activity grade 1. The crude product obtained in this way is subsequently recrystallised four times from toluene/ethanol (1:2, about 6 ml/g) and then sublimed twice in a high vacuum (p=$10^{-5}$ mbar).

| Ex. | Diamine | Compound according to the invention | Yield |
|---|---|---|---|
| 10 | 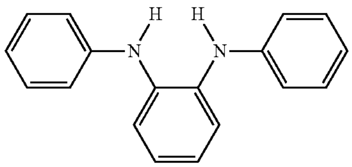 [SMILES: c1ccc(Nc2ccccc2Nc2ccccc2)cc1] | 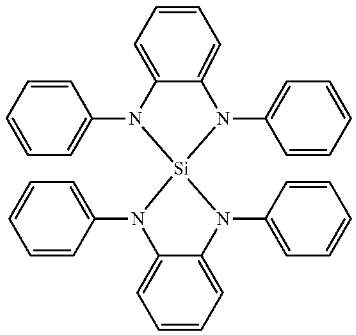 [SMILES: c1ccc(N2c3ccccc3N(c3ccccc3)[Si]23N(c2ccccc2)c2ccccc2N3c2ccccc2)cc1] | 44.0% |
| 11 | 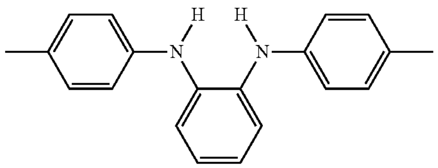 | 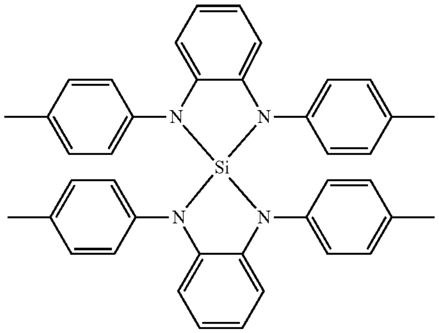 | 33.8% |

-continued
| Ex. | Diamine | Compound according to the invention | Yield |
|---|---|---|---|
| 12 | 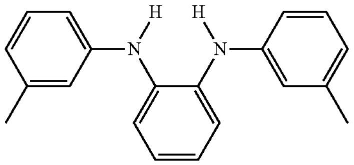 | 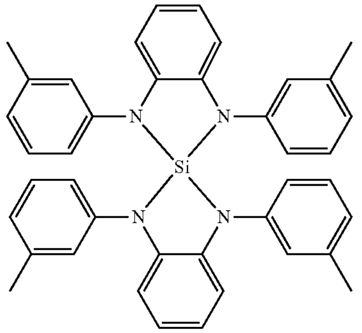 [SMILES: Cc1cccc(N2c3ccccc3N(c3cccc(C)c3)[Si]23N(c2cccc(C)c2)c2ccccc2N3c2cccc(C)c2)c1] | 27.1% |
| 13 | 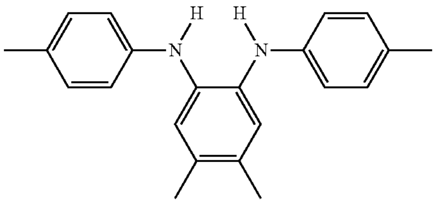 | 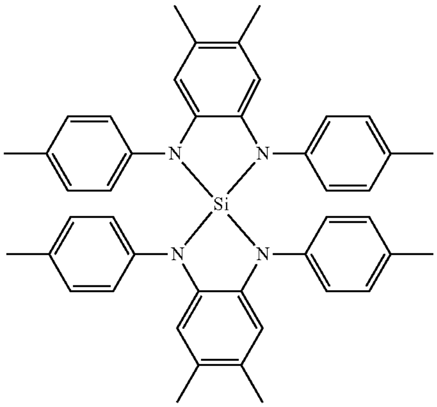 | 36.8% |
| 14 | 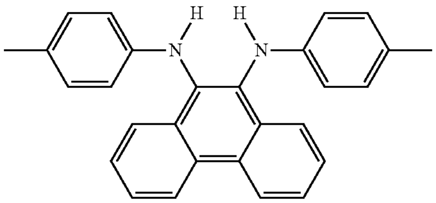 | 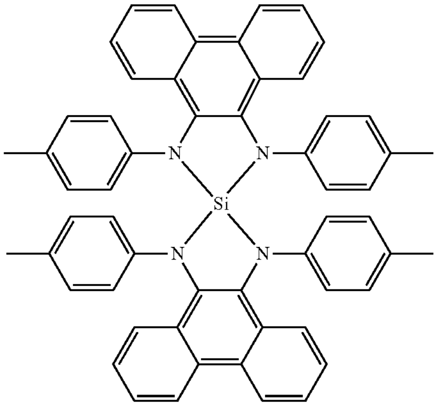 | 53.3% |
| 15 | 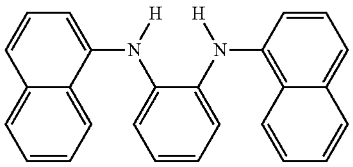 [SMILES: c1ccc(Nc2cccc3ccccc23)c(Nc2cccc3ccccc23)c1] | 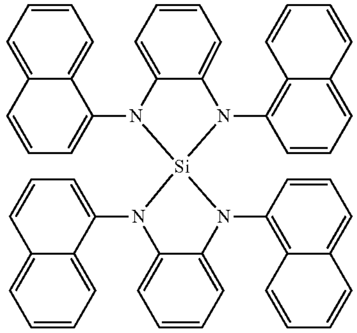 [SMILES: c1ccc2c(c1)N(c1cccc3ccccc13)[Si]1(N2c2cccc3ccccc23)N(c2cccc3ccccc23)c2ccccc2N1c1cccc2ccccc12] | 61.0% |

-continued

| Ex. | Diamine | Compound according to the invention | Yield |
|---|---|---|---|
| 16 | 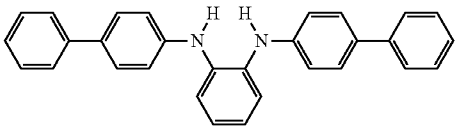 [SMILES: c1ccc(-c2ccc(Nc3ccccc3Nc3ccc(-c4ccccc4)cc3)cc2)cc1] | 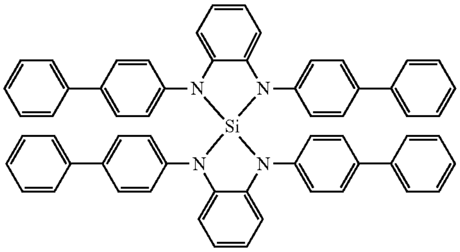 [SMILES: c1ccc(-c2ccc(N3c4ccccc4N(c4ccc(-c5ccccc5)cc4)[Si]34N(c3ccc(-c5ccccc5)cc3)c3ccccc3N4c3ccc(-c4ccccc4)cc3)cc2)cc1] | 55.4% |
| 17 | 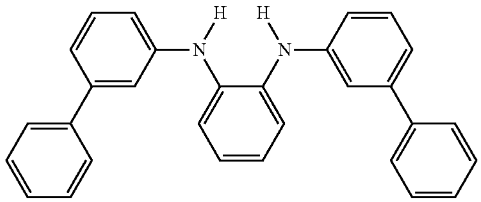 [SMILES: c1ccc(-c2cccc(Nc3ccccc3Nc3cccc(-c4ccccc4)c3)c2)cc1] | 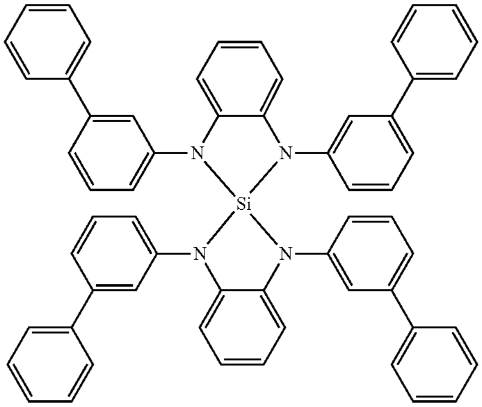 [SMILES: c1ccc(-c2cccc(N3c4ccccc4N(c4cccc(-c5ccccc5)c4)[Si]34N(c3cccc(-c5ccccc5)c3)c3ccccc3N4c3cccc(-c4ccccc4)c3)c2)cc1] | 32.0% |
| 18 | 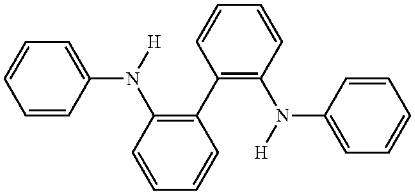 [SMILES: c1ccc(Nc2ccccc2-c2ccccc2Nc2ccccc2)cc1] | 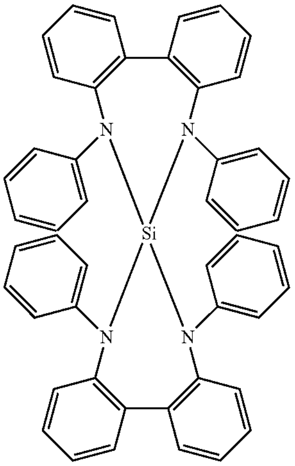 [SMILES: c1ccc(N2c3ccccc3-c3ccccc3N(c3ccccc3)[Si]23N(c2ccccc2)c2ccccc2-c2ccccc2N3c2ccccc2)cc1] | 17.9% |

Examples 19-22

Synthesis of Compounds According to the Invention 240 ml (600 mmol) of n-butyllithium, 2.5 molar in n-hexane, are added to a solution of 300 mmol of the corresponding diamine in accordance with Example 1 or 5 in 2000 ml of diethyl ether at room temperature with stirring. When the addition is complete and the exothermic reaction has subsided, stirring is continued for 1 h, and a mixture of 150 mmol of the corresponding dichlorodiarylsilane or -dialkylsilane and 100 ml of diethyl ether is then added dropwise. When the addition is complete and the exothermic reaction has subsided, stirring is continued for 1 h, the diethyl ether is then removed in vacuo, the residue is taken up in about 300 ml of toluene and chromatographed on aluminium oxide, basic, activity grade 1. The crude product obtained in this way is subsequently recrystallised four times from toluene/ethanol (1:2, about 6 ml/g) and then sublimed twice in a high vacuum ($p=10^{-5}$ mbar).

| Ex. | Diamine | Compound according to the invention | Yield |
|---|---|---|---|
| 19 | 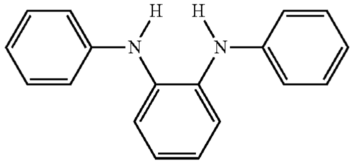 [SMILES: c1ccc(Nc2ccccc2Nc2ccccc2)cc1] | 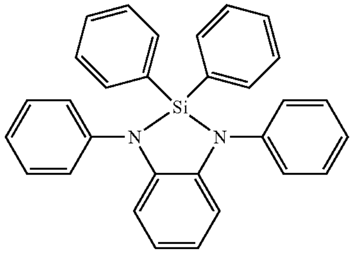 [SMILES: c1ccc(N2c3ccccc3N(c3ccccc3)[Si]2(c2ccccc2)c2ccccc2)cc1] | 71.7% |
| 20 | 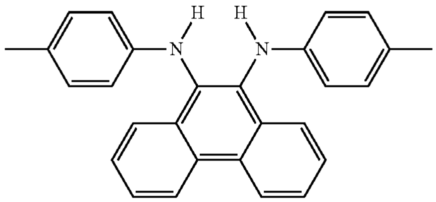 | 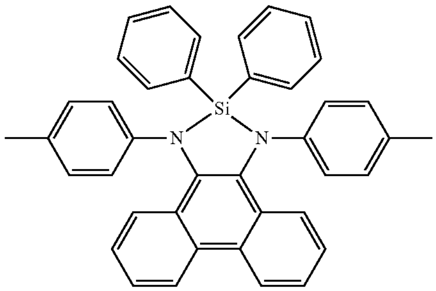 | 58.5% |
| 21 | 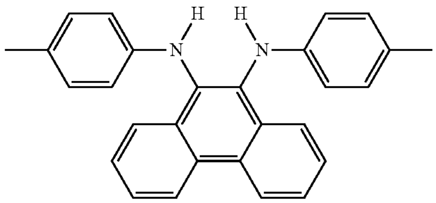 | 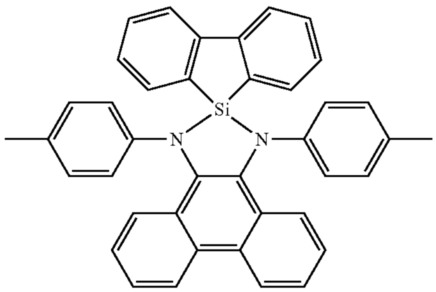 | 72.0% |
| 22 | 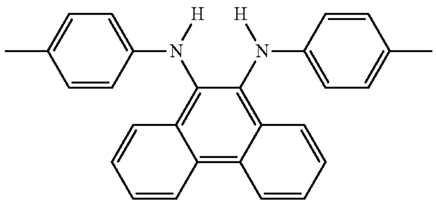 | 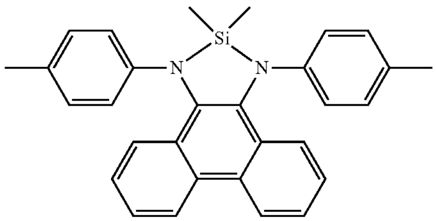 | 66.1% |

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in Examples 23 to 46 below (see Tables 1 and 2). Small glass plates coated with structured ITO (indium tin oxide) having a thickness of 150 nm are, for improved processing, coated with 20 nm of PEDOT (poly(3,4-ethylenedioxy-2,5-thiophene), spin-coated from water; purchased from H. C. Starck, Goslar, Germany). These coated glass plates form the substrates to which the OLEDs are applied. In principle, the OLEDs have the following layer structure: substrate/hole-injection layer (HIL, 20 nm with HIL1)/hole-transport layer (HTL, 20 nm with HTM1)/electron-blocking layer (EBL, 20 nm)/emission layer (EML, 40 nm)/electron-transport layer (ETL, 20 nm with ETL1)/electron-injection layer (EIL, 1 nm with LiF) and finally a cathode. The cathode is formed by an aluminium layer with a thickness of 100 nm. The precise structure of the OLEDs, in particular the structure of the EBL, EML and HBL, is given in Table 1 for green-emitting OLEDs and in Table 2 for blue-emitting OLEDs. The materials used for the production of the OLEDs are shown in Table 3.

All materials are vapour-deposited thermally in a vacuum chamber. The emission layer here always consists of at least one matrix material (host material) and an emitting dopant (emitter), which is admixed with the matrix material or materials in a certain volume proportion by co-evaporation. A reference such as M1:M2:TEG1 (55%:35%:10%) here means that the material M1 is present in the layer in a volume proportion of 55%, M2 in a proportion of 35% and TEG1 in a proportion of 10%.

The still unoptimised OLEDs are characterised by standard methods. For this purpose, the electroluminescence spectra, the current efficiency (measured in cd/A), the power efficiency (measured in Im/W) and the external quantum efficiency (EQE, measured in percent) as a function of the luminous density, calculated from current-voltage-luminance characteristic lines (IUL characteristic lines), and the lifetime are determined. The lifetime is defined as the time after which the luminous density has dropped to a certain proportion from a certain initial luminous density $I_0$. The term LD50 means that the lifetime given is the time at which the luminous density has dropped to $0.5 \cdot I_0$ (to 50%), i.e. from, for example, 8000 cd/m$^2$ to 4000 cd/m$^2$. The efficiencies and voltages indicated in the tables refer to the corresponding values at an operating luminance of 1000 cd/m$^2$.

As is clearly evident from the above-mentioned examples, the materials according to the invention are particularly suitable for use as electron-blocking materials or exciton-blocking materials. In this function, they result in a significant increase in the efficiency in a phosphorescent OLED and in a lower operating voltage in the case of blue-phosphorescent emitters.

TABLE 1

| Ex. | EBL | EML | Efficiency [cd/A] | Voltage [V] | Colour CIE x/y | LD50 [h] |
|---|---|---|---|---|---|---|
| 23 | — (Comp.) | M1: TEG1 (15%) | 32.8 | 4.3 | 0.33/0.61 | 32 000 |
| 24 | Ex. 10 | M1: TEG1 (15%) | 53.2 | 4.6 | 0.33/0.61 | 26 000 |

TABLE 1-continued

| Ex. | EBL | EML | Efficiency [cd/A] | Voltage [V] | Colour CIE x/y | LD50 [h] |
|---|---|---|---|---|---|---|
| 25 | Ex. 11 | M1: TEG1 (15%) | 43.8 | 4.4 | 0.33/0.61 | 29 000 |
| 26 | Ex. 13 | M1: TEG1 (15%) | 49.0 | 4.5 | 0.33/0.61 | 27 000 |
| 27 | — | M1: Ex. 10 (10%): TEG1(10%) | 38.6 | 4.7 | 0.32/0.62 | 28 000 |
| 28 | Ex. 10 | M1: Ex. 10 (10%): TEG1(10%) | 54.6 | 5.9 | 0.32/0.62 | 15 000 |
| 29 | Ex. 10 | M1: Ex. 10(30%): TEG2(10%) | 48.0 | 4.4 | 0.36/0.60 | 50 000 |
| 30 | Ex. 10 | M1: TEG1 (3%): TEG3(10%) | 60.5 | 5.6 | 0.34/0.62 | 12 000 |
| 31 | Ex. 10 | M2: Ex. 10(10%): TEG1(5%) | 59.8 | 6.8 | 0.28/0.63 | 10 000 |
| 32 | Ex. 11 | M1: Ex. 11 (20%): TEG1(10%) | 55.3 | 5.6 | 0.30/0.63 | 28 000 |
| 33 | Ex. 13 | M1: Ex. 1 (20%): TEG1(10%) | | | | |

TABLE 2

| Ex. | EBL | EML | Efficiency [cd/A] | Voltage [V] | Colour CIE x/y |
|---|---|---|---|---|---|
| 34 | — (Comp.) | M1: TEB1 (15%) | 2.1 | 7.8 | 0.16/0.26 |
| 35 | Ex. 10 | M1: TEB1 (10%) | 16.5 | 8.2 | 0.16/0.27 |
| 36 | Ex. 11 | M1: TEB1 (15%) | 15.9 | 8.8 | 0.16/0.26 |
| 37 | Ex. 12 | M1: TEB1 (15%) | 16.9 | 6.8 | 0.16/0.27 |
| 38 | Ex. 13 | M1: TEB1 (15%) | 15.9 | 6.9 | 0.16/0.26 |
| 39 | Ex. 14 | M1: TEB1 (15%) | 16.3 | 7.0 | 0.16/0.26 |
| 40 | Ex. 10 | M1: Ex. 10 (10%): TEB1 (5%) | 21.6 | 8.0 | 0.16/0.28 |
| 41 | Ex. 10 | M1: Ex. 10 (10%): TEB2 (5%) | 31.5 | 5.3 | 0.15/0.34 |
| 42 | Ex. 10 | M2: Ex. 10 (10%): TEB1 (5%) | 32.1 | 8.0 | 0.14/0.26 |
| 43 | Ex. 10 | M2: Ex. 10 (10%): TEB2 (5%) | 39.3 | 6.0 | 0.14/0.32 |
| 44 | Ex. 11 | M1: Ex. 11 (10%): TEB1 (10%) | 17.6 | 8.5 | 0.15/0.29 |
| 45 | Ex. 11 | M2: Ex. 11 (10%): TEB1 (10%) | 29.9 | 9.2 | 0.15/0.26 |
| 46 | Ex. 13 | M1: Ex. 13(10%): TEB1: (10%) | 6.2 | 8.4 | 0.15/0.25 |

TABLE 3

Structural formulae of the materials used

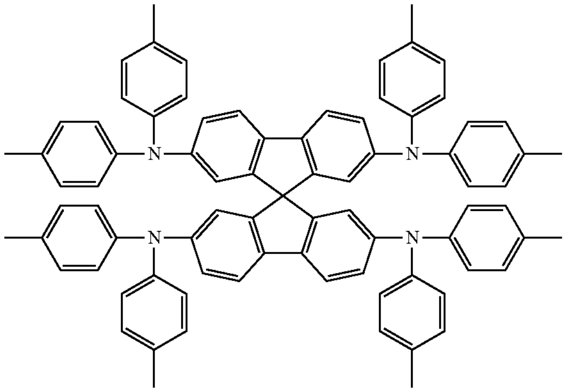

HIL1

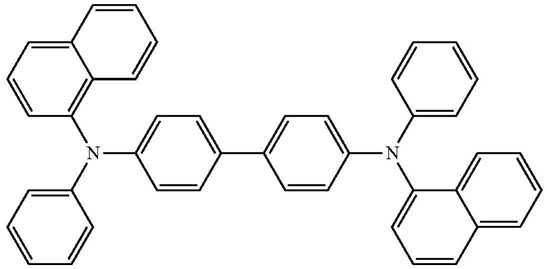 [SMILES: c1ccc(N(c2ccc(-c3ccc(N(c4ccccc4)c4cccc5ccccc45)cc3)cc2)c2cccc3ccccc23)cc1]

HTM1 (NPB)

TABLE 3-continued
Structural formulae of the materials used
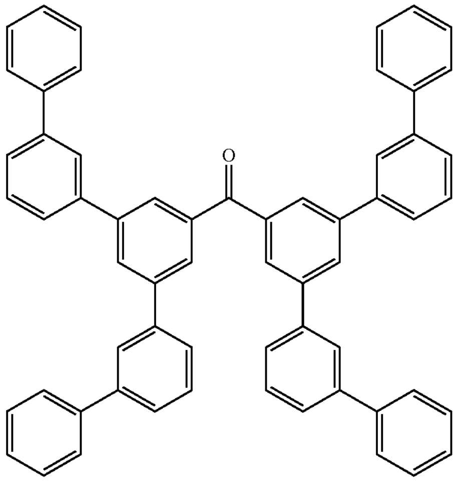 [SMILES: O=C(c1cc(-c2cccc(-c3ccccc3)c2)cc(-c2cccc(-c3ccccc3)c2)c1)c1cc(-c2cccc(-c3ccccc3)c2)cc(-c2cccc(-c3ccccc3)c2)c1]
M1
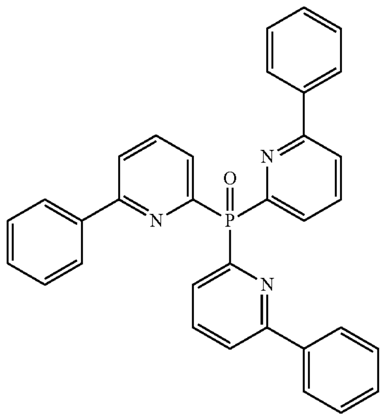 [SMILES: O=P(c1cccc(-c2ccccc2)n1)(c1cccc(-c2ccccc2)n1)c1cccc(-c2ccccc2)n1]
M2
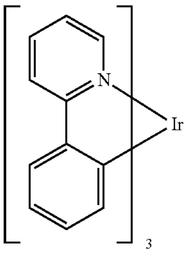
TEG1
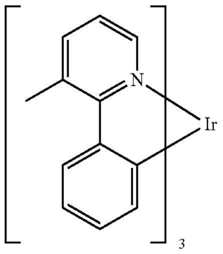
TEG2
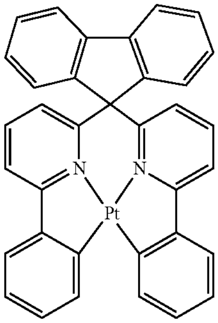
TEG3
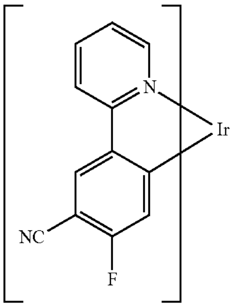
TEB1
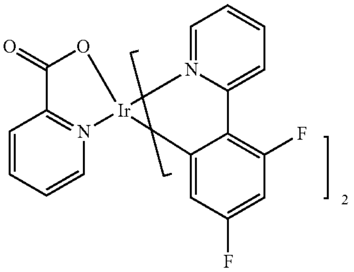
TEB2
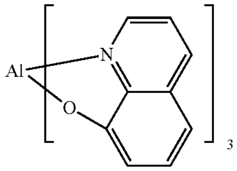
ETM1 (Alq)

The invention claimed is:

1. A compound comprising at least one moiety of formula (9):

formula (9)

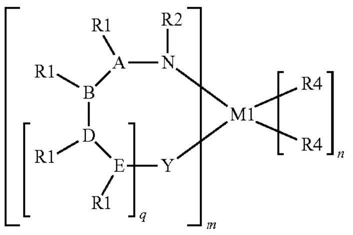

wherein

M1 is Si q is 0 or 1;

A, B, D and E are each a C atom; a double bond or aromatic bond is present between A and B if A does not form an aromatic system with N, and a single bond is present between A and B if A forms an aromatic system with N; furthermore, a double bond or aromatic bond is present between D and E if E does not form an aromatic system with Y, and a single bond is present between D and E if E forms an aromatic system with Y;

Y is selected from the group consisting of NR2, O and S;

R1 is identical or different on each occurrence and is selected from the group consisting of H, D, F, Cl, Br, I, CN, $NO_2$, $N(R3)_2$, a straight-chain alkyl, alkoxy or thioalkyl group having 1 to 40 C atoms or a branched or cyclic alkyl, alkoxy or thioalkyl group having 3 to 40 C atoms or an alkenyl group having 2 to 40 C atoms, each of which are optionally substituted by one or more radicals R3, where one or more non-adjacent $CH_2$ groups are optionally replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms are optionally replaced by D, F, Cl, Br, I, CN or $NO_2$, an aromatic or heteroaromatic ring system having 5 to 60 aromatic ring atoms, optionally substituted by one or more radicals R3, an aryloxy or heteroaryloxy group having 5 to 60 aromatic ring atoms, which is optionally substituted by one or more radicals R3, or a combination of these systems, where two or more adjacent substituents R1 optionally form a monocyclic or polycyclic aliphatic, aromatic or heteroaromatic ring system which is condensed in a linear or angular manner and which is optionally substituted by one or more radicals R3;

R2 is identical or different on each occurrence and is selected from the group consisting of a straight-chain alkyl group having 1 to 40 C atoms or a branched or cyclic alkyl group having 3 to 40 C atoms, each of which is optionally substituted by one or more radicals R3, where one or more non-adjacent $CH_2$ groups are optionally replaced by R3C═CR3, C≡C or C═O and where one or more H atoms are optionally replaced by F, Cl, Br, I, CN or $NO_2$, an aromatic or heteroaromatic ring system having 5 to 60 aromatic ring atoms, optionally substituted by one or more radicals R3, or a combination of these systems; with the proviso that at least one group R2 which represents an aromatic or heteroaromatic ring system, optionally substituted by one or more radicals R3, is present in the structure of the formula (I); R1 and R2 which are adjacent to one another in the 1,2-position in the moiety of the formula (I) optionally form a monocyclic or polycyclic aliphatic, aromatic or heteroaromatic ring system which is condensed in a linear or angular manner and which is optionally substituted by one or more radicals R3;

R3 is identical or different on each occurrence and is selected from the group consisting of H, D, an aliphatic hydrocarbon radical having 1 to 20 C atoms, an aromatic or heteroaromatic ring system having 5 to 30 aromatic ring atoms, in which one or more H atoms are optionally replaced by D, F, Cl, Br, I, CN or $NO_2$, where two or more adjacent substituents R3 optionally form a mono- or polycyclic aliphatic, aromatic or heteroaromatic ring system which is condensed in a linear or angular manner with one another;

R4 is identical or different on each occurrence and is selected from the group consisting of $N(R3)_2$, a straight-chain alkyl, alkoxy or thioalkyl group having 1 to 40 C atoms or a branched or cyclic alkyl, alkoxy or thioalkyl group having 3 to 40 C atoms or alkenyl group having 2 to 40 C atoms, each of which is optionally substituted by one or more radicals R3, where one or more non-adjacent $CH_2$ groups are optionally replaced by R3C═CR3, C≡C, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms are optionally replaced by D, F, Cl, Br, I, CN or $NO_2$, an aromatic or heteroaromatic ring system having 5 to 60 aromatic ring atoms, optionally substituted by one or more radicals R3, an aryloxy or heteroaryloxy group having 5 to 60 aromatic ring atoms, which are optionally substituted by one or more radicals R3, or a combination of these systems, where two or more substituents R4 optionally form a monocyclic or polycyclic aliphatic, aromatic or heteroaromatic ring system which is condensed in a linear or angular manner and which is optionally substituted by one or more radicals R3;

is 1 or 2; and n is (2-m); and wherein the following compounds are excluded from the invention:

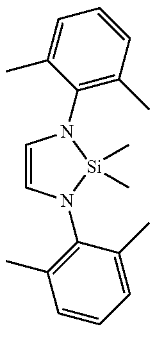

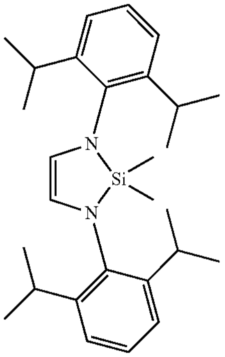

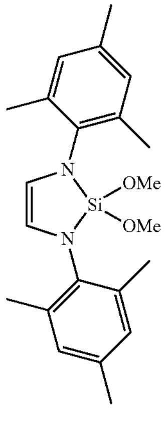

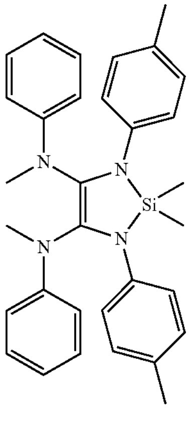

-continued

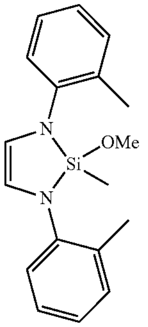

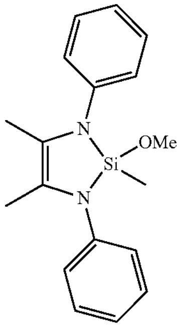

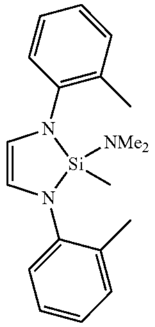

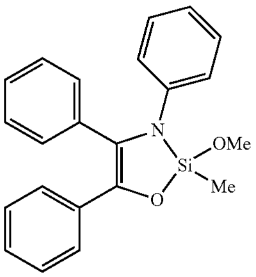

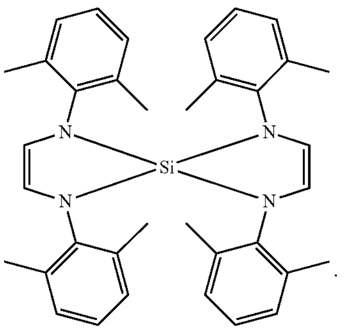

2. The compound of claim 1, wherein said compound is selected from the group consisting of formulae (10) to (17):

formula (10)

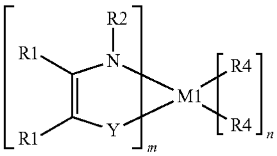

formula (11)

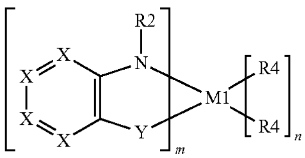

formula (12)

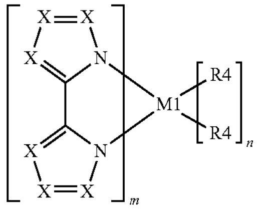

-continued formula (13)

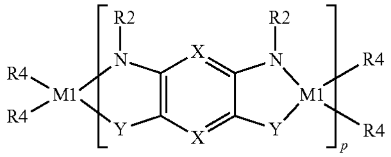

formula (14)

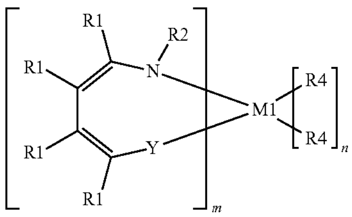

formula (15)

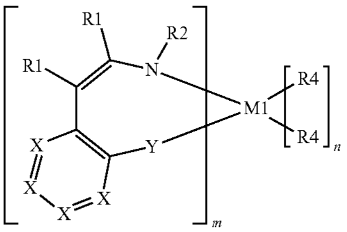

formula (16)

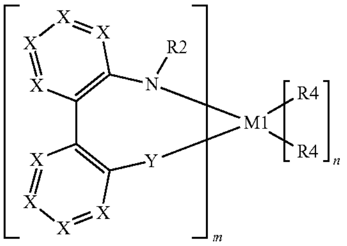

formula (17)

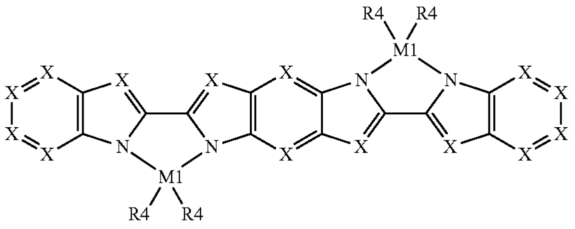

wherein M1, R1, R2, R3, R4, Y, m and n are as defined in claim 1 and p is an integer from 1 to 100,000, and wherein X is CR1.

3. The compound of claim 1, wherein m=2 and n=0.

4. The compound of claim 1, wherein Y stands for NR2 or O.

5. The compound of claim 1, wherein R4 is selected on each occurrence, identically or differently, from the group consisting of a straight-chain alkyl group having 1 to 20 C atoms and a branched or cyclic alkyl group having 3 to 20 C atoms, each of which is optionally substituted by one or more radicals R3, where one or more non-adjacent $CH_2$ groups are optionally replaced by R3C═CR3, $Si(R3)_2$, $Ge(R3)_2$, $Sn(R3)_2$, C═O, C═S, C═Se, C═NR3, P(═O)(R3), SO, $SO_2$, NR3, O, S or CONR3 and where one or more H atoms are optionally replaced by F, Cl, Br, I, CN or $NO_2$, an aromatic or heteroaromatic ring system having 5 to 60 aromatic ring atoms, optionally substituted by one or more radicals R3, or a combination of these systems, where two or more substituents R4 optionally form a monocyclic or polycyclic aliphatic, aromatic or heteroaromatic ring system which is condensed in a linear or angular manner and which is optionally substituted by one or more radicals R3.

6. The compound of claim 1, wherein:

R2 is on each occurrence, identically or differently, an aromatic or heteroaromatic ring system having 5 to 30 aromatic ring atoms, in which one or more H atoms are optionally replaced by F atoms and which may in each case be substituted by one or more radicals R3; and Y is NR2.

7. A process for preparing a compound of claim 1 comprising the step of reacting $M1(Hal)_{2m}(R4)_{2n}$, wherein M1, m, and n are as defined in claim 1 and Hal is Cl, Br, or I, with a corresponding diamine, aminoalcohol, aminothiol, or the respective deprotonated compound.

8. An oligomer, polymer, or dendrimer comprising one or more compounds of claim 1, wherein one or more bonds are present from said one or more compounds of claim 1 to said polymer, oligomer, or dendrimer.

9. The compound of claim 1, wherein the compound is present in an electronic device.

10. The compound of claim 1, wherein the compound is present in an organic electroluminescent device.

* * * * *